US009429561B2

(12) United States Patent
Burrows et al.

(10) Patent No.: US 9,429,561 B2
(45) Date of Patent: Aug. 30, 2016

(54) DETECTION OF NUCLEIC ACID LESIONS AND ADDUCTS USING NANOPORES

(71) Applicant: UNIVERSITY OF UTAH RESEARCH FOUNDATION, Salt Lake City, UT (US)

(72) Inventors: Cynthia J. Burrows, Salt Lake City, UT (US); Henry S. White, Salt Lake City, UT (US); Ryuji Kawano, Salt Lake City, UT (US); Aaron M. Fleming, Salt Lake City, UT (US); Na An, Salt Lake City, UT (US)

(73) Assignee: UNIVERSITY OF UTAH RESEARCH FOUNDATION, Salt Lake City, UT (US)

( * ) Notice: Subject to any disclaimer, the term of this patent is extended or adjusted under 35 U.S.C. 154(b) by 0 days.

(21) Appl. No.: 14/657,226

(22) Filed: Mar. 13, 2015

(65) Prior Publication Data
US 2015/0185200 A1    Jul. 2, 2015

Related U.S. Application Data

(60) Division of application No. 13/227,212, filed on Sep. 7, 2011, now Pat. No. 9,005,425, which is a continuation-in-part of application No. PCT/US2011/027433, filed on Mar. 7, 2011.

(60) Provisional application No. 61/310,822, filed on Mar. 5, 2010, provisional application No. 61/455,829, filed on Oct. 27, 2010.

(51) Int. Cl.
*G01N 27/327* (2006.01)
*G01N 33/487* (2006.01)
(Continued)

(52) U.S. Cl.
CPC ......... *G01N 33/48721* (2013.01); *B82Y 15/00* (2013.01); *C12Q 1/6827* (2013.01); *C12Q 1/6869* (2013.01); *G01N 27/44704* (2013.01)

(58) Field of Classification Search
CPC ................................................ G01N 33/48721
See application file for complete search history.

(56) References Cited

U.S. PATENT DOCUMENTS 8,394,584 B2 * 3/2013 Timp ................... C12Q 1/6827
435/287.2
9,005,425 B2    4/2015 Burrows et al.
(Continued)

FOREIGN PATENT DOCUMENTS

EP        1544310        6/2005
WO    WO 03/000920     1/2003
(Continued)

OTHER PUBLICATIONS

Merriam-Webster definition of "aperture" downloaded on Oct. 16, 2015.*
(Continued)

*Primary Examiner* — Alexander Noguerola
(74) *Attorney, Agent, or Firm* — Michael Best & Friedrich LLP

(57) ABSTRACT

Methods, systems, and compounds for detecting modified nucleic acid bases are disclosed and described. The methods provide for detecting a nucleic acid lesion and can include directing a nucleic acid adduct into a channel, wherein the nucleic acid adduct includes a nucleic acid having a lesion and a current modulating compound coupled to the nucleic acid at the lesion (110), and measuring a change in current through the channel in response to the current modulating compound to detect the lesion (112). The method can optionally include forming the nucleic acid adduct. Also provided is a method for identifying the number of repeat nucleotides in at least a portion of a nucleic acid strand, a method of assigning a registration marker within a nucleic acid, and a method of obtaining sequence information from a nucleic acid comprising assigning a registration marker on the nucleic acid.

9 Claims, 46 Drawing Sheets

(51) Int. Cl.
  B82Y 15/00   (2011.01)
  C12Q 1/68    (2006.01)
  G01N 27/447  (2006.01)

(56) References Cited

U.S. PATENT DOCUMENTS

| | | | |
|---|---|---|---|
| 2003/0099951 | A1 | 5/2003 | Akeson et al. |
| 2004/0063126 | A1 | 4/2004 | Barton et al. |
| 2007/0004047 | A1 | 1/2007 | Lee et al. |
| 2008/0311582 | A1 | 12/2008 | Bayley et al. |
| 2010/0025263 | A1 | 2/2010 | White et al. |
| 2010/0035260 | A1* | 2/2010 | Olasagasti ........... C12Q 1/6869 435/6.16 |
| 2010/0038243 | A1 | 2/2010 | White et al. |
| 2010/0243449 | A1* | 9/2010 | Oliver .......................... 204/450 |
| 2010/0320094 | A1 | 12/2010 | White et al. |

FOREIGN PATENT DOCUMENTS

| | | |
|---|---|---|
| WO | WO 2007/146158 | 12/2007 |
| WO | WO 2009007743 | 1/2009 |
| WO | WO 2011/109825 | 9/2011 |

OTHER PUBLICATIONS

Singer et al., "Nanopore Based Sequence Specific Detection of Duplex DNA for Genomic Profiling," Nano Lett. 2010, 10, 738-742.*
Borsenberger et al., "Chemically Labeled Nucleotides and Oligonucleotides Encode DNA for Sensing with Nanopores," J. Am. Chem. Soc. 2009, 131, 7530-7531.*
White et al., "Single Ion-Channel Recordings Using Glass Nanopore Membranes," J. Am. Chem. Soc. 2007, 129, 11766-11775.*
Akeson, M. et al., "Microsecond Time-Scale Discrimination Among Polycytidylic Acid, Polyadenylic Acid, and Polyuridylic Acid as Homopolymers or as Segments Within Single RNA Molecules" Biophys J. 1999, 77, 3227-3233.
Astier, Y. et al., "Toward Single Molecule DNA Sequencing: Direct Identification of Ribonucleoside and Deoxyribonucleoside 5'-Monophosphates by Using an Engineered Protein Nanopore Equipped with a Molecular Adapter" J. Am. Chem. Soc. 2006, 128, 1705-1710.
Azqueta, A. et al., "DNA oxidation: Investigating its key role in environmental mutagenesis with the comet assay" Mutal. Res. 2009, 674, 101-108.
Borsenberger, V. et al., "Chemically Labeled Nucleotides and Oligonucleotides Encode DNA for Sensing with Nanopores" J. Am. Chem. Soc. 2009, 131, 7530-7531.
Branton, D. et al., "The potential and challenges of nanopore sequencing" Nat. Biotech. 2008, 26, 1146-1153.
Cadet, 1. et al., "Oxidatively generated base damage to cellular DNA" Free Radic. Biol. Med. 2010, 49, 9-21.
Cadet, J. et al., "Measurement of oxidatively generated base damage in cellular DNA and urine" Free Radic. Biol. Med. 2010, 48, 1457-1459.
Clarke, J. et al., "Continuous base identification for single-molecule nanopore DNA sequencing" Nature Nanotech. 2009, 4, 265-270.
Cooke, M. S. et al., "Does measurement of oxidative damage to DNA have clinical significance?" Clinica Chimica Acta 2006, 365, 30-49.
David, S. S. et al., "Base-excision repair of oxidative DNA damage" S. Nature 2007, 447, 941-950.
Deamer, D. W. et al., "Characterization of Nucleic Acids by Nanopore Analysis" Ace. Chem. Res. 2002, 35, 817-825.
Delaney, J. C. et al., "Biological Properties of Single Chemical-DNA Adducts: A Twenty Year Perspective" Chem. Res. Toxicol. 2008, 21, 232-252.
Fologea, D. et al., "DNA conformation and base number simultaneously determined in a nanopore" Nano Left. 2005, 5, 1905-1909.
Gedik, C. M. et al. FASEB Journal 2005, 19, 82-84.
Hada, M. et al., "Spectrum of Complex DNA Damages Depends on the Incident Radiation" Radiat. Res. 2006, 165, 223-230.
Hosford, M. E. et al. "Spermine participates in oxidative damage of guanosine and 8-oxoguanosine leading to deoxyribosylurea formation" J. Am. Chem. Soc 2004, 126, 9540•9541.
Kasianowicz, J. J. et al., "Characterization of individual polynucleotide molecules using a membrane channel" Proc. Natl. Acad. Sci. USA 1996, 93, 13770-13773.
Kojima, N., et al., "Construction of highly reactive trpbes for abasic site detection by introduction of an aromatic and a guanidine residue into an aminooxy group" Journal of the American Chemical Society. vol. 131(37), pp. 13208-13209 (Sep. 23, 2009).
Kornyushyna, O. et al. "In vitro nucleotide misinsertion opposite the oxidized guanosine lesions spiroiminodihydantoin and guanidinohydantoin and DNA synthesis past the lesions using *Escherichia coli* DNA polymerases I (Klenow Fragment)" Biochemistry 2002,41, 15304•15314.
Lubensky et al., "Driven Polymer Translocation Through a Narrow Pore" Biophys. J., vol. 77, No. 4, pp. 1824-1838, dated Oct. 1, 1999.
Luo, W. et al., "Characterization of Spiroiminodihydantoin as a Product of One-Electron Oxidation of 8-Oxo-7,8-dihydroguanosine" J. Org. Left. 2000, 2, 613-617.
Mangal, D. et al., "Analysis of 7,8-Dihydro-8-oxo-2'-deoxyguanosine in Cellular DNA during Oxidative Stress" Chem. Res. Toxicol. 2009, 22, 788-797.
Meller, A. et al., "Rapid nanopore discrimination between single polynucleotide molecules" Natl. Acad. Sci. 2000, 97, 1079-1084.
Meller, A. et al., "Voltage-Driven DNA Translocations through a Nanopore" Phys. Rev. Left. 2001, 86, 3435-3438.
Mitchell, N. et al., "Chemical Tags Facilitate the Sensing of Individual DNA Strands with Nanopores"Angew. Chem. Int. Ed. 2008, 47, 5565-5568.
Muller, J. G. et al., "Gel electrophoretic detection of 7,8-dihydro-8-oxoguanine and 7,8-dihydro-8-oxoadenine via oxidation by Ir(IV)" Nucleic Acids Res. 1998, 26, 2247-2249.
Nakane, J. et al., "A Nanosensor for Transmembrane Capture and Identification of Single Nucleic Acid Molecules" A. Biophys. J. 2004, 87, 615-621.
PCT/US2011/027433 International Search Report dated Dec. 28, 2011 (6 pages).
PCT/US2011/027433 Written Opinion of the International Searching Authority dated Dec. 28, 2011 (4 pages).
Pfeifer, G. P. et al., "Mutational spectra of human cancer" Hum Genet 2009, 125,493-506.
Purnell, R F. et al., "Discrimination of Single Base Substitutions in a DNA Strand Immobilized in a Biological Nanopore" ACS Nano 2009, 9, 2533-2538.
Purnell, R. F. et al.,"Nucleotide Identification and Orientation Discrimination of DNA Homopolymers Immobilized in a Protein Nanopore" J. Nano Left. 2008, 8, 3029-3034.
Steenken, S. et al., "The Trap Depth (in DNA) of 8-Oxo-7,8-dihydro-2¢deoxyguanosine as Derived from Electron-Transfer Equilibria in Aqueous Solution" J. Am. Chem. Soc. 2000, 122, 2372-2374.
Stoddart, D. et al. Angew. Chem. Int. Ed. 2010, 49, 556-559.
Stoddart, D. et al., "Single-nucleotide discrimination in immobilized DNA oligonucleotides with a biological nanopore" Proc. Natl. Acad. Sci. 2009, 106, 7702-7707.
Wallace, E. V. B. et al. "Identification of Epigenetic DNA Modifications with a Protein Nanopore" Chem. Commun. Published Online. Oct. 6, 2010. http://pubs.rsc.org (accessed Oct. 19, 2010).
White, R. J. et al., "Single ion-channel recordings using glass nanopore membranes" J. Am. Chern. Soc. 2007, 129, 11766-00775.
Xu, X. et al., "DNA-protein cross-links between guanine and lysine depend on the mechanism of oxidation for formation of C5 vs C8 guanosine adducts" J. Am. Chern. Soc 2008, 130, 703-709.
Xu, X., et al., "Formation of tricyclic[4.3.3.0] adducts between 8-oxoguanosine and tyrosine under conditions of oxidative DNA-protein cross-linking" Journal of American Chemical Society. vol. 130(31), pp. 10080-10081 (Aug. 6, 2008).

(56) References Cited

OTHER PUBLICATIONS

Zhang, B. et al. "Bench-top method for fabricating glass-sealed nanodisk electrodes, glass nanopore electrodes, and glass nanopore membranes of controlled size" Anal Chem. 2007, 79, 4778-4787.

Zhang, G. et al., "The nanopore electrode" Anal. Chern. 2004, 76, 6229-6238.

Zhou, X., et al., "Quantification of DNA strand breaks and abasic sited by oxime derivatization and accelerator mass spectrometry: application to y-radiation and peroxynitrite" Analytical Biochemistry. vol. 343(1), pp. 84-92 (Aug. 1, 2005).

Cadet et al. "UVB and UVA radiation-mediated damage to isolated and cellular DNA" Pure Appl. Chem., vol. 77, No. 6, pp. 947-961, 2005.

Folkmann et al. "Oxidatively Damaged DNA in Rats Exposed by Oral Gavage to C60 Fullerenes and Single-Walled Carbon Nanotubes" Environmental Health Perspectives, vol. 117, No. 5, May 2009.

Schibel, A. et al., "Nanopore detection of 8-oxo-7,8-dihydro-2'-deoxyguanosine in immobilized single-stranded DNA via adduct formation to the DNA damage site," Journal of the American Chemical Society, vol. 132, No. 51, Dec. 2010, pp. 17992-17995.

Singer, A., et al., "Nanopore based sequence specific detection of duplex DNA for genomic profiling," Nano letters, vol. 10, No. 2, Feb. 2010, pp. 738-742.

An, N. et al., "Crown etherelectrolyte interactions permit nanopore detection of individual DNA abasic sites in single molecules," Proceedings of the National Academy of Sciences ofthe United States of America, vol. 109, No. 29, Jul. 2012, pp. 11504-11509.

Search Report from the United Kingdom Intellectual Property Office for Application No. 1216007.3 dated Apr. 19, 2013 (4 pages).

United States Patent Office Action for U.S. Appl. No. 13/227,212 dated Aug. 8, 2014 (23 pages).

United States Patent Office Notice of Allowance for U.S. Appl. No. 13/227,212 dated Nov. 21, 2014 (7 pages).

\* cited by examiner

C$_{40}$-Btn     5'-CCCCCCCCCC CCCCCCCCCC CCCCCCCCCC CCCCCCCCCC-Btn
(SEQ ID NO:1)
C$_{39}$G$_{\omega 14}$-Btn    5'-CCCCCCCCCC CCCCCCCCCC CCCCCCGCCC CCCCCCCCCC-Btn
(SEQ ID NO:2)
C$_{38}$G$_{\omega 13,14}$-Btn   5'-CCCCCCCCCC CCCCCCCCCC CCCCCCGGCC CCCCCCCCCC-Btn
(SEQ ID NO:3)
C$_{39}$OG$_{\omega 14}$-Btn   5'-CCCCCCCCCC CCCCCCCCCC CCCCCC(OG)CCC CCCCCCCCCC-Btn
(SEQ ID NO:4)
FIG. 14
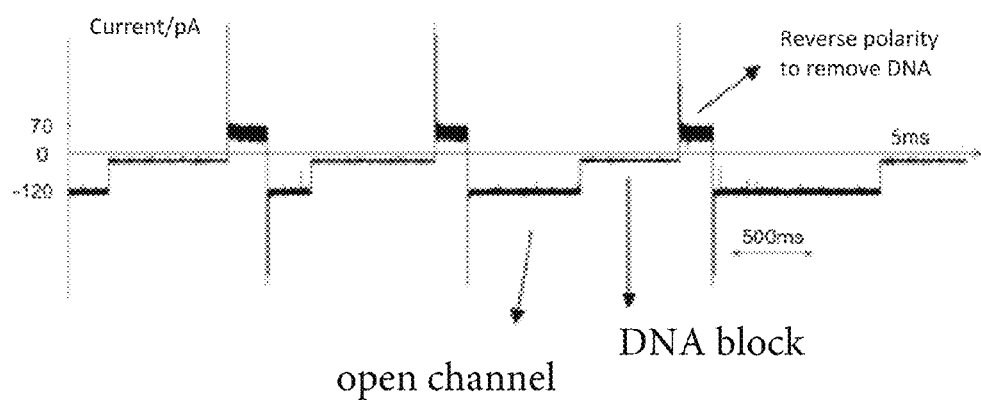
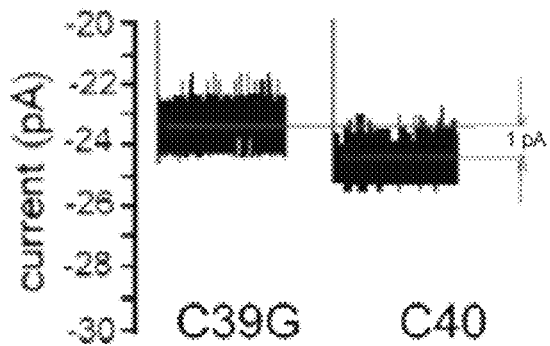
FIG. 15

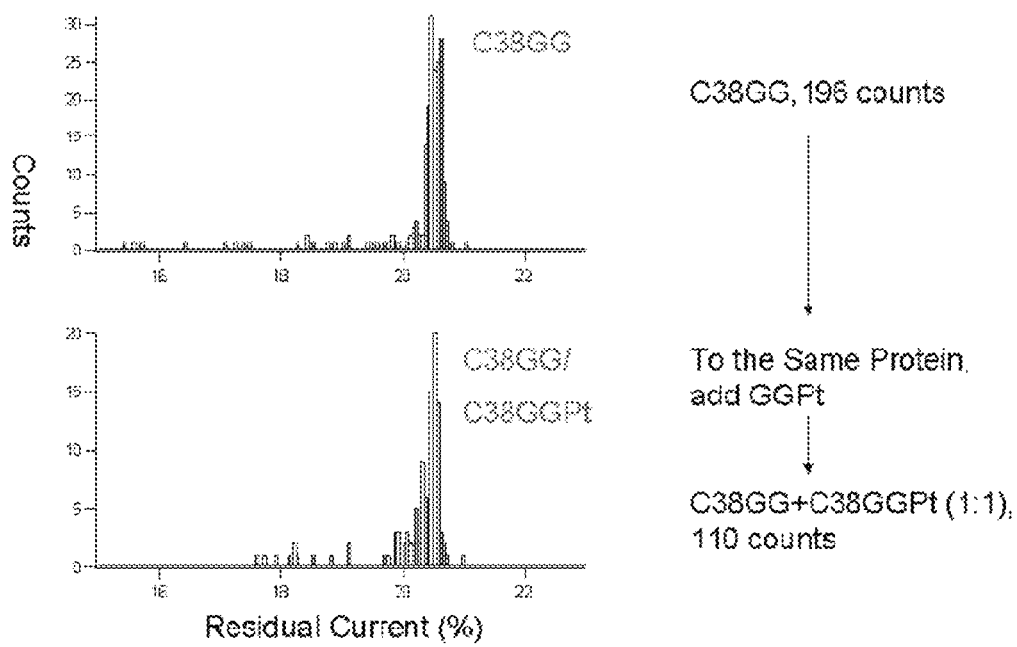
FIG. 26
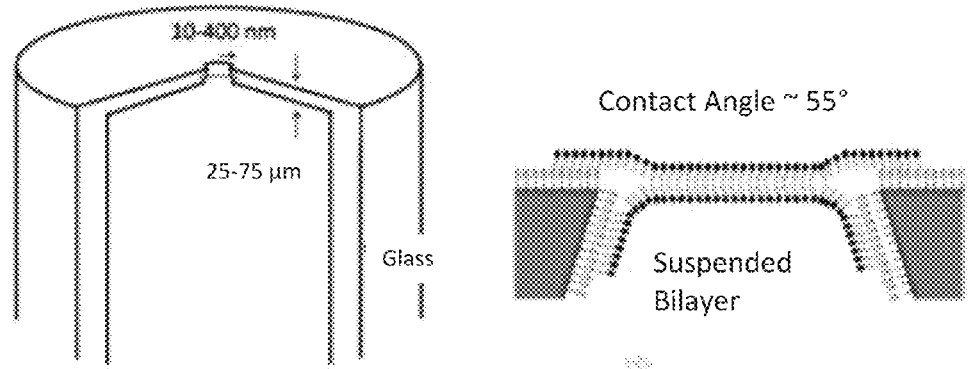
FIG. 27
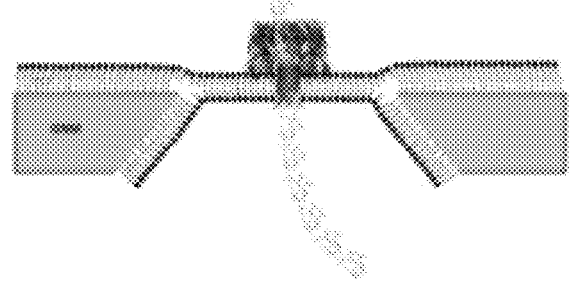

C₄₀-Btn 5'- CCCCCCCCCC CCCCCCCCCC CCCCCCX₍ₙ₋₁₄₎CCC CCCCCCCCCC -Btn (SEQ ID NO:9)

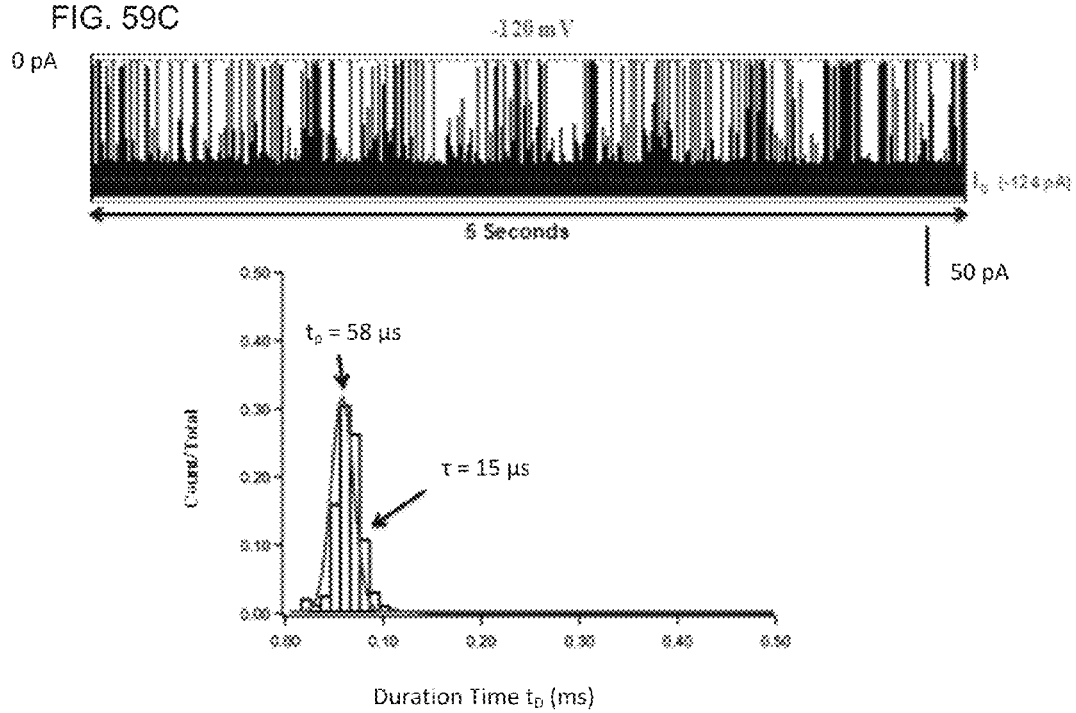
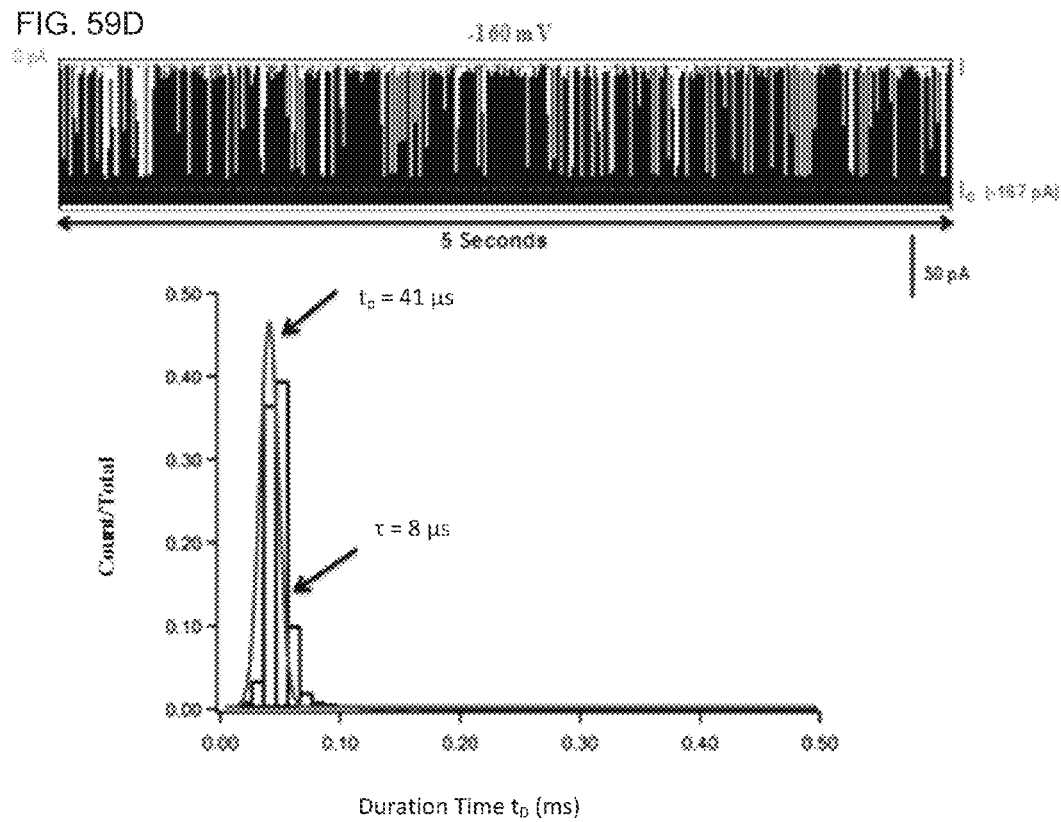

Translocation conditions:
100 kHz, -120 mV, 1 M NaCl

3' entry

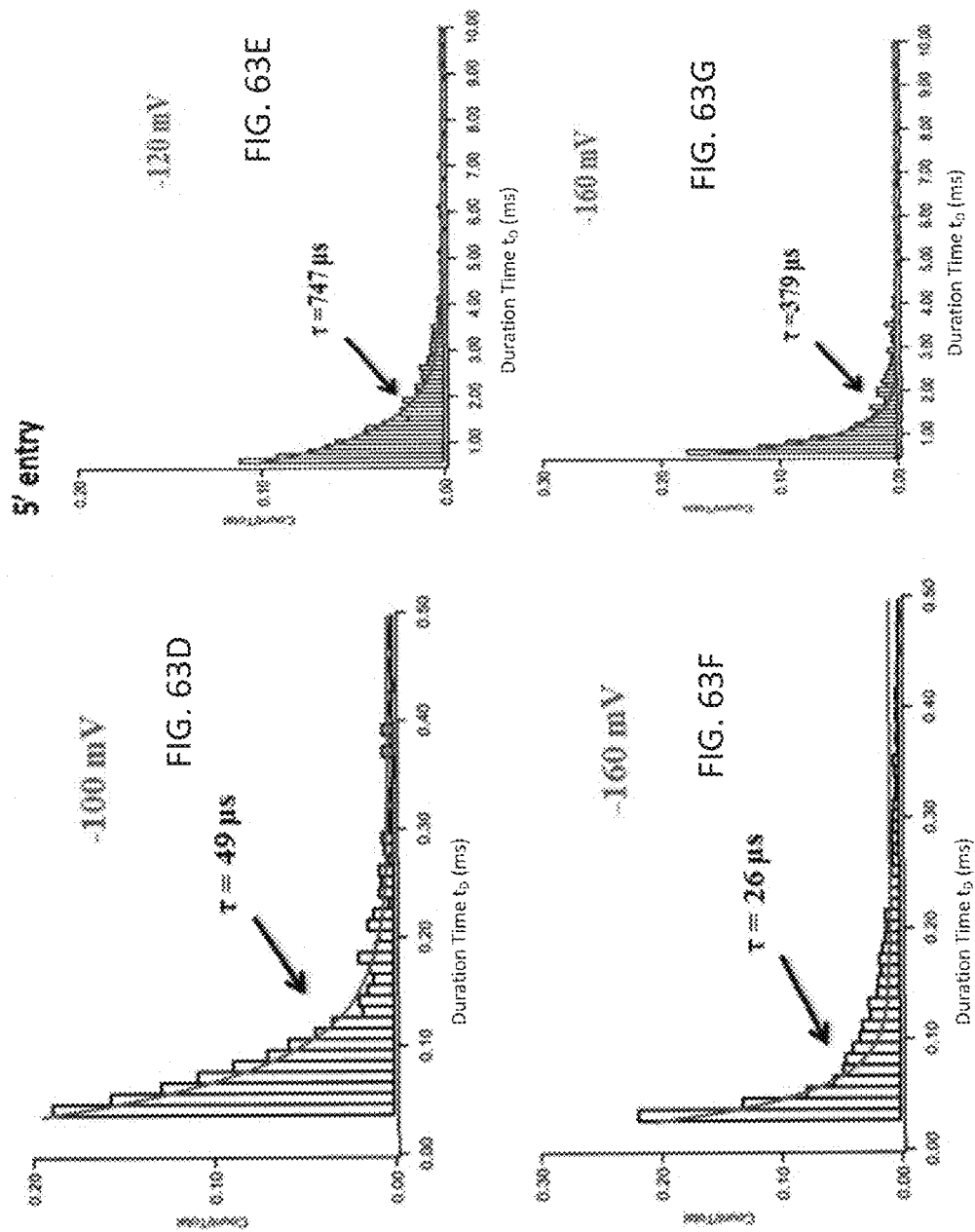

BTN – CCCCCCCCCC CCCCCCCCC CCCCCCXCCC CCCCCCCCC 5'
(SEQ ID NO:11)

DETECTION OF NUCLEIC ACID LESIONS AND ADDUCTS USING NANOPORES

CROSS REFERENCE TO RELATED APPLICATIONS

This application is a divisional of U.S. application Ser. No. 13/227,212, filed Sep. 7, 2011, which is a continuation-in-part application of International Patent Application No. PCT/US2011/027433, filed Mar. 7, 2011, which claims the benefit of priority to U.S. Provisional Application No. 61/310,822, filed Mar. 5, 2010. U.S. application Ser. No. 13/227,212 also claims the benefit of priority to U.S. Provisional Application No. 61/455,829, filed Oct. 27, 2010. The disclosures of all of these applications are incorporated by reference herein in their entireties. Priority to each application is hereby claimed.

GOVERNMENT INTEREST

This invention was made with government support under R01 HG005095 awarded by the National Institutes of Health, CHE0514612 awarded by the National Science Foundation, HSHQDC-09-C-00091 awarded by the U.S. Department of Homeland Security, and FA9550-06-C-0060 awarded by the USAF/AFOSR—Air Force Office of Scientific Research. The government has certain rights in the invention.

SEQUENCE LISTING

The application contains a Sequence Listing which has been submitted as a computer readable format (ANSI Text format) via EFS-Web and is hereby incorporated by reference. The Sequence Listing was created on Dec. 22, 2011, is named 026389-9035-US01_SeqList_ST25.txt, and is 4,784 bytes in size.

BACKGROUND

Exposure of DNA to carcinogens, radiation, oxidation agents or other agents can damage base pairs. Such damage can ultimately lead to cell apoptosis or tumor growth. Detection and diagnosis of such damage could potentially lead to treatments and/or preventative measures. However, methods for detecting such damage are limited. Conventional methods for detecting specific DNA damage include: (I) DNA digestion followed by LC-MS analysis and (2) gel electrophoretic analysis of primer extension studies. The first method is widely employed but requires substantial chemical and enzymatic manipulation that may introduce artifacts. In addition, no sequence information is gained, and the sensitivity is limited. In the second method, the sequence of the area of the genome of interest must already be known, and the sensitivity is also limited. A third method for assessing global DNA damage is the "comet assay". Although widely employed to analyze generic DNA damage, it does not provide any information on either the type or location of the lesions.

SUMMARY

Methods, systems, and compounds for detecting modified nucleic acid bases is disclosed and described. In one aspect, for example, a method of detecting a nucleic acid lesion can include directing a strand of DNA or RNA containing a nucleic acid adduct into a channel, the nucleic acid adduct including a nucleic acid having a lesion and a current modulating compound coupled to the nucleic acid at the lesion, and measuring changes in current through the channel in response to the current modulating compound to detect the lesion. The current may be ionic or electronic current through the nanopore that is sensitive to the structure or presence of the modulating compound. In some cases, the method can include forming the nucleic acid adduct. Additionally, the method can optionally include coupling an immobilization compound to the nucleic acid adduct, where the immobilization compound functions to preclude the translocation of the nucleic acid adduct completely through the channel. In some cases, the current modulating compound itself is of sufficient size to preclude the complete translocation of the nucleic acid adduct through the channel. Alternatively, directing the DNA strand with a nucleic acid adduct into the channel further includes translocating the nucleic acid adduct through the channel.

Various covalent and noncovalent chemical modifications of nucleic acids are contemplated. For example, the current modulating compound can optionally be coupled to the nucleic acid at an abasic site associated with the lesion. In some cases, the current modulating compound can be a primary amine Non-limiting examples of current modulating compounds can include alkanes, alkenes, alkynes, aryls, sugars, carbohydrates, azides, halides, amines, imines, peptides, crown ethers, metal-binding ligands, transition metal complexes, and the like, including combinations thereof. Other non-limiting examples of current modulating compounds include crown ethers (e.g. 18-crown-6 and 15-crown 5), metal ion binding ligands (e.g. EDTA and its derivatives), metal-binding polyamines (e.g. cyclam, cyclen, and DOTA) and peptides or peptide derivatives (e.g. Sal-XH peptides[3]) or related metal chelates that undergo interactions with metal ions present in an electrolyte such that conformational changes in the metal chelate lead to modulations in current level or translocation time through the ion channel.

In some cases the current modulating compound can be introduced into the nucleic acid via an 8-oxoG intermediate. In other cases the current modulating compound can be introduced into the nucleic acid adduct via an aldehyde intermediate. In yet other cases the current modulating compound can be introduced into the nucleic acid adduct via a platination intermediate.

A variety of lesions are contemplated that can be detected or used for the formation of a nucleic acid adduct, and any such lesion is considered to be within the present scope. Non-limiting examples include uracil in DNA, 8-oxoG, 1,$N^6$-ethenoadenine, and the like, including combinations thereof. Other non-limiting examples of reactions that result in lesions can include depurination, deamination, cyclobutane photodimer generation, alkylation, oxidation, and the like, including combinations thereof.

In another aspect, a method of obtaining DNA or RNA sequence information from a nucleic acid is provided. Such a method includes reacting a current modulating compound with a nucleic acid to selectively couple the current modulating compound to a preselected nucleotide type, where the current modulating compound and the nucleic acid thus form a nucleic acid adduct. Alternatively, embodiments relate to merely providing a nucleic acid adduct. The method also includes directing the nucleic acid adduct into a channel and measuring changes in current through the channel in response to the current modulating compound to detect the preselected nucleotide type.

Various reaction chemistries capable of incorporating a current modulating compound into a nucleic acid are contemplated. Non-limiting examples include oxidation reactions, alkylation reactions, platination reactions, deamination reactions, halogenations reactions, depurination/depyrimidination reactions, and the like, including combinations thereof. As one example, reacting the current modulating compound with the nucleic acid includes bromination of cytosine. In another example, reacting the current modulating compound with the nucleic acid includes reacting the nucleic acid with cis-platin. In yet another example, reacting the current modulating compound with the nucleic acid includes forming a lesion in the nucleic acid and coupling the current modulating compound to the lesion to form the nucleic acid adduct. In some cases the lesion is an abasic site. Furthermore, in some cases the current modulating compound is a plurality of current modulating compounds coupled exclusively to nucleic acid bases of the preselected nucleic acid type.

In some cases, measuring changes in current through the channel in response to the current modulating compound to detect the preselected nucleotide type can optionally include measuring multiple current modulating compounds and correlating the multiple current modulating compounds to a sequence of the nucleic acid. Additionally, in some cases the multiple current modulating compounds are associated with adjacent nucleotide bases. Alternatively, the multiple current modulating compounds are associated with adjacent nucleotide bases on different nucleic acid molecules having the same sequence.

Nucleic acid adducts are also provided. Such an adduct includes a nucleic acid having a damaged region and a current modulating compound coupled to the damaged region. In some embodiments a nucleic acid adduct comprises a modified nucleotide type, wherein the modified nucleotide type comprises a current modulating compound. Non-limiting examples of general categories of current modulating compounds include alkanes, alkenes, alkynes, aryls, sugars, carbohydrates, azides, halides, amines, imines, peptides, crown ethers, metal-binding ligands, transition metal complexes and the like, including combinations thereof. Additionally, in some cases the damaged region is an abasic site.

A system for detecting a current modulating compound is also provided. Such a system can include a membrane including a conical nanopore having an opening with a suspended lipid bilayer across the opening, a pair of electrodes configured to register changes in electrical current across the opening, and a nucleic acid adduct of a nucleic acid and a current modulating compound located within the nanopore. In some cases, the suspended lipid bilayer includes a protein embedded therein to form a channel such that transport of the nucleic acid adduct across the channel is inhibited while transport of non-adduct nucleic acid is not substantially inhibited.

A method of using current modulating compounds as registration markers is also provided. Such a method can include detecting a current modulation compound, thus registering the identity and location of the current modulation compound and thus termed a registration marker. In embodiments, the method further comprises using registration markers to measure or read at least a portion of a nucleic acid multiple times. In certain embodiments, the multiple measurements of the nucleic acid can improve sequencing accuracy and/or help to identify nucleotide repeats.

A method of identifying and determining the number of nucleotide repeats within a nucleic acid strand is provided. This method comprises coupling at least one current modulating compound to a nucleotide that is adjacent to the same type of nucleotide and measuring multiple nucleic acid strands of the same sequence. In embodiments, the method further comprises determining the number of base repeats based on the multiple measurements.

Thus, in an aspect, the disclosure provides a method of obtaining sequence information from a nucleic acid comprising providing at least one nucleic acid adduct, wherein the at least one nucleic acid adduct comprises a nucleotide type coupled with a current modulating compound; directing the nucleic acid into a channel, wherein the channel comprises an initial current in the absence of the nucleic acid; measuring the current as the nucleic acid is in the channel; detecting the current modulating compound in the channel; registering the identity and location of the current modulating compound on the nucleic acid; and assigning the current modulating compound as a first registration marker on the nucleic acid, wherein the first registration marker provides an detectable reference point in the sequence of the nucleic acid.

In another aspect the disclosure provides a method of assigning a registration marker within a nucleic acid comprising providing at least one nucleic acid adduct, wherein the at least one nucleic acid adduct comprises a nucleotide type coupled with a current modulating compound; directing the nucleic acid into a channel, wherein the channel comprises an initial current in the absence of the nucleic acid; measuring the current as the nucleic acid is in the channel; detecting the current modulating compound in the channel; registering the identity and location of the current modulating compound on the nucleic acid; and assigning the current modulating compound as a first registration marker on the nucleic acid.

In embodiments of the above two aspects the methods can further comprise a nucleic acid that includes at least a second nucleic acid adduct that comprises a second nucleotide type coupled with a second current modulating compound; detecting the second current modulating compound in the channel; registering the identity and location of the second current modulating compound on the nucleic acid; and assigning the second current modulating compound as a second registration marker on the nucleic acid; and wherein the second registration marker is detected while measuring at least a portion of the nucleic acid.

In yet another aspect the disclosure provides a method for identifying the number of repeat nucleotides in at least a portion of a nucleic acid strand comprising a) providing at least one nucleic acid adduct in a first nucleic acid strand, wherein the at least one nucleic acid adduct comprises a first nucleotide type coupled with a current modulating compound, and wherein the first nucleotide type is adjacent to at least a second nucleotide type wherein the first and second nucleotide type is the same; b) directing the nucleic acid into a channel, wherein the channel comprises an initial current in the absence of the nucleic acid; c) measuring the current as the nucleic acid translocates the channel; d) detecting the current modulating compound; e) repeating steps a)-d) at least a second time with at least a second nucleic acid strand wherein the first and second nucleic acid strands comprise the same sequence; and f) determining the number of repeat nucleotides in the sequence of the first and second nucleic acid strand by combining data obtained from steps c) and d).

There has thus been outlined, rather broadly, the more important features of the invention so that the detailed description thereof that follows may be better understood, and so that the present contribution to the art may be better appreciated. Other features of the present invention will become clearer from the following detailed description of the invention, taken with the accompanying drawings and claims, or may be learned by the practice of the invention.

BRIEF DESCRIPTION OF THE DRAWINGS

FIG. 14 is a schematic depiction of oligonucleotides (SEQ ID NOS 1-4) employed in channel experiments in accordance with an embodiment of the present invention;

FIG. 15 shows an i-t trace corresponding to the capture of the straptavidin-biotin DNA complex containing both $C_{40}$ and $C_{39}G_{\omega 14}$ oligomers in accordance with an embodiment of the present invention;

FIG. 26 shows data representing a control study on residual currents of $C38GG_{\omega 13,14}$ and mixed $C38GG_{\omega 13,14}/C38GG_{\omega 13,14}$Pt in accordance with an embodiment of the present invention;

FIG. 27 is a schematic diagram of a glass nanopore membrane (GNM) in accordance with an embodiment of the present invention;

FIGS. 59A-D show example traces and individual duration histograms in translocation studies for poly-$dC_{87}$ and $t_D$ histogram under different voltages (FIG. 59A is −80 mV, FIG. 59B is −100 mV, FIG. 59C is −120 mV, and FIG. 59D is −160 mV) in accordance with an embodiment of the present invention.

FIGS. 63A-G show example traces and individual duration histograms in translocation studies of poly-$dC_{43}$[18-crown-6]$dC_{43}$ (SEQ ID NO:10) and $t_D$ histogram under different voltages.

Figure 1:
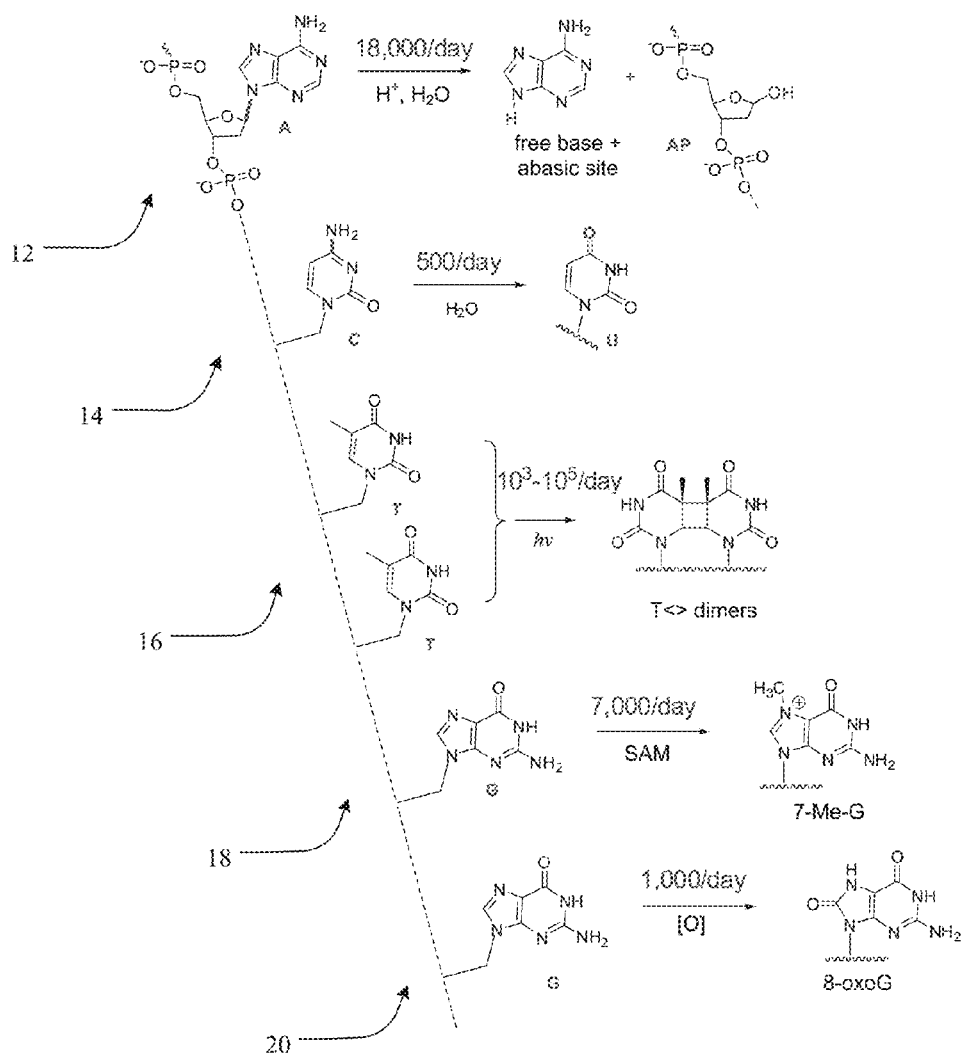
FIG. 1 is a schematic depiction of various damaging chemistries occurring in DNA in accordance with an embodiment of the present invention.

It will be understood that the above figures are merely for illustrative purposes in furthering an understanding of the invention. Further, the figures are not drawn to scale, thus dimensions, particle sizes, and other aspects may, and generally are, exaggerated to make illustrations thereof clearer. Therefore, departure can be made from the specific dimensions and aspects shown in the figures in order to produce the heat spreaders of the present invention.

DETAILED DESCRIPTION

While these exemplary embodiments are described in sufficient detail to enable those skilled in the art to practice the invention, it should be understood that other embodiments may be realized and that various changes to the invention may be made without departing from the spirit and scope of the present invention. Thus, the following more detailed description of the embodiments of the present invention is not intended to limit the scope of the invention, as claimed, but is presented for purposes of illustration only and not limitation to describe the features and characteristics of the present invention, to set forth the best mode of operation of the invention, and to sufficiently enable one skilled in the art to practice the invention. Accordingly, the scope of the present invention is to be defined solely by the appended claims.

DEFINITIONS

In describing and claiming the present invention, the following terminology will be used.

The singular forms "a," "an," and "the" include plural referents unless the context clearly dictates otherwise. Thus, for example, reference to "a strand" includes reference to one or more of such materials and reference to "subjecting" refers to one or more such steps.

As used herein, a "current modulating compound" refers to any compound or molecule that, when coupled to a nucleic acid, modulates current flow through a channel when the current modulating compound is present in the channel, as compared to the same nucleic acid without the current modulating compound. Such modulation can include changes in current flow (e.g. current decrease or increase) as well as changes in the duration of current variation due to the current modulating compound translocating into or through the channel. Additionally, "current modulating compound" can refer to the compound that is reacted with the nucleic acid to form the adduct as well as to the resulting nucleic acid modification following incorporation into the nucleic acid.

As used herein, "nucleotide type" refers to a specific moiety of nucleotide including A, C, T, G, and U, as well as naturally occurring modified nucleotide bases such as 5-methyl-C, and modified nucleotide bases resulting from DNA damage processes (oxidation, alkylation, deamination, formation of abasic sites, and the like) or treatment of DNA or RNA with modifying agents including drugs, such as, for example, agents for platination, alkylation, oxidation, or the like. In RNA, "nucleotide type" can additionally refer to any of the common modifications such as those found in tRNAs including methylated base and sugar moieties. Additionally, "nucleotide type" can also refer to multiple bases in a sequence, such as G-G, G-G-G, G-A-C, T-A-T-A, C-C, and the like.

As used herein with respect to an identified property or circumstance, "substantially" refers to a degree of deviation that is sufficiently small so as to not measurably detract from the identified property or circumstance. The exact degree of deviation allowable may in some cases depend on the specific context.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a numerical range of about 1 to about 4.5 should be interpreted to include not only the explicitly recited limits of 1 to about 4.5, but also to include individual numerals such as 2, 3, 4, and sub-ranges such as 1 to 3, 2 to 4, etc. The same principle applies to ranges reciting only one numerical value, such as "less than about 4.5," which should be interpreted to include all of the above-recited values and ranges. Further, such an interpretation should apply regardless of the breadth of the range or the characteristic being described.

Any steps recited in any method or process claims may be executed in any order and are not limited to the order presented in the claims. Means-plus-function or step-plus-function limitations will only be employed where for a specific claim limitation all of the following conditions are present in that limitation: a) "means for" or "step for" is expressly recited; and b) a corresponding function is expressly recited. The structure, material or acts that support the means-plus function are expressly recited in the description herein. Accordingly, the scope of the invention should be determined solely by the appended claims and their legal equivalents, rather than by the descriptions and examples given herein.

Disclosure

Techniques for detecting nucleic acid modifications using nanopore technology are provided. Such technology can be implemented for a variety of investigational uses, including, without limitation, detecting damage or lesions in nucleic acids, sequencing nucleic acids, epigenetics, obtaining general sequence information from a nucleic acid (e.g., using the current modulating compounds as registration markers and determining the number of base repeats as described herein), and the like. It should be noted that, while various discussion points are made below regarding one or more of such uses, any disclosure described in relation to a given use that can be applied to any other use would also be considered to be within the present scope. For example, discussions relating to DNA lesion analysis should be taken as also relating to other uses where applicable, such as sequence analysis. Similarly, discussions directed to a particular nucleic acid adduct, such as, for example, an adduct associated with a DNA lesion, should be applied to nucleic acid sequencing where applicable.

Regarding nucleic acid damage, a method for detecting nucleic acid lesions through the formation of nucleic acid adducts that modulate current flow through a nanopore as the adduct is translocating into or through the pore, is disclosed and described. The method is based on the use of a nanopore through which single-stranded and double stranded nucleic acids and nucleic acid adducts can be translocated in an applied electric field. A "nucleic acid" can be comprised of DNA and RNA molecules including DNA and RNA monomers or polymers that are single stranded or double-stranded and are comprised of at least one nucleotide type. The rate of translocation depends in part on the size of the nucleic acid adduct passing through the nanopore. In certain embodiments, the nanopore is less than 1,000 nm in diameter at the smallest contriction point (e.g. less than 1,000, 900, 800, 700, 600, 500, 400, 300, 200, 100, 90, 80, 70, 60, 50, 40, 30, 20, 10, 9, 8, 7, 6, 5, 4, 3, 2, or 1 nm). Covalent adducts are made to nucleic acid lesions such as 8-oxoguanosine, a common biomarker of oxidative damage in DNA. Examples of the molecules adducted are primary amines including benzyl amine, lysine, arginine, spermine, spermidine, and an amine derivative of β-cyclodextrin. When the adduct is sufficiently large (e.g. β-cyclodextrin), the nanopore is completely blocked, allowing detection and identification of the position of the lesion. Smaller adducts modulate the ion flow as DNA translocates through the nanopore, also allowing detection and identification of the position of the lesion. This method allows analysis of human tissue samples to evaluate oxidative stress and other forms of damage in an extremely sensitive method. It can aid researchers interested in oxidative stress, mutagenesis and disease, and in medical diagnostics.

Genomic and mitochondrial DNA bases undergo continuous modifications as a result of both natural processes that introduce epigenetic markers (5-methylC), as well as exposure to DNA damaging agents through oxidation and alkylation reactions from endogenous sources or toxicants. DNA sequencing techniques may not directly detect DNA damage because the sequencing takes place on PCR-amplified strands that perforce contain only the 4 canonical bases A, C, T, and G. Mutations and SNPs (single-nucleotide polymorphisms) can be detected by sequencing, and many of these are the ultimate outcome of DNA damage. However, mutations themselves do not provide much information about the chemical identity of the original damage. Understanding the molecular origins of DNA mutations can be a key to preventative medicine for cancer, toxicology, and age-related disorders. Approaches for the detection of nucleotide modifications such as DNA base modifications (e.g. oxidation, alkylation, excision, and the like) by application of chemical and enzymatic methods to convert the modified base to an adduct that yields a detectable signal when individual nucleic acid strands translocate through a membrane-embedded ion channel are provided. In addition, the present scope also includes nucleic acid modifications purposefully introduced into the nucleic acid for the purposes of sequencing and/or sequence analysis or other qualitative investigation of sequence information.

In the case of DNA, for example, DNA strands from each cell are estimated to undergo tens of thousands of base modification reactions per day, the vast majority of which are corrected by DNA repair enzymes before replication or transcription occurs. Under conditions of stress, DNA bases can be damaged beyond the capability of the repair system, leading to cell death (apoptosis) or worse, to immortalization and cancer, as well as aging, neurodegenerative, and cardiovascular diseases. It is possible that multiple damage occurrences in the same cell are the most efficacious in leading to disease states; however, there appear to be no methods in place for single-molecule analysis of DNA damage.

A variety of common damaging chemistries occur with the DNA bases, a few of which are shown in FIG. 1 and in the description that follows. Depurination 12 is a damaging reaction that results in the loss of an adenine or guanine base, thus resulting in an abasic site (e.g. AP=apurinic or apyrimidinic) on the DNA strand. Depurination is mediated by acidic conditions or certain base alkylating agents or platination with compounds such as cis-platin.

The hydrolytic conversion of an exocyclic amino group to a keto group, or deamination 14, occurs in enzyme-catalyzed RNA editing, and also represents a naturally occurring form of DNA damage that can be mutagenic. In the case of C, the deamination of C is a reaction that generates U, which would code as a T if unrepaired. Deamination is catalyzed not only by acidic conditions, but also by exposure to nitrosating agents such as nitrosamines.

Cyclobutane photodimers 16, such as T< >T shown in FIG. 1, are formed upon exposure to UV light and are primary lesions leading to skin cancers. Their formation is variable depending on the amount of light exposure and the wavelength of light.

Alkylation 18 reactions (e.g. methylation) of bases occurs when DNA undergoes epigenetic marking, as in the conversion of C to 5-MeC by an enzyme catalyzed reaction that utilizes S-adenosylmethionine (SAM). Mismethylation is one example of DNA damage (see FIG. 2 for G methylation at N7). Another major source of alkylation is exposure to electrophilic agents such as aldehydes generated from lipid peroxidation, environmental alkylating agents (vinyl chloride, acrylates, etc.) or treatment with anticancer agents such as mitomycin or chlorambucil. Cis-platin also generates a G-N7 adduct or cross-link, and though not technically an alkylating agent, this antitumor drug bears some similarity to DNA alkylating agents.

Oxidative damage 20 to DNA bases (e.g. G→8-oxoG) may be a leading cause of age-related disorders including cancer, and may also play a role in metabolic disorders. Oxidative damage frequently occurs to guanine, often leading to the formation of 8-oxoG, which is a possible biomarker of oxidative stress in the cell. Levels of 8-oxoG are elevated during chronic infection, high metabolic stress, abnormal utilization of redox active metals such as Fe and Cu, and after reperfusion injury. A suite of DNA repair enzymes seek out 8-oxoG and related lesions to correct this damage before it leads to mutation. Lack of repair of 8-oxoG leads to G-to-T mutations; a single G-to-T mutation in codon 12 of the HRAS gene, for example, may be a factor in the development of bladder cancer.

Figure 2:
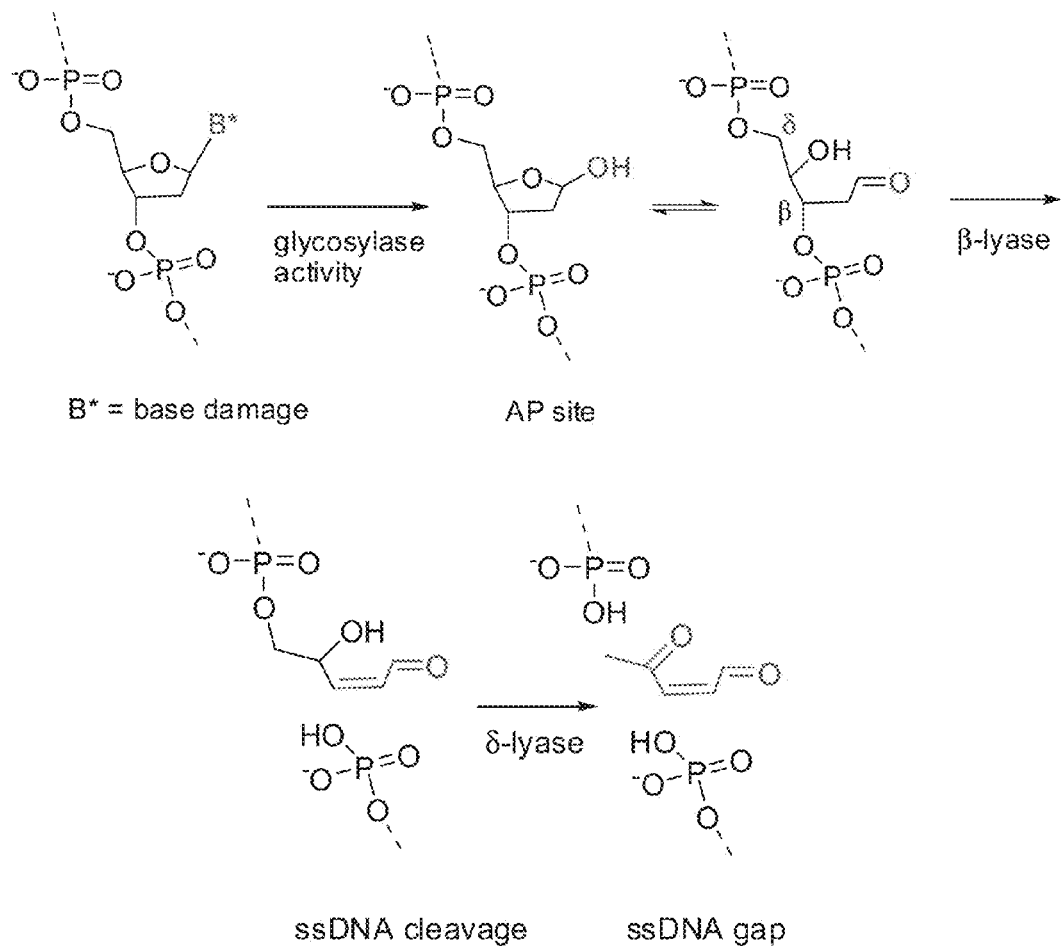
FIG. 2 is a schematic depiction of abasic site chemistry in accordance with an embodiment of the present invention.

DNA base damage is detected and corrected in the cell via multiple mechanisms, one pertinent to the above examples being base excision repair (BER). In this mechanism, a BER glycosylase first scans the duplex for non-canonical bases and cleaves the glycosidic bond, thus generating an abasic (AP) site. As is shown in FIG. 2, BER enzymes cleave the glycosidic bond to create an AP site. Some BER enzymes also have β-lyase or β,δ-lyase activity and create a strand break; others rely on a downstream enzyme such as AP endonuclease to cleave out the remaining ribose unit before other enzymes resynthesize the strand using the undamaged base opposite as a template. In addition to natural processes, enzymes such as BER can be used to for the generation of AP sites in DNA for the purpose of creating a nucleic acid adduct. For example, DNA damage can be introduced by any of a variety of damaging mechanisms, then enzymatically converted to an AP site for further chemical processing into an adduct.

Figure 3:
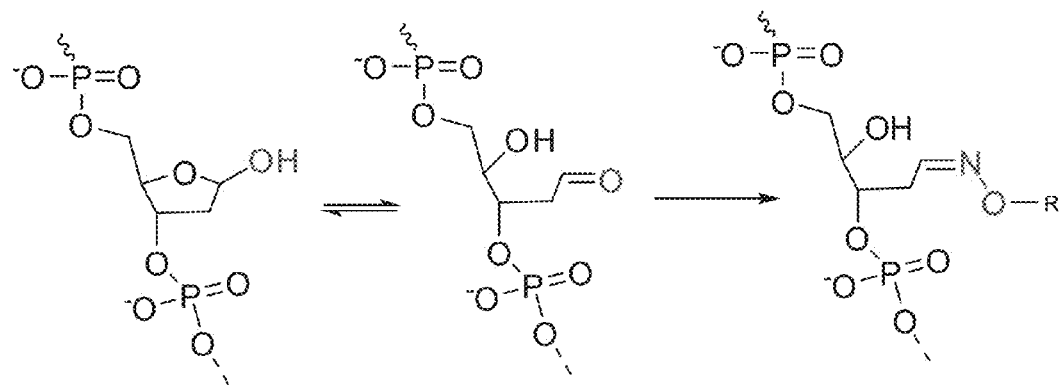
FIG. 3 is a schematic depiction of functionalization of an abasic site in accordance with an embodiment of the present invention.

As has been described, AP sites can be utilized to form nucleic acid adducts. This includes nucleic acids containing AP sites generated in vivo and nucleic acids containing AP sites generated in vitro. DNA AP tautomerizes between ring-closed form and ring-open aldehyde form, the existence of which allows AP to be further functionalized. While any technique for forming an adduct is considered to be within the present scope, in one aspect, an AP site can be functionalized to create an adduct by coupling a current modulating compound at the aldehyde site, as is shown in FIG. 3. As is more fully described below, a current modulating compound can be introduced at the aldehyde site to create a nucleic acid adduct. It should be noted that various chemistries can be used to incorporate a current modulating compound at an AP site of a nucleic acid, and as such, any chemistry that allows such incorporation via an AP site is considered to be within the present scope.

Figure 61:
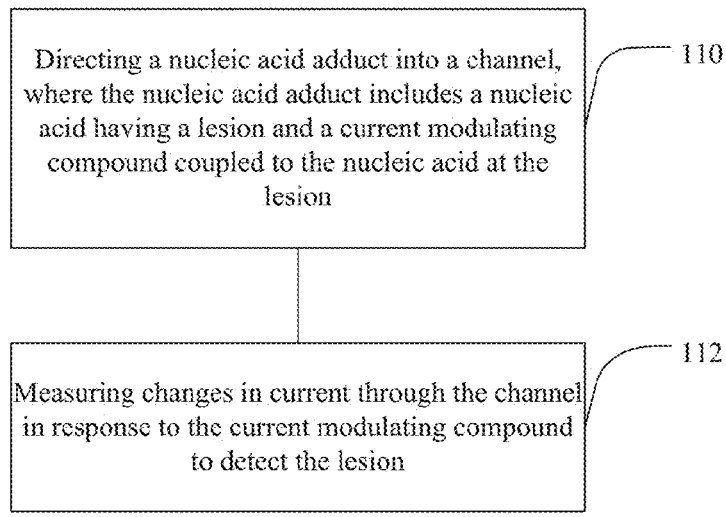
FIG. 61 is a schematic diagram of a method of detecting a nucleic acid lesion in accordance with an embodiment of the present invention.

Accordingly, in one aspect a method of detecting a nucleic acid lesion is provided, as is shown in FIG. 61. Such a method includes directing a nucleic acid adduct into a channel, the nucleic acid adduct including a nucleic acid having a lesion and a current modulating compound coupled to the nucleic acid at the lesion 110, and measuring changes in current through the channel in response to the current modulating compound to detect the lesion 112. In one aspect, the method can include forming the nucleic acid adduct.

Various channels are contemplated into which a nucleic acid adduct can be directed in order to detect current changes associated with the adduct. Generally, any nanopore that is capable of such current detection is considered to be within the present scope. In one aspect, the channel can be a transmembrane protein channel. Non-limiting examples of such protein channels include α-hemolysin (α-HL) channels, the porin MspA of *Mycobacterium smegmatis*, chemical modifications of these proteins and mutant forms of the proteins, and the like. In one specific aspect, the channel is α-HL. In another aspect, the channel can be a manufactured nanopore in a suitable substrate or a solid-state nanopore in a suitable membrane for recording current, such as glass, quartz, sapphire, $SiO_2$, SiN, and diamond. It should be noted that the following discussion directed to α-HL channels should be applied to other channels where applicable. Accordingly, one general non-limiting channel set up would include the channel and a membrane or other support with electrically insulating properties to ensure that current flows at least predominantly through the channel. By placing an electrode on either side of the membrane, current delivered between the electrodes will flow through the channel. The standing open current reading of the channel can be noted, and any change in this current would likely be due to some current impedance within the channel. Thus directing a nucleic acid through the channel will cause a decrease in current flow through the channel as compared to the open current reading. Adducts having different characteristics, such as current modulating compound sizes and/or polarities, will block current to a greater or lesser extent, and thus provide a distinct current signature. An additional method for detecting the adduct is to measure a current, e.g., a capacitive, electrochemical, or tunneling current, transverse to the adducted stranded within the channel or nanopore.

The translocation of single-stranded DNA and RNA through a channel, such as, for example, an α-HL channel, can be used to identify nucleic acid lesions and other damage, as well as providing high-speed and low-cost methods of sequencing polynucleotides via the exploitation of ion channel recordings. The α-HL pore, for example, comprises a vestibule (~2.5 nm diameter cavity) and a stem region (~1.4 nm) that is sufficiently large to allow single-stranded DNA (ss-DNA) to pass through the interior of the pore. Double-stranded DNA (ds-DNA), with a diameter of ~2.2 nm, can enter the vestibule but cannot pass through the more narrow stem region. The electrophoretically-driven translocation of ss-DNA through a solitary wild-type (WT) or modified α-HL channel, reconstituted in an electrically insulating lipid bilayer, is readily detected using ion channel recording methods. As ss-DNA translocates through the pore, the ion channel current decreases to about 90% of the open channel value. Additionally, the duration of the translocation event is a measure of the length of the ss-DNA molecule, although thermal diffusion at room temperature requires averaging of numerous translocation events to obtain precise length values. Ideally, the current vs. time electrical trace recorded during the translocation of an individual ss-DNA molecule exhibits four distinct levels, each level corresponding to one of the four bases (adenine (A), thymine (T), guanine (G), and cytosine (C)). In principle, as the DNA molecule translocates the channel, the electrical readout of the four current levels provides the nucleotide sequence.

One limitation that presents itself is that available electronics are insufficiently sensitive to reliably capture the electronic signature of each base. This limitation is largely associated with the rapid translocation rate of DNA and RNA through WT-α-HL (1-20 μs per base) at typical bias voltages (~100 mV), which requires MHz bandwidth and data acquisition, coupled with the very small variations in channel current for the different nucleotides passing through the constriction zone of α-HL. Although measurable, the difference in ion current for different DNA homopolymers is only on the order of a few pA. Larger differences in the signal identifying the nucleotide can be achieved by modifying the bases with bulky adducts Immobilization of DNA within the channel, using a terminal hairpin or biotin-streptavidin complex to prevent passage of the DNA through the nanopore, allows time averaging of the current, resulting in sharply defined current distributions for each nucleotide. Reducing the translocation velocity of DNA through the nanopore in order to obtain increased signal-to-noise, either by reducing the temperature or increasing the solution viscosity, has been demonstrated, but these methods also tend to reduce the channel conductance, thus offsetting the advantage of measuring the current for each nucleotide over a longer time. An alternative solution to improving base recognition is to use a DNA polymerase to ratchet ss-DNA one base at a time through the channel. The electrophoretic capture of short hairpin DNA molecules in the α-HL lumen, and subsequent identification of the terminal bases, has also been demonstrated, although this does not provide sequence information.

As has been described, other biological and solid-state channels can be utilized that have internal geometries and dimensions that are more sensitive to the nucleotide base structure. For instance, the porin MspA of *Mycobacterium smegmatis* has a short and narrow channel constriction that may be used for DNA sequencing.

It should be noted that the present disclosure includes situations whereby the nucleic acid adduct blocks the channel and is prevented from translocating, and situations whereby the nucleic acid adduct is translocated through the channel to the other side of the membrane. As such, in one aspect, the method can further include coupling an immobilization compound to the nucleic acid adduct, where the immobilization compound functions to preclude translocation of the nucleic acid adduct completely through the channel. In another aspect, directing the nucleic acid adduct into the channel further includes translocating the nucleic acid adduct through the channel. The present method also includes immobilization of DNA within the channel, using an immobilization compound such as, for example, a terminal hairpin or biotin-streptavidin complex to prevent passage of the DNA through the nanopore, allowing detection of adducted nucleotides.

In addition, high-frequency noise in single channel electrical measurements is associated with the combined inherent noise of the ion channel, thermal diffusion, and the capacitance of the bilayer/support structure. In one aspect, novel support structures can be used to reduce such noise. In one specific aspect, for example, a membrane made of glass and/or fused quartz can be used. In on non-limiting example, such a membrane can have a ~400 nm radius conical shaped nanopore as a support structures for lipid bilayers and ion channel recordings. Details regarding such membranes and manufacture thereof can be found in U.S. patent application Ser. No. 11/743,536, filed on May 2, 2007, U.S. patent application Ser. No. 11/852,061, filed Sep. 7, 2007, and U.S. patent application Ser. No. 12/827,503, filed Jun. 30, 2010, which are each incorporated herein by reference. The small area of the bilayer in which the protein ion channel is embedded and use of such fused quartz membranes reduces the bilayer/support capacitance to very small values, thus allowing increased acquisition rates. It should be noted that, while membranes of particular materials and having conical shaped nanopores are disclosed, any suitable membrane and/or nanopore structure or material that can be used to support the channel is considered to be within the present scope.

Additionally, alternating current (AC) phase-sensitive detection can be used to measure the conductance of the ion channel, while simultaneously applying a DC bias to electrostatically control the binding affinity and kinetics of charged molecules. A low amplitude AC signal (~10 mV rms) allows the protein-DNA interaction to be measured in the absence of large DC fields, thereby reducing the effects of electroosmosis, electrophoresis, and protein deformation.

Figure 4:
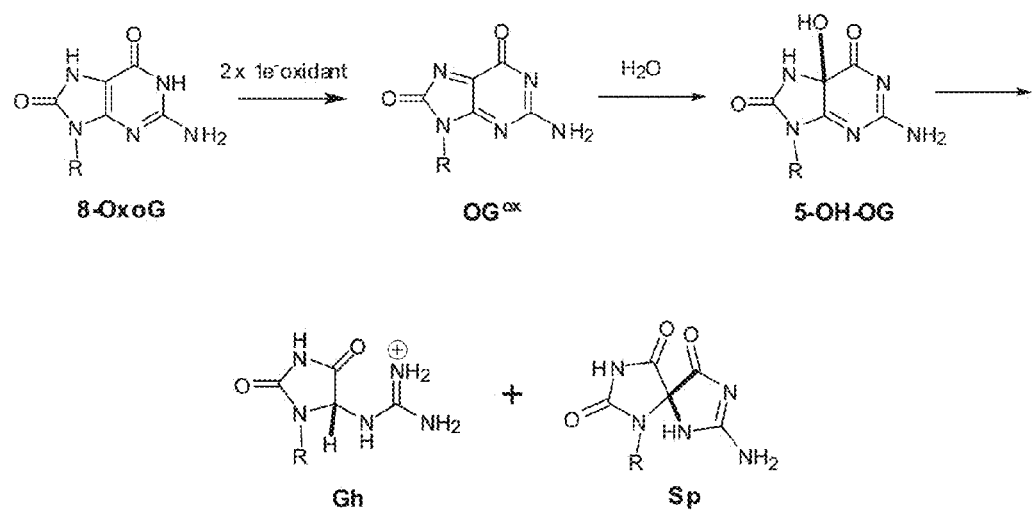
FIG. 4 is a schematic depiction of a reaction pathway for further oxidation of 8-oxoG in accordance with an embodiment of the present invention.

Returning to DNA damage, the electron-rich DNA bases are sensitive to oxidation, and guanine (G), with the lowest redox potential (1.3 V. vs. NHE) of the four bases, is particularly so. The most common product of G oxidation is 8-oxoG, a lesion that leads to G-to-T transversion mutations if left unrepaired. Interestingly, 8-oxoG (~0.7 V. vs. NHE) has a dramatically lower redox potential than G, and it is therefore a hot spot for further oxidation. Products of 8-oxoG oxidation in DNA include the hydantoins, Sp (spiroiminodihydantoin) and Gh (guanidinohydantoin). FIG. 4 shows the reaction pathway for further oxidation of 8-oxoG to yield stable lesions Gh in ds-DNA and Sp in ssDNA and nucleosides. Sp and Gh are ubiquitous products of guanine oxidation from many types of reactive oxygen species as studied in an in vitro setting.

Figure 5:
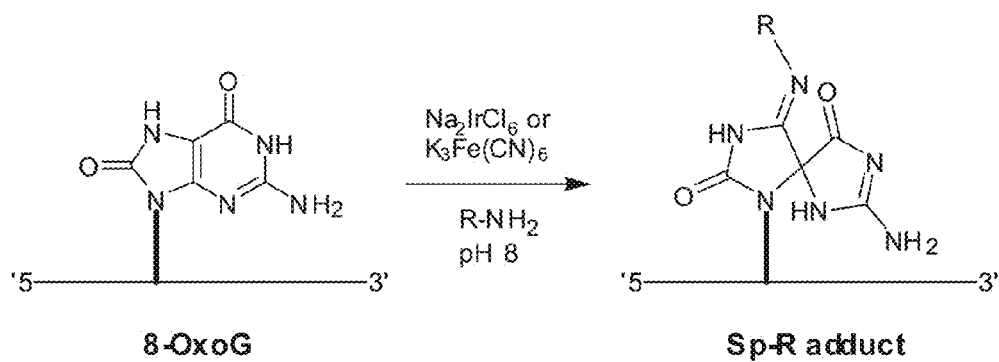
FIG. 5 is a schematic depiction of nucleic acid adduct formation chemistry in accordance with an embodiment of the present invention.

The large difference in redox potential between G and 8-oxoG allows a sensitive method for selectively oxidizing only 8-oxoG in a DNA strand containing various sequences, even sequences otherwise susceptible to oxidation such as 5'-GGG-3'. The mild one-electron oxidants $Na_2IrCl_6$ or $K_3Fe(CN)_6$ are suitable for this purpose. Additionally, a 2-e⁻ oxidized form of 8-oxoG ($OG^{ox}$ in FIG. 4) is initially formed and then trapped by a nucleophile such as $H_2O$. In the presence of better nucleophiles such as primary amines, covalent adducts are formed to that species (FIG. 5). For example, oxidation of an 8-oxoG-containing oligomer in the presence of 50 µM spermine generates a covalent adduct of spermine to the oligomer. Furthermore, many DNA binding proteins, typically rich in lysine residues, form covalent cross-links to 8-oxoG-containing DNA.

The inventors have developed mild conditions for converting 8-oxoG, a very common but structurally subtle base lesion, to an adduct whose size, shape, and functionality depend on the primary amine or other current modulating compound that is appended. Thus, virtually any primary amine can be incorporated into a nucleic acid via and 8-oxoG intermediate. While any primary amine is contemplated for incorporation into nucleic acid adducts, specific non-limiting examples include benzyl amine, lysine, arginine, spermine, spermidine, an amine derivative of β-cyclodextrin, and the like, including combinations thereof. Further details regarding specific adduct chemistry is described below.

Various lesions can be useful in the formation of nucleic acid adducts that are detectable via channel recordings, including lesions such as uracil (in DNA), 8-oxoG, and $1,N^6$-ethenoadenosine. It should be noted that various strategies and chemistries are contemplated for adduct formation, and any such chemistry is considered to be within the present scope. Additionally, the present scope includes any nucleic acid adduct generated from a nucleic acid lesion that results in a measurable change in the rate of translocation of the adduct through the channel or a change in current as the adduct is within the constricted portion of the channel compared to the nucleic acid without the adduct.

Figure 6:
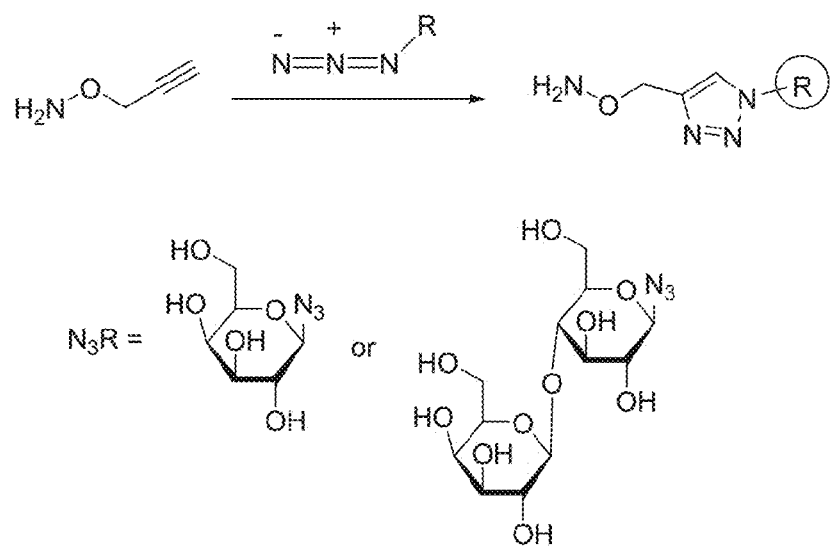
FIG. 6 is a schematic depiction of nucleic acid adduct formation chemistry in accordance with an embodiment of the present invention.

The presence of uracil in DNA constitutes a mutation; often derived from a hydrolytic deamination reaction of C, uracil (U) codes like T. Because of the frequency of its occurrence in the genome, there exists a highly evolved protein, Uracil-DNA Glycosylase (UDG), in all organisms to excise U. UDG operates on U in either dsDNA or ssDNA and cleanly hydrolyzes the glycosidic bond to produce an abasic (AP) site. AP sites can be somewhat unstable, and thus they can undergo β-elimination under basic conditions leading to strand scission. However, when an alkoxyamine is present in solution during generation of AP sites, the sugar aldehyde can be efficiently trapped, leading to a stable oxime ether. The biotinylated alkoxyamine Aldehyde Reactive Probe (ARP) can be used to detect AP sites in DNA. While the ARP adduct can be used for ion channel measurements, the retardation in translocation rate can be slight and the change in current level during translocation is relatively minor. This is likely due to the flexibility of the biotin attachment. Accordingly, in various aspects, nucleic acid adducts can be made that incorporate current modulating compounds having a size and rigidity that allows greater discrimination in the channel recordings. In one aspect, for example, propargyloxyamine can be converted via "click" chemistry with organic azides to a suite of alkoxyamines for conjugation to the abasic site. Two non-limiting examples are shown in FIG. 6 utilizing azidosugars to form the adduct. Such compounds retain the alkoxyamine group for functionalization of the AP site while introducing a large and relatively rigid adduct. One additional advantage of using carbohydrates for adduction is that they will retain water solubility.

Figure 7:
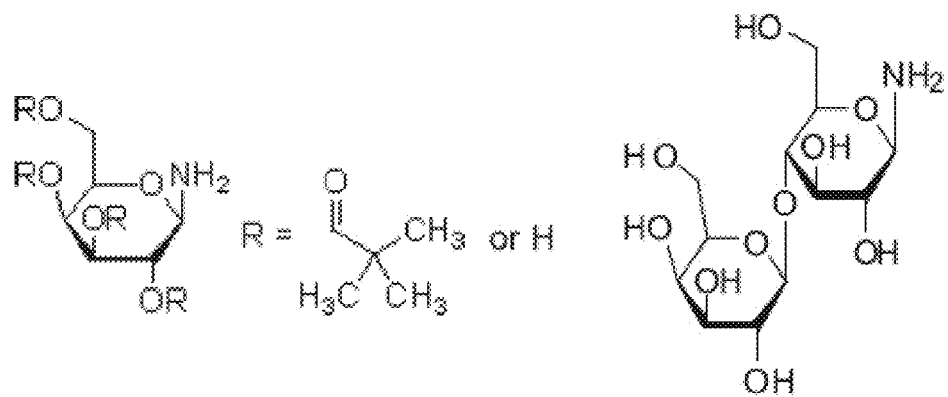
FIG. 7 is a schematic depiction of nucleic acid adduct formation chemistry in accordance with an embodiment of the present invention.
Figure 8:
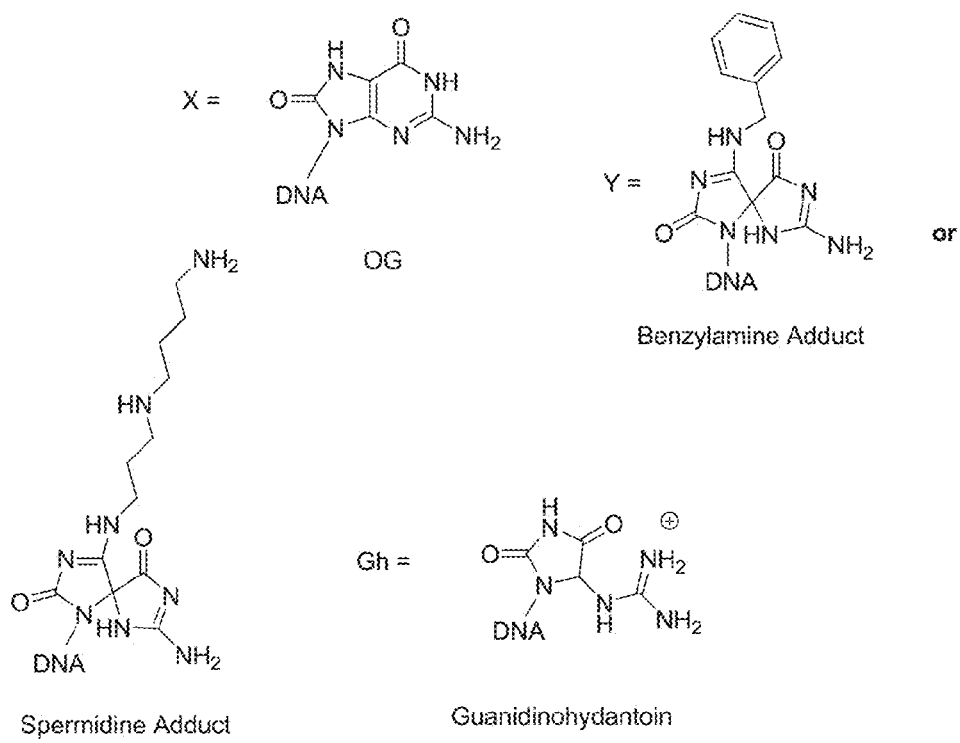
FIG. 8 is a schematic depiction of examples of nucleic acid adducts in accordance with an embodiment of the present invention.

In another aspect, various chemistries from functionalization of AP sites can also be applied to detection of 8-oxoG with certain changes. For example, the conditions for mild oxidation of 8-oxoG (see FIG. 5) can be adjusted such that the adduct formation will be conducted with a primary amine instead of an alkoxyamine, as has been discussed above. Primary amines can couple to 8-oxoG under mild oxidation conditions. Non-limiting examples of some related primary amines that can be used for adduct formation are shown in FIG. 7. It should be noted that any primary amine capable of being introduced into a nucleic acid adduct and that is detectable in channel recordings is considered to be within the present scope. Further adducts generated from 8-oxoG are shown in FIG. 8.

Figure 9:
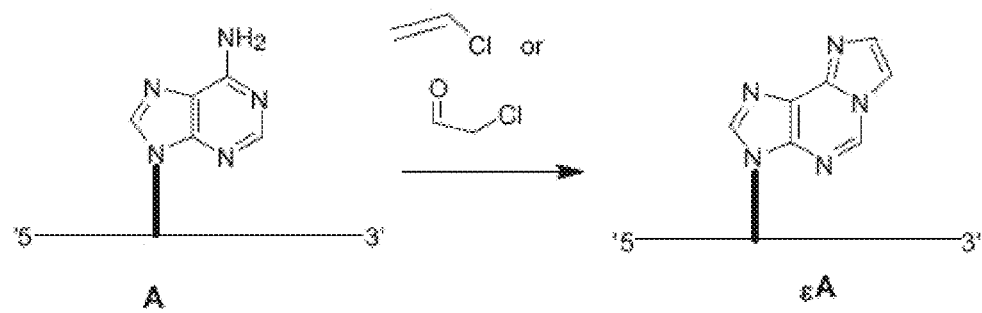
FIG. 9 is a schematic depiction of DNA base lesion chemistry in accordance with an embodiment of the present invention.

Another useful DNA base lesion is the alkylated base 1,$N^6$-ethenoadenine (εA). εA is a product of vinyl chloride toxicity as well as being a member of a broader class of alkylated bases formed by condensation of lipid peroxidation products (such as malondialdehyde) with DNA bases. εA is conveniently synthesized by the reaction of chloroacetaldehyde with adenosine, as is shown in FIG. 9, where the formation of εA is shown by the condensation of A with vinyl chloride or α-haloacetaldehyde. Two types of repair enzymes remove this damage from DNA, AlkA and AlkB, and they do so by very different mechanisms. AlkA operates on a broad class of alkylated adenosines and is a simple glycosylase that removes the damaged base, thus generating an abasic site. In this sense, AlkA functions with εA very much like UDG acts on U, with the difference that AlkA prefers double-stranded substrates. As such, dsDNA substrates need to be denatured before they can pass through a nanopore such as α-HL. εA can also be directly repaired from single-stranded DNA using the enzyme AlkB.

Additionally, in some aspects nanopores large enough to translocate ds-DNA can be used in the manner described for ss-DNA in order to detect ds-DNA adducts via the translocation dependent modulation of electrical current. As such, ds-DNA adducts and methods of their detection are considered to be within the present scope.

Figure 10:
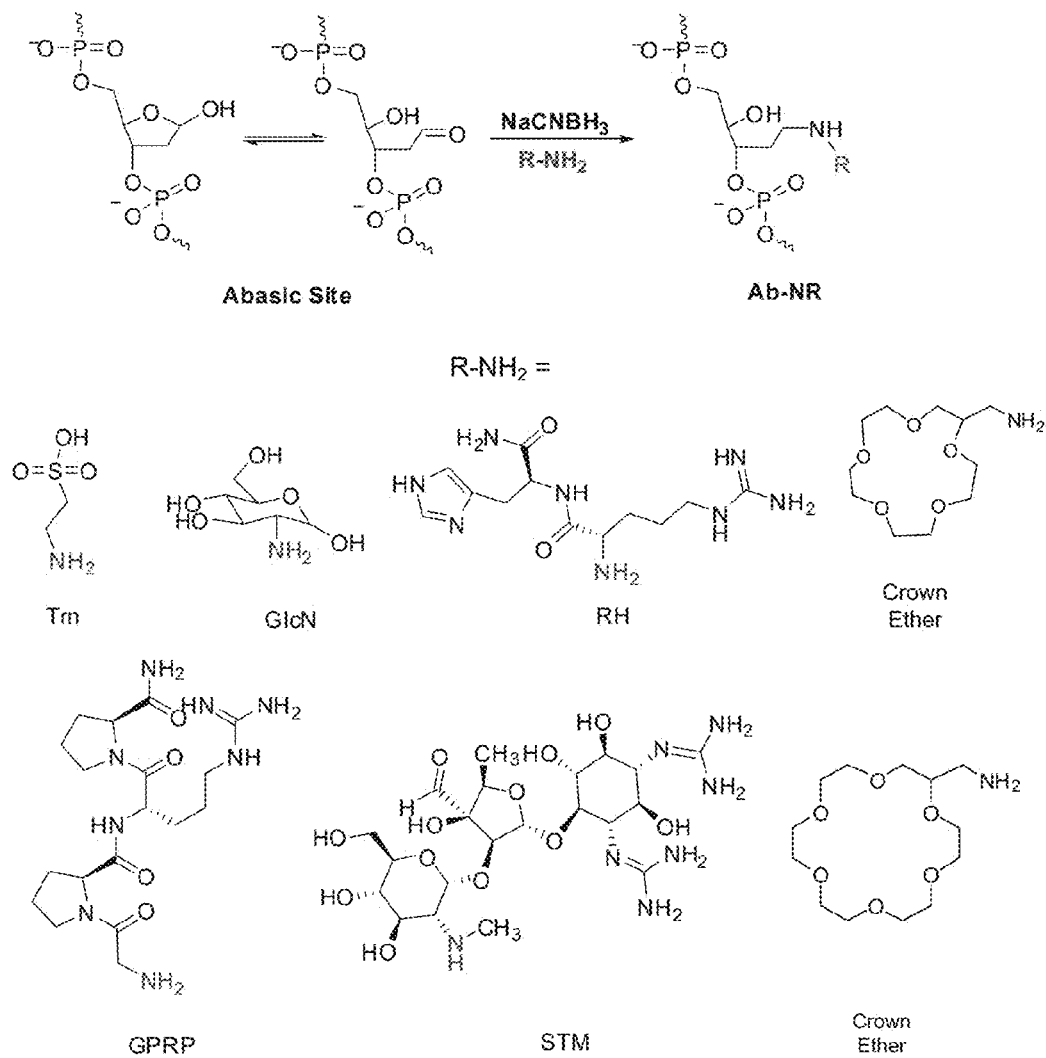
FIG. 10 is a schematic depiction of nucleic acid adduct examples in accordance with an embodiment of the present invention.

Thus, numerous adducts generated from AP sites are contemplated, and the present scope includes any current modulating compound coupled to a nucleic acid at an abasic site, including those associated with lesions. DNA AP tautomerizes between ring-closed form and ring-open aldehyde form, the existence of which allows AP to be further functionalized via coupling with amines to form Schiff bases, followed by reduction to produce stable amine adducts (Ab-NR) by $NaCNBH_3$. Non-limiting examples of such adducts are shown in FIG. 10, where Taurine (Trn), glucosamine (GlcN), Arg-His (RH), Gly-Pro-Arg-Pro amide (GPRP), streptomycin (STM), and crown ethers are attached to DNA AP to produce adducts (AP-NR) via reductive amination. Thus the electrical signature of AP in the adduct can be dramatically changed and removed beyond the range of normal DNA bases in the wild-type α-HL in both homopolymer sequences and heterosequences, which provides benefits for lesion recognition and sequencing development. This modification method can also be extended to DNA analysis using other proteins and solid-state nanopores. The single-molecule lesion recognition by protein ion channel can, to a great extent, advance the understanding of disease origins and diagnostics.

In addition to those specific examples described, the current modulating compounds can vary depending on the desired outcome of the recording procedure and the particular chemistry involved. General non-limiting examples of current modulating compounds include alkanes, alkenes, alkynes, aryls, sugars, carbohydrates, azides, halides, amines, imines, peptides, crown ethers, metal-binding ligands, transition metal complexes and the like, including combinations thereof.

Figure 62:
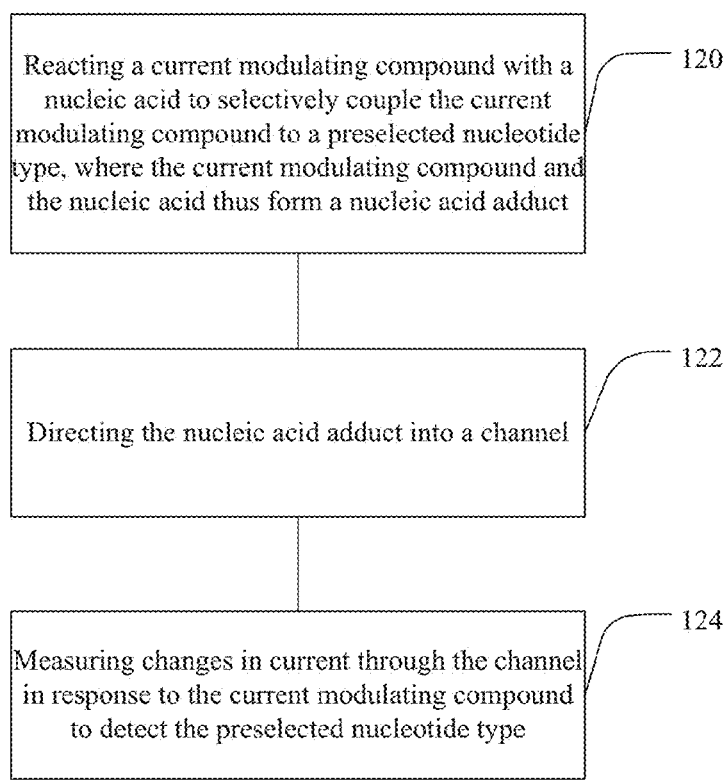
FIG. 62 is a schematic diagram of a method of obtaining sequence information from a nucleic acid in accordance with an embodiment of the present invention.
Figure 63A:
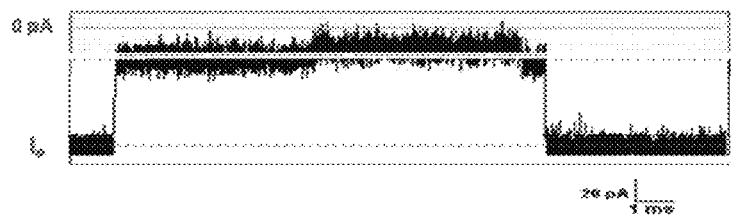
Figure 63A:
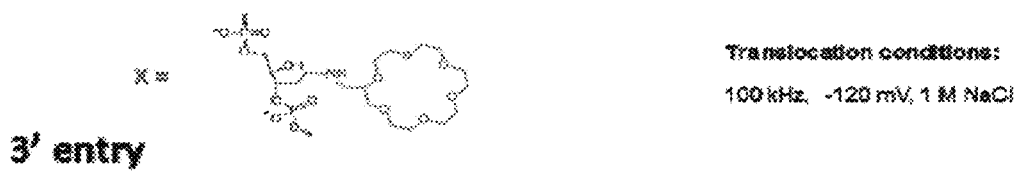
Figure 63B:
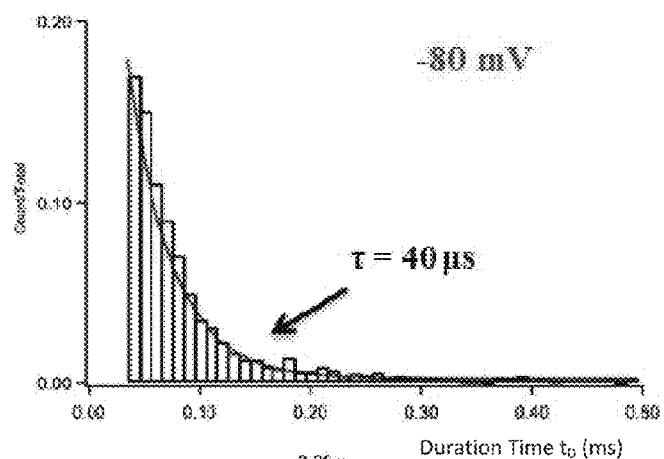
Figure 63C:
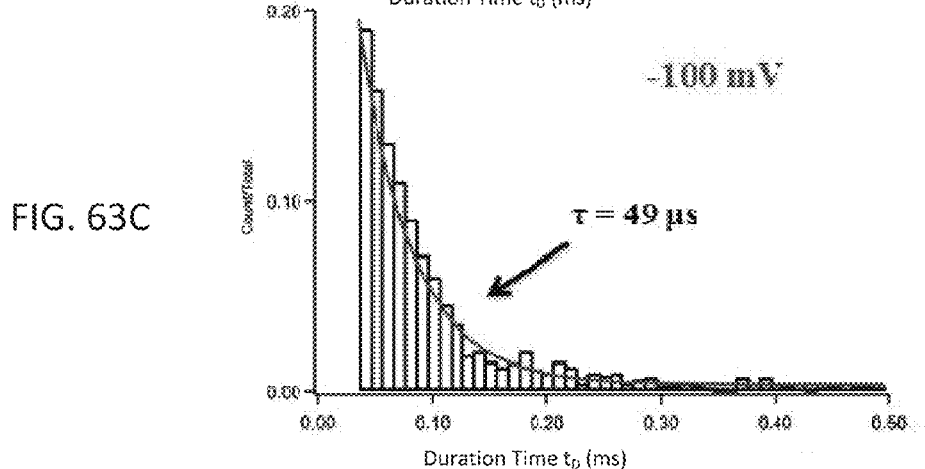
Figure 64:
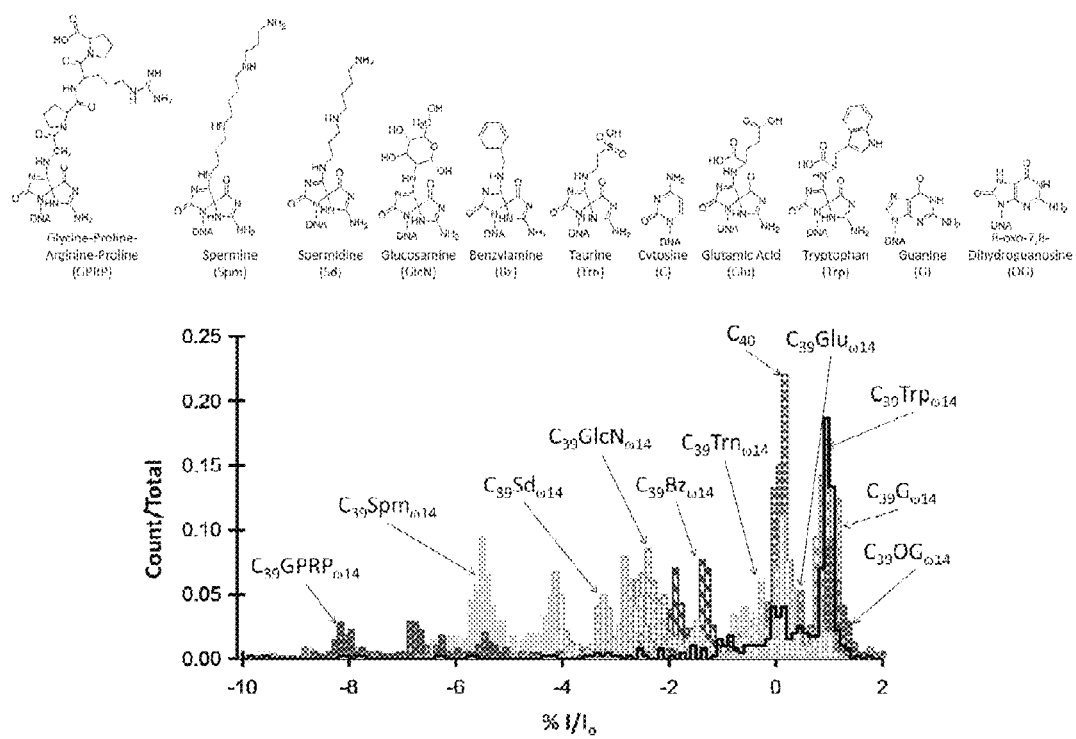
FIG. 64 shows the structures of adducts of amines to 8-oxoguanosine in DNA strands. "DNA" refers to the modified bases as shown being connected to the C1' carbon of 2'-deoxyribose via a glycosidic bond. Bottom: Changes in current blockage when immobilized in the alpha-hemolysin ion channel for strand containing adducts compared to a reference strand poly-$dC_{40}$.
Figure 65:
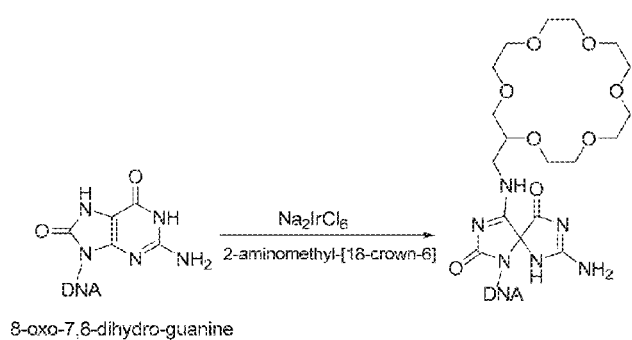
FIG. 65 shows the formation of 18-crown-6 adduct to guanosine (SEQ ID NO:11) in DNA. Bottom: Formation of 18-crown-6 adduct to cytidine in poly-dC DNA.
Figure 65:
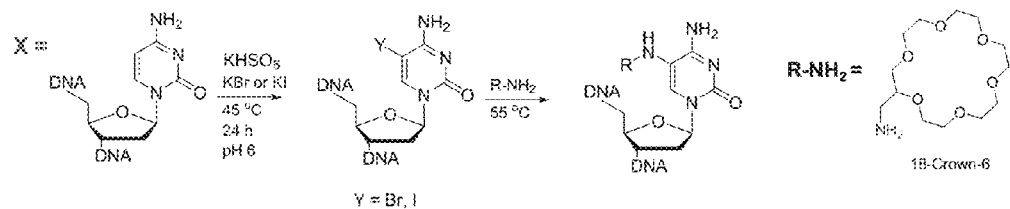
Figure 66:
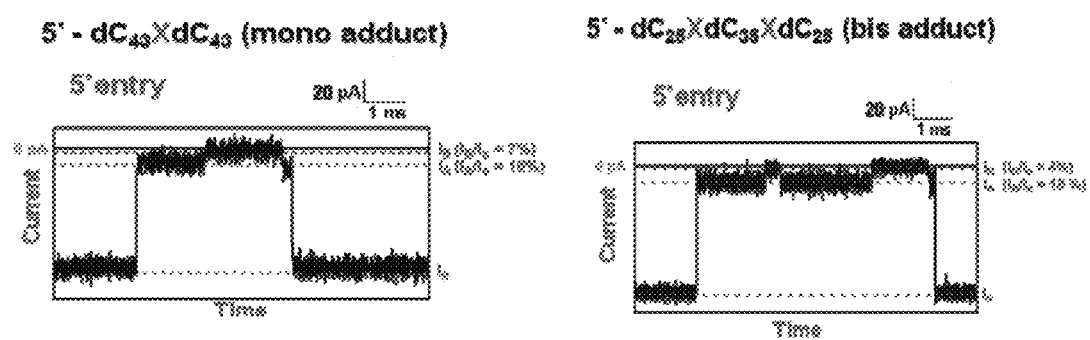
FIG. 66 shows when one crown ether adduct (X) is present in the DNA strand, the current-time trace reports the location of the adduct by a shift in the blockage current from 16% for poly-dC to 7% for the crown ether adduct. Right: When two crown ether adducts (X) are present in the strand, two shifts in the current blockage level are seen. Thus, this example shows how the crown ether adducts serve as registration marks. The sequence in between the two registration marks could then be scanned hundreds of times, via changing the voltage bias, to obtain high signal to noise data from which at least a portion of the sequence could be determined.
Figure 67:
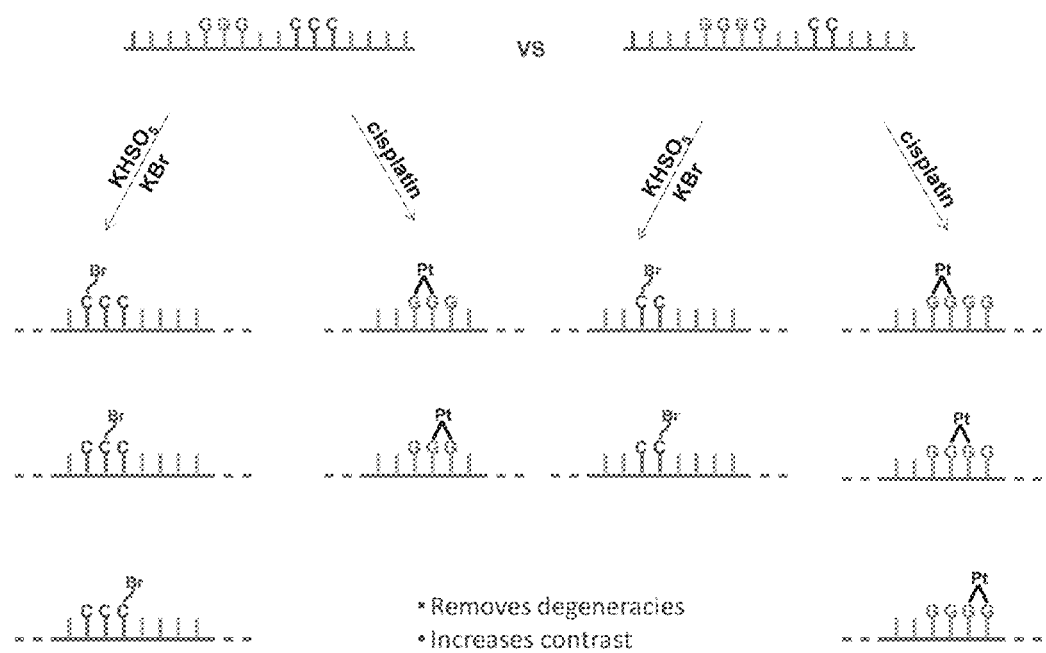
FIG. 67 shows that the identity and number of base repeats can be determined by low level (~10%) conversion of a specific base to an adduct. This is illustrated for bromination of C and platination of adjacent GG sites.

As has been described, techniques for use in obtaining sequence information from a nucleic acid are also provided. In such cases, a nucleic acid can have current modulating compounds associated with certain bases or base sequences to form a nucleic acid adduct that can allow detection via channel recording methodologies. In one aspect, as is shown in FIG. 62, a method of obtaining sequence information from a nucleic acid can include reacting a current modulating compound with a nucleic acid to selectively couple the current modulating compound to a preselected nucleotide type, where the current modulating compound and the nucleic acid thus form a nucleic acid adduct 120. The method can also include directing the nucleic acid adduct into a channel 122 and measuring changes in current through the channel in response to the current modulating compound to detect the preselected nucleotide type 124. It should be noted that many of the chemistries disclosed that relate to nucleic acid damage can be utilized to associate current modulating compounds with distinct nucleotide base types or sequences, and as such, can be useful in obtaining sequence information.

Figure 11:
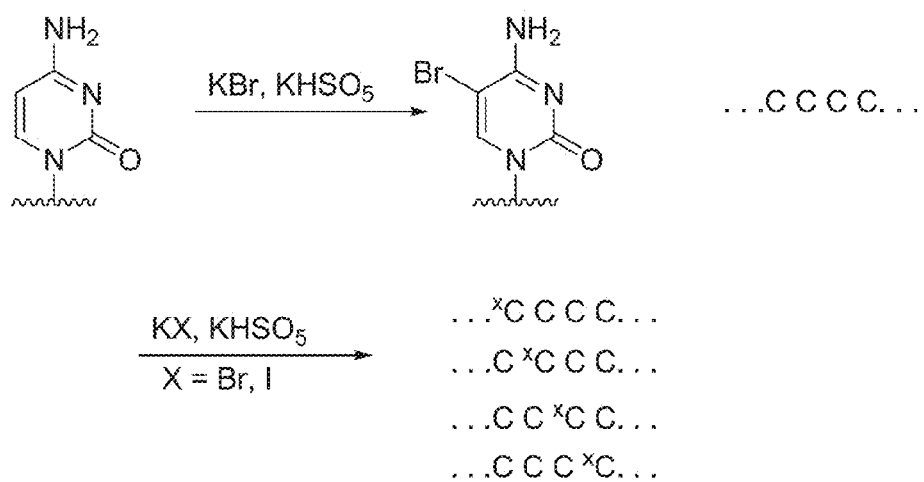
FIG. 11 is a schematic depiction of halogenation reaction examples in accordance with an embodiment of the present invention.

By modifying a specific nucleotide base type of a given nucleic acid, qualitative sequence information of the nucleic acid sequence can be determined. Additionally, such qualitative evaluation can extend to related inquiries, such as epigenetics. Thus any qualitative evaluation can be made in which specific modifications can be made to the nucleic acid to allow the introduction of a current modulating compound to thus form a nucleic acid adduct. For example, a halogenation reaction such as the bromination of cytosine under mild conditions (e.g. KBr, $KHSO_5$) results in a reaction that is highly selective for C over T, G, and A. As is shown in FIG. 11, bromination of cytosine can be used to selectively modify at least a portion of the cytosine bases on a nucleic acid strand. These modified cytosines can be detected via channel recording methods, and thus are useful for determining sequence information. FIG. 11 also shows a general reaction that can utilized Br or I for such modifications. It should also be noted that any halide capable of being incorporated and discriminated using channel recording methods is considered to be within the present scope.

Figure 12:
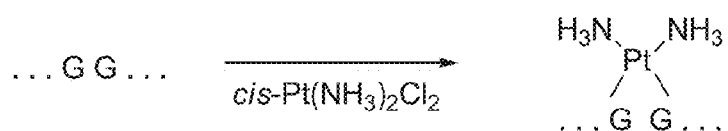
FIG. 12 is a schematic depiction of a platination reaction example in accordance with an embodiment of the present invention.

As another example, cis-platin can be reacted with a nucleic acid to introduce nucleotide base modifications. Cis-platin binds preferentially to adjacent guanines via kinetically stable coordination bonds to N7 of guanine, as is shown in FIG. 12. Thus the cis-platin is a current modulating compound that can be detected via channel measurements. The amine ligands can also be varied to larger groups, such as, for example, 1,2-cyclohexanediamine, in order to further modulate the channel signal. Additionally, several cis-platin analogs can be utilized that are commercially available.

It is also disclosed that AP sites or other lesions can be formed at nucleotide bases within the nucleic acid, and that such sites can be utilized as has been described above in order to selectively modify a preselected base type. Thus any technique for forming a lesion or AP site selectively in a nucleic acid is considered to be within the present scope. In this case, a specific nucleotide base type, such as, for example, guanosine, can be oxidized to form 8-oxoG and current modulating compounds can be associated with these sites as has been described. In this case, one or more, or even all of the guanosines in the nucleic acid can be oxidized to 8-oxoG. Generally, one or more of a specific base type can be modified by any known chemistry to incorporate a current modulating compound that allows sequence discrimination. It should be noted that "specific base type" also extends to epigenetic and other base modifications such as 5-methyl-C, for example.

Thus, by modifying a nucleic acid to include current modulating compounds, such compounds can be detected, thereby allowing correlation between channel recordings and nucleic acid sequence information. This process can allow the rapid sequencing of nucleic acids, as well as more focused investigation of specific sequences. For example, in one aspect, such modifications allow the detection of adjacent nucleotide bases of the same nucleotide type. Such a determination can be made for adjacent nucleotide bases on the same strand provided the multiple current modulating compounds can be discriminated via the channel recordings. Additionally, such a determination can be made for adjacent nucleotide bases where each base of the pair is modified on a different nucleic acid strand of the same sequence. By pooling the channel recording data, the adjacent nature of these bases can be determined. Also, base repeats greater than two can be investigated as well through similar methodology by comparing the base signatures across nucleic acid strands.

Additionally, nucleic acid adducts are also provided. In one aspect, for example, a nucleic acid adduct can include a nucleic acid having a damaged region and a current modulating compound coupled to the damaged region. Such adducts can be formed by a variety of chemistries, including those described herein. The current modulating compounds that can be coupled to the damaged region include, without limitation, alkanes, alkenes, alkynes, aryls, sugars, carbohydrates, azides, halides, amines, imines, peptides, crown ethers, metal-binding ligands, transition metal complexes and the like, including combinations thereof. In some cases, the damaged region is an AP site.

Also, a system for detecting a current modulating compound is provided. Such a system can include a nanoporous membrane including a conical nanopore having an opening with a suspended lipid bilayer across the opening, a pair of electrodes configured to register changes in electrical current across the opening, and a nucleic acid adduct of a nucleic acid and a current modulating compound located within the nanopore. Such a system can additionally include a protein embedded in the lipid bilayer to form a channel such that transport of the nucleic acid adduct across the channel is inhibited while transport of non-adduct nucleic acid is not substantially inhibited, as has been described herein.

Method of Using a Current Modulating Compound as a Registration Marker on a Nucleic Acid In an aspect the disclosure provides a method of obtaining sequence information from a nucleic acid comprising providing at least one nucleic acid adduct, wherein the at least one nucleic acid adduct comprises a nucleotide type coupled with a current modulating compound; directing the nucleic acid into a channel, wherein the channel comprises an initial current in the absence of the nucleic acid; measuring the current as the nucleic acid is in the channel; detecting the current modulating compound in the channel; registering the identity and location of the current modulating compound on the nucleic acid; and assigning the current modulating compound as a first registration marker on the nucleic acid, wherein the first registration marker provides an detectable reference point in the sequence of the nucleic acid.

In another aspect the disclosure provides a method of assigning a registration marker within a nucleic acid comprising providing at least one nucleic acid adduct, wherein the at least one nucleic acid adduct comprises a nucleotide type coupled with a current modulating compound; directing the nucleic acid into a channel, wherein the channel comprises an initial current in the absence of the nucleic acid; measuring the current as the nucleic acid is in the channel; detecting the current modulating compound in the channel; registering the identity and location of the current modulating compound on the nucleic acid; and assigning the current modulating compound as a first registration marker on the nucleic acid.

In embodiments of the above two aspects, which are described in more detail below, the methods can further comprise a nucleic acid that includes at least a second nucleic acid adduct that comprises a second nucleotide type coupled with a second current modulating compound; detecting the second current modulating compound in the channel; registering the identity and location of the second current modulating compound on the nucleic acid; and assigning the second current modulating compound as a second registration marker on the nucleic acid; and wherein the second registration marker is detected while measuring at least a portion of the nucleic acid.

In yet another aspect the disclosure provides a method for identifying the number of repeat nucleotides in at least a portion of a nucleic acid strand comprising a) providing at least one nucleic acid adduct in a first nucleic acid strand, wherein the at least one nucleic acid adduct comprises a first nucleotide type coupled with a current modulating compound, and wherein the first nucleotide type is adjacent to at least a second nucleotide type wherein the first and second nucleotide type is the same; b) directing the nucleic acid into a channel, wherein the channel comprises an initial current in the absence of the nucleic acid; c) measuring the current as the nucleic acid translocates the channel; d) detecting the current modulating compound; e) repeating steps a)-d) at least a second time with at least a second nucleic acid strand wherein the first and second nucleic acid strands comprise the same sequence; and f) determining the number of repeat nucleotides in the sequence of the first and second nucleic acid strand by combining data obtained from steps c) and d).

Thus, the above aspects provide methods of using a current modulating compound coupled to a nucleic acid as a registration marker. As used herein, the term "coupled" relates to any type of interaction or modification (e.g., covalent bond, ionic bond, hydrogen bonding, hydrophobic interaction) that allows for the formation of a nucleic acid adduct through the association of a nucleotide type and at least one current modulating compound such as, for example, under conditions of the assays and methods described herein. In certain embodiments, at least one current modulating compound is coupled to at least one nucleotide on the nucleic acid strand. In certain embodiments, a voltage bias is applied, directing the nucleic acid into a channel comprising a nanopore. In certain embodiments, the at least one current modulating compound is detected as the nucleic acid is within the nanopore and provides a registered known and identified point on the nucleic acid. Thus in these methods, the current modulating compound can be termed a "registration marker." In certain embodiments, the nucleic acid translocates the channel and/or nanopore. In certain embodiments, the nucleic acid is immobilized within the channel and/or nanopore.

In certain embodiments, the nucleic acid comprises one registration marker. In certain embodiments, the nucleic acid contains two or more registration markers, and optionally a number of registration markers up to the total number of nucleotides in any nucleic acid under analysis (e.g. 3, 4, 5, 6, 7, 8, 9, 10, 20, 30, 40, 50, 60, 70, 80, 90, 100, 1000, 10,000, 100,000, 1,000,000, 1,000,000,000 or more registration markers). In certain embodiments, a percentage of the nucleotides, relative to the total number of nucleotides in the entire nucleic acid sequence of interest, are associated with the registration markers. In some embodiments, the percentage is between 0.01% and 100% (e.g. 0.01%, 0.1%, 0.5%, 1%, 2%, 3%, 4%, 5%, 6%, 7%, 8%, 9%, 10%, 15%, 20%, 30%, 40%, 50%, 60%, 70%, 80%, 90% or 100%). In certain embodiments, a low percentage of the nucleotides, relative to the total number of nucleotides in the entire nucleic acid sequence of interest, are associated with the registration markers. In some embodiments, the low percentage is less than 20% (e.g. less than 19%, 18%, 17%, 16%, 15%, 14%, 13%, 12%, 11%, 10%, 9%, 8%, 7%, 6%, 5%, 4%, 3%, 2%, 1%, 0.5%, 0.1%, 0.01%). For example, in some embodiments, it may be advantageous to incorporate a low percentage of nucleotides associated with registration markers so that longer spans of sequence located between markers can be read multiple times. In certain embodiments, the registration markers are in random positions along the nucleic acid. In certain embodiments, the registration markers are in different places along two or more nucleic acid strands within the same sequence. Merely to provide an illustrative embodiment, consider a single stranded DNA having a sequence of 5'-polyAATCGCCGTTT-3' (SEQ ID NO:12), where the first A is the noted as nucleotide 1 and the last T is noted as nucleotide 11. Embodiments can provide a nucleic acid comprising the current modulating compound located at nucleotide 4, for example, (which is a C base) and on a second nucleic acid strand of the same sequence, the nucleic acid comprising the current modulating compound could be located at nucleotide 6 (which is also a C base, but further along in the sequence).

In certain embodiments, the two or more registration markers comprise the same current modulating compound such as, for example, a nucleic acid comprising a single stranded DNA wherein the same current modulating compound is coupled to two different guanine nucleotides in the DNA. In certain embodiments, the two or more registration markers comprise different current modulating compounds such as, for example, a nucleic acid comprising a single stranded DNA wherein one type of current modulating compound is coupled to a guanine nucleotide and a different type of current modulating compound is coupled to a cytosine nucleotide. In certain embodiments, the two or more registration markers can comprise the same type and different types of current modulating compounds such as, for example, a nucleic acid comprising a single stranded DNA and two or more current modulating compounds of one type are coupled to two or more guanine nucleotides and two or more current modulating compounds of a different type are coupled to two or more cytosine nucleotides. In certain embodiments, the same type of current modulating compound is associated with one nucleotide type. In certain embodiments, the same type of current modulating compound is associated with more than one nucleotide type.

In certain embodiments, the use of the registration marker is to provide a known location or point on the nucleic acid that can be used to aid with data analysis. In certain embodiments, data analysis is performed to determine the sequence of at least a portion of the nucleic acid. In certain embodiments, a change to the applied bias is made once the registration marker is detected. In some embodiments, the change to the voltage bias is selected from the non-limiting group including reversing, increasing, decreasing, removing the voltage bias or any combinations thereof.

In certain embodiments, the voltage bias can be modified in order to change the motion of the nucleic acid. In certain embodiments, the change in voltage bias can reverse the original direction of motion, or slow or increase the rate of motion in the original direction or combinations thereof. In certain embodiments, the change in voltage bias and the change in motion of the nucleic acid allow at least a portion of the nucleic acid to be measured or read two or more times. In certain embodiments, the voltage bias is reversed and the motion of the nucleic acid is reversed. In certain embodiments, the reversal of the direction of motion of the nucleic acid enables at least potions of the nucleic acid to be read or measured at least a second time, and optionally a plurality of times. In certain embodiments, the method comprises a second registration marker that is detected after the motion of the nucleic acid is changed. In certain embodiments, the voltage bias is modified again to change the motion of the nucleic acid. In certain embodiments, the voltage bias is reversed when the first registration maker is detected and again reversed when the second registration marker is detected. Such embodiments can provide multiple measurements of the same section of sequence of the nucleic acid through "flossing" or the repeated reversal in direction of the nucleic acid in the nanopore. In such embodiments the term "flossing" means that the nucleic acid is moved (or flossed) back and forth to allow for multiple readings of the same portion of the nucleic acid, which can improve the accuracy of sequence determination of the nucleic acid. In certain embodiments, the same portion of the nucleic acid is measured at least one time or a plurality of times (e.g. at least 1, 2, 3, 4, 5, 6, 7, 8, 9, 10, 20, 30, 40, 50, 100, 200, 300, 400, 500, 1000, 10,000 times).

In certain embodiments, the nucleic acid can be flossed between multiple registration markers coupled to one or more nucleotide types comprising the nucleic acid strand. For example, the nucleic acid can be a single stranded DNA and comprises 5 registration markers (1, 2, 3, 4, and 5). In this example, the DNA can be measured multiple times between markers 1 and 2, then 2 and 3, then 3 and 4, and then 4 and 5. In another illustrative example, the DNA can be measured between markers 1 and 4 multiple times, without changing the voltage bias when markers 2 and 3 are detected between the flossing of the DNA between markers 1 and 4.

In certain embodiments, the voltage bias is changed each time a registration marker is detected. In other embodiments, the voltage bias need not be changed when a registration marker is detected (i.e., the voltage bias is changed as needed or desired). In certain embodiments, the nucleic acid comprises three or more registration markers. In certain embodiments, the number of measurements of portions of the nucleic acid between registration markers is the same. For example, a nucleic acid containing three registration makers, noted as 1, 2, and 3 (for illustrative purposes only), can provide one section between registration markers 1 and 2 and another section between registration markers 2 and 3. In such an example, the portion between markers 1 and 2 can be measured 5 times and the portion between markers 2 and 3 can be measured 5 times by changing the voltage bias as the registration marker is detected. In certain embodiments, the number of reads of portions of the nucleic acid between registration markers is different. For example, a nucleic acid again contains three registration makers, 1, 2, and 3, thus providing a section between registration markers 1 and 2 and another section between registration markers 2 and 3. In this example, the portion between markers 1 and 2 can be measured 5 times and the portion between markers 2 and 3 can be measured 10 times.

In certain embodiments, multiple measurements of the same portion of a nucleic acid strand can improve the sequencing accuracy of at least a portion of the nucleic acid. It will be appreciated that as a nucleic acid or portions of a nucleic acid translocate through a channel and/or nanopore, the duration for nucleic acids or portions of nucleic acids with the same sequence to translocate the channel and/or nanopore varies. As an example, when the nucleic acid is unmodified DNA, the distribution of duration times can be fit to an translocation model as described in Lubensky et al. (*Biophys. J.*, vol. 77, no. 4, pp. 1824-1838, Oct. 1, 1999, 1999) incorporated herein by reference. In certain embodiments, multiple measurements of the same portion of a nucleic acid can improve the sequence accuracy by providing additional measurements of the current level and duration of the current measurements of the portion of the nucleic acid. These multiple measurements can be used with data analysis processing techniques to determine the most likely sequence of a nucleic acid.

In certain embodiments, this method can be additionally applied and particularly useful to a nucleic acid comprising two or more of the same nucleotides in a row, also termed repeat bases. For example, when a nucleic acid is single stranded DNA and the strand contains a span of 5 adenine nucleotides in series. In such an example, the 5 adenines are predicted to produce the same current level, and thus one way to determine the number of nucleotides in a row would be to determine the number based on the duration of the current level measured. However, as discussed above, the translocation duration for identical nucleic acid strands or sections of nucleic acid strands will vary. In certain embodiments, multiple measurements of a section of the nucleic acid containing at least two of the same nucleotides can be used with known data processing techniques to more accurately determine the sequence of the nucleic acid.

In certain embodiments, the current modulating compound comprises any compound or molecule that, when coupled to a nucleic acid (or nucleotide type in a nucleic acid), modulates current flow through a channel when the current modulating compound is present in the channel, as compared to the same nucleic acid without the current modulating compound. In certain embodiments, the current modulating compound is selected from the non-limiting group comprising alkanes, alkenes, alkynes, aryls, sugars, carbohydrates, azides, halides, amines, imines, peptides, crown ethers, metal-binding ligands, transition metal complexes and the like, including combinations thereof. In certain embodiments, the current modulating compound is coupled to the nucleic acid by a damaged lesion that is naturally occurring in the nucleic acid strand as described in this application. In certain embodiments, the nucleic acid strand is chemically modified to produce a damaged lesion to enable the coupling of a current modulating compound as described in this application. As an example, a nucleotide in the nucleic acid is converted to an abasic site and the current modulating compound aminomethyl-18-crown-6 is coupled to the abasic site.

Methods for Identifying Repeat Nucleotides

Described herein is a method for using current modulating compounds to identify repeat nucleotides within a nucleic acid sequence. As is described previously, when a nucleic acid sequence is comprised of one or more sections that contain two or more of the same nucleotide in a row, it can present a challenge in correctly determining the number of such identical nucleotides in each section. For example, the nanopore sequencing method can produce uncertainties when trying to interpret signals from sequences such as: 5'-polyTAGGGATCCCGTA-3' (SEQ ID NO:13) and 5'-TAGGGGATCCGTA-3' (SEQ ID NO:14), leading to uncertainty in the number of specific nucleotides (G and C, in this example) present in the sequence. While using current modulating compounds as registration markers can be used to identify these repeat nucleotides, an additional use of current modulating compounds is described herein to identify these repeats based upon separate measurements of multiple nucleic acid strands.

In certain embodiments, a nucleic acid can comprise at least two of the same nucleotides in a row (e.g. at least 2, 3, 4, 5, 6, 7, 8, 9, 10, 20, 30, 40, 50, 60, 70, 80, 90, 100, or 1,000). In some embodiments, a nucleic acid is comprised of at least one current modulating compound coupled to at least one nucleotide that is adjacent to at least one other nucleotide of the same type. For example, the nucleic acid is single stranded DNA and the sequence is 5'-polyTAGGGATCCCGTA-3' (SEQ ID NO:13), where T is noted as the $1^{st}$ base and A is noted as the $13^{th}$ base in this illustrative example. In this example, a current modulating compound is coupled to the $3^{rd}$ base (G in this case), which is next to another G base, the $4^{th}$ base. In certain embodiments, current modulating compounds can be coupled to more than one nucleotide that is adjacent to at least one other nucleotide of the same type. For example, in the sequence discussed above, 5'-polyTAGGGATCCCGTA-3' (SEQ ID NO:13), current modulating compounds could be coupled to the $3^{rd}$ and $5^{th}$ bases.

In certain embodiments, the method of coupling a current modulating compound to a nucleic acid can result in the compound being coupled to two adjacent bases. In certain embodiments, this method involves cis-platin, as described elsewhere in this application. In certain embodiments, the current modulating compound can be coupled to different repeat bases in different nucleic acids. For example, with the sequence 5'-polyTAGGGATCCCGTA-3' (SEQ ID NO:13), in the first nucleic acid strand, the cis-platin current modulating compound couples to the G bases at positions 3 and 4. In a second nucleic acid strand, the cis-platin current modulating compound couples to the G bases at positions 4 and 5.

In certain embodiments, multiple measurements of the nucleic acids with the same sequence with current modulating compounds at the same or different positions on the strand are taken. For example, the nucleic acid 5'-polyTAGGGATCCCGTA-3' (SEQ ID NO:13) is used and current modulating compounds are coupled to the strands in a random or diffusive pattern. Multiple measurements of different strands with the same sequence indicate that a current modulating compound is detected as positions 3 and 4 as well as 4 and 5. It can then be known that there are three repeat G bases, at positions 3, 4, and 5. In another example, a current modulating compound that binds to only one base at a time, for example bromination of a cytosine base, is used again with the strand 5'-polyTAGGGATCCCGTA-3' (SEQ ID NO:13). Multiple measurements of these strands indicate that there are current modulating compounds detected at positions 8, 9 and 10. Thus, this method enables multiple measurements of nucleic acids to be used to determine the number of repeat bases in a section of a nucleic acid strand.

In certain embodiments, a percentage of the repeat bases are coupled to current modulating compounds in order to enable identification of repeat bases. In certain embodiments, about 1 to 100% of repeat bases are coupled to current modulating compounds (e.g. about 1, 2, 3, 4, 5, 10, 15, 20, 30, 40, 50, 60, 70, 80, 90 or 100%).

In certain embodiments, this method of detecting repeat bases can be combined with the method of using registration markers, previously described herein. For example, current modulating compounds can be coupled to the nucleotide type adenine in a single stranded DNA molecule and the compound used as a registration marker to enable multiple reads of the same section of the nucleic acid. In addition, the cis-platin adduct can be allowed to couple to repeat guanine bases within the same nucleic acid. In such an example, the registration markers associated with the adenine nucleotide can be used to read the same section of the nucleic acid multiple times. In addition, as numerous measurements are made of nucleic acids with the same sequence, the number and position of the cis-platin adduct can be determined to further help with the identification of repeat bases.

EXAMPLES

Example 1 ssDNA can be modified via individual bases and the phosphodiester backbone to introduce high-contrast markers (i.e. current modulating compounds) by altering measured current. These modifications will help to register DNA during multiple reads as well as to improve the signal contrast between bases and decrease the ssDNA trans location time.

Cis Platin Complexation of Adjacent Guanines.

One current modulating compound that can be used to identify individual bases is cis-platin, which binds preferentially to adjacent guanines via kinetically stable coordination bonds to N7 of G, as shown in FIG. 12. The amine ligands can be varied to larger groups (e.g. 1,2-cyclohexanediamine) to modulate the signal; several cis-platin analogs are commercially available and can also be used.

The complexation of cisplatin, cis-$[PtCl_2(NH_3)_2]$, to DNA is governed by the rate of hydrolysis to form aqua species, cis-$[PtCl(NH_3)_2(H_2O)]^+$ and cis-$[PtCl(NH_3)_2(H_2O)_2]^{2+}$. The reactive diaqua species of cisplatin was obtained in aqueous solution through ligand exchange by the removal of $Cl^-$ with 1.95 equivalents of $AgNO_3$, mixing for 48 h protected from light.

Oligonucleotide.

The 64 base oligomer containing GG platination site was synthesized at University of Utah Core Facilities. In this study, cis-$[Pt((GpG)(NH_3)_2]$ adducts were formed to 64-mer containing one or three GpG reactive sites. Cisplatin adducts were obtained through incubation of 4.5 mol equivalents of diaqua platinum species with DNA, $d(T_{31}GGT_{31})$ (SEQ ID NO:15) or $d(T_{12}UT_{10}GGT_6GGT_6GGT_{10}UT_{12})$ (SEQ ID NO:16) in buffer (10 mM sodium phosphate at pH 6.0).

Characterization of the Cisplatin-GG Adduct by High Performance Liquid Chromatography (HPLC) and Electrospray Ionization Mass Spectroscopy (ESI-MS).

The platinated 64-mer GG strands were first purified by HPLC using anion exchange column (a linear gradient from 35% to 100% 10 mM ammonium acetate (pH 7.0) in 10% acetonitrile for 30 min at a flow rate of 1 mL/min) Purified oligomer was dialyzed and its concentration and purity was confirmed by denaturing gel electrophoresis.

Figure 13:
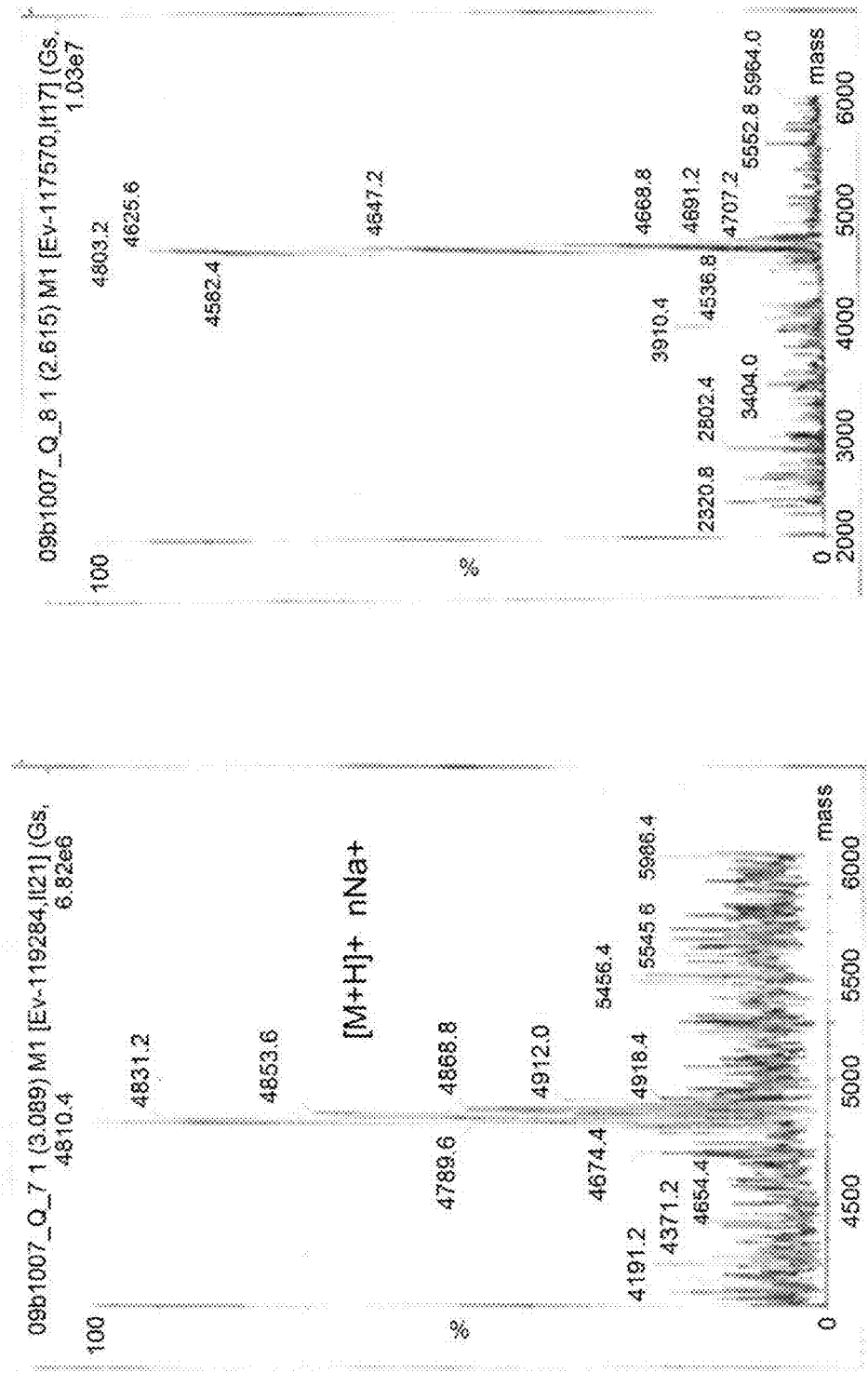
FIG. 13 is a date representation of mass spectrometry analysis of cis-platin adducts in accordance with an embodiment of the present invention.

ESI mass spectrometry analysis of 64mer containing cisplatin adducts could not be obtained due to poor ionization in ESI-MS conditions due to residual salt present in such a large oligomer. A representative oligonucleotide control of 15 bases containing a GG reactive site, d(CATCTGACGGCTCAA) (SEQ ID NO:17), was successfully prepared and characterized. Cis-platin adduct was confirmed in this 15mer with the expected mass of 4767 g/mol and its expected molecular ions in positive modes, FIG. 13.

Immobilization of DNA Oligomers Using Streptavidin-Biotin DNA Complexes.

ssDNA oligomers were prepared with a biotin linker attached at the 3' end for binding to streptavidin. Strong binding between biotin and streptavidin provides a means to immobilize the DNA within the ion channel. The DNA-biotin oligonucleotides comprise a poly$(dC)_{40}$ background in which Gs are inserted between positions 8 and 14 relative to the 3' end. The oligonucleotides were synthesized by the DNA/Peptide Core Facility (University of Utah) and the biotin linker phosphoramidite was purchased from Glen Research, Va. The presence of biotin and the purity of the samples were determined by gel electrophoresis prior to ion channel measurements. The four oligonucleotides shown in FIG. 14, along with biotin tethers, have been synthesized, characterized, and employed in ion channel measurements.

Figure 16:
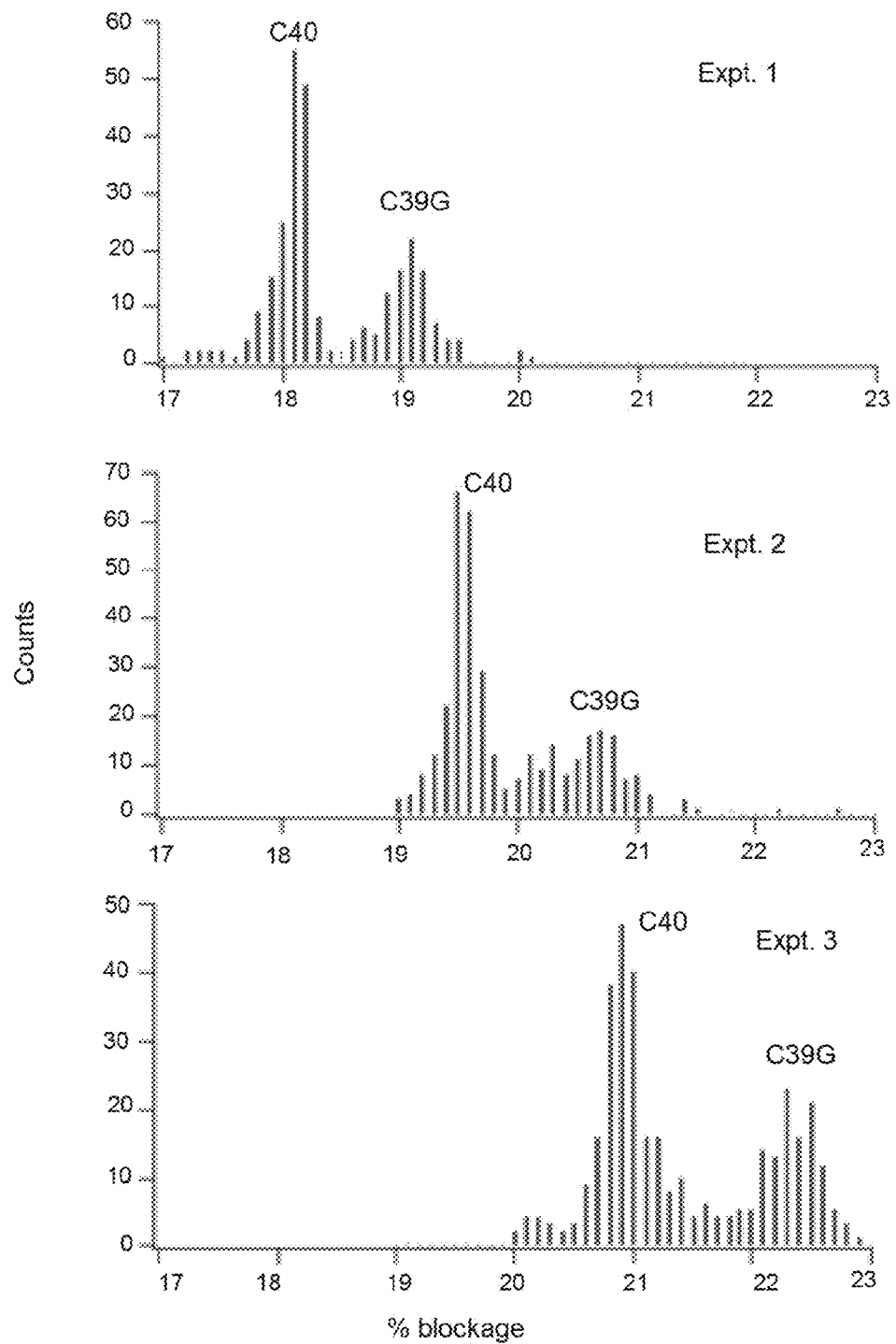
FIG. 16 shows current blockade distribution data obtained in three different experiments in accordance with an embodiment of the present invention.

FIG. 15 shows a typical i-t trace corresponding to the capture of the straptavidin-biotin DNA complex containing both $C_{40}$ and $C_{39}G_{\omega 14}$ oligomers. Measurements were made in 1 M KCl, 25 mM tris, and 1 mm EDTA solutions. Straptavidin-biotin DNA was captured from the cis side at negative voltage, and removed from the channel by reversing the polarity. Typically, several hundred events were recorded in each experiment using a single protein. The bottom trace of FIG. 16 shows a comparison of blockage currents for $C_{40}$ and $C_{39}G_{\omega 14}$ obtained in one experiment using the same α-HL channel. Insertion of the single G at position 14 results in a ~1 pA difference in the electrical signature, in agreement with the order of magnitude differences observed for single base substitutions.

FIG. 16 shows current blockade distributions obtained in three different experiments, each experiment employing a different ion channel. In these experiments, $C_{40}$ was added to the solution and blockades recorded, followed by adding $C_{39}G_{\omega 14}$ and recording current blockades for the mixed $C_{40}/C_{39}G_{\omega 14}$ solution. In this manner, the level of the current blockages for each oligomer can be determined. The higher blockage is likely associated with $C_{40}$ and the lower blockade with $C_{39}G_{\omega 14}$ (i.e., the channel conductivity is ~1.2% higher when one G is substituted at the 14 position). Table 1 summarizes the blockage currents of $C_{40}$ and $C_{39}G_{\omega 14}$, relative to the open channel current, as well as the relative difference in blockage currents. While the relative difference in normalized current between $C_{40}$ and $C_{39}G_{\omega 14}$ is independent of the ion channel (~1.2%), the normalized currents vary by as much as 3% using different ion channels, in agreement with previous literature reports.

This demonstrates the ability to differentiate single base substitutions based on the ion channel conductivity. These measurements can be extended to oligomers in which a single G is substituted at different positions, to multiple G substitutions, and to chemically modified DNA (e.g., oxidized G, halogenation and cis-platin adducts).

TABLE 1

| Blockage Currents for C40 and C39G. | | | | |
|---|---|---|---|---|
| Experiment # | T(° C.) | # events | % Blockage | Δ(% Blockage) |
| 1 | 22.2 | 265 | C40 18.1 ± 0.1 | 1.1 ± 0.2 |
| | | | C39G 19.2 ± 0.1 | |
| 2 | 21.9 | 379 | C40 19.5 ± 0.1 | 1.2 ± 0.2 |
| | | | C39G 20.7 ± 0.1 | |
| 3 | 21.9 | 354 | C40 21.0 ± 0.1 | 1.4 ± 0.2 |
| | | | C39G 22.4 ± 0.1 | |

Example 2

Strep-BTN Tethering Experiments

Figure 17:
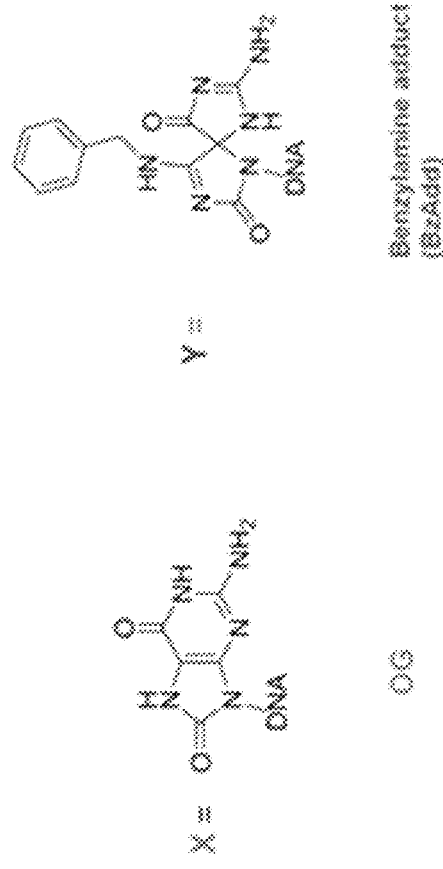
FIG. 17 is a schematic depiction of molecules (SEQ ID NOs 1, 5, 4, 6, and 7) employed in channel experiments in accordance with an embodiment of the present invention.

The following molecules were analyzed using a Strep-BTN linker to immobilize ssDNA within an αHL channel, as a means of distinguishing between single bases in the immobilized strand. The modifications were at either position ω8 or ω14. C40-Btn was used as the control DNA sample, and modifications upon the C40 strand produced OG or a benzylamine adduct (BzAdd) at position ω8 (Strep-BTN C8OG and Strep-BTN C8OG BzAdd, respectively) or position ω14 (Strep-BTN C14OG and Strep-BTN C14OG BzAdd, respectively). Structures for the molecules are shown in FIG. 17. Note that it is expected that the ω8 position to be in the vestibule at the entrance to the constriction zone and that ω14 is in the constriction zone of the channel.

Strep-BTN-ssDNA molecules were driven into the channel, held to collect a current signal, and released by reversing the applied potential polarity; this cycle was repeated to obtain a population of current blockage events. All data were taken with +/− 120 mV applied potential unless otherwise specified.

Strep-BTN C8OG and Strep-BTN C8OG BzAdd

Figure 18:
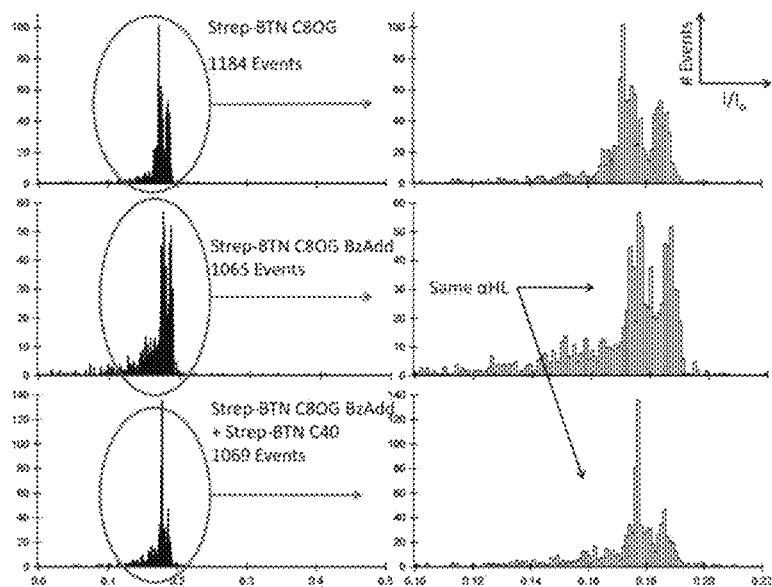
FIG. 18 shows data from channel experiments involving Strep-BTN C8OG and Strep-BTN C8OG BzAdd in accordance with an embodiment of the present invention.

Primary amine adducts to oxidized G residues are synthesized by treating synthetic oligonucleotides containing 8-oxoG with a primary amine in the presence of a mild oxidant such as $Na_3Fe(CN)_6$ or $Na_2IrCl_6$. For example, BTN C8OG BzAdd was synthesized from a 3'-biotinylated 40mer in which one nucleotides was replaced with the OG nucleotide as shown above. Additionally, these adducts can be prepared directly from G-containing oligomers by treatment with $Na_2IrCl_6$ or singlet oxygen in the presence of the primary amine. Initially, an experiment containing Strep-BTN C8OG was performed, and it resulted in a two-peak distribution of $I/I_o$ at 0.17 and 0.19. Next, in a separate experiment, data were collected for Strep-BTN C8OG BzAdd, and using the same protein, Strep-BTN C8OG was added to the same solution and data were again collected. Strep-BTN C8OG BzAdd showed peaks similar in $I/I_o$ position to Strep-BTN C8OG, and when the mixed solution was analyzed, molecules could not be cleanly distinguished from their $I/I_o$ values. A summary of the results for Strep-BTN C8OG and Strep-BTN C8OG BzAdd are presented in FIG. 18. To the left are plots showing the residual currents, and to the right are enlarged plots emphasizing peak position between the samples.

Strep-BTN C14OG and Strep-BTN C14OG BzAdd

Figure 19:
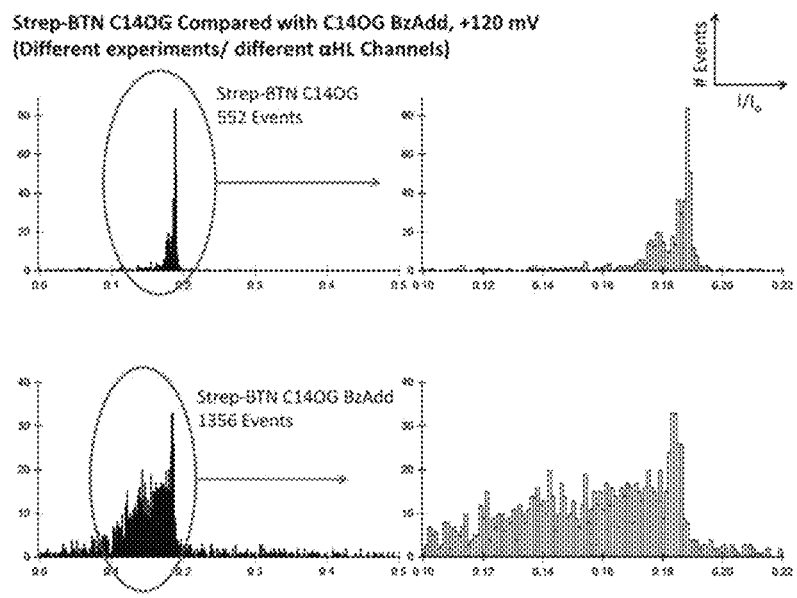
FIG. 19 shows data from channel experiments involving Strep-BTN C14OG and Strep-BTN C14OG BzAdd in accordance with an embodiment of the present invention.

Experiments were also performed with Strep-BTN C14OG and Strep-BTN C14OG BzAdd. Strep-BTN C14OG capture produced a similar result to Strep-BTN C8OG, there were two $I/I_o$ peaks at roughly 0.17 and 0.19. In a second experiment, Strep-BTN C14OG BzAdd was analyzed and showed a remarkably different $I/I_o$ profile, with blocking events distributed from 0.05 to 0.19. The results are summarized in FIG. 19.

Figure 20:
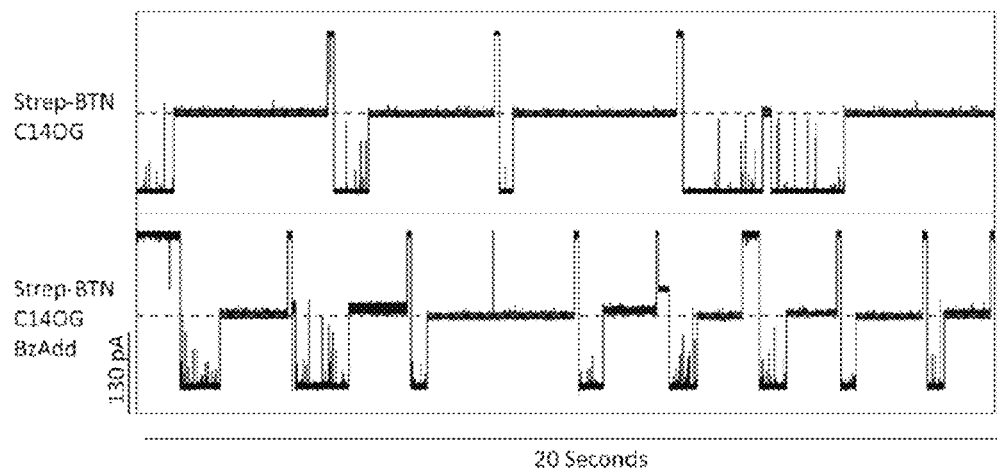
FIG. 20 shows data from channel experiments involving Strep-BTN C14OG and C14OG BzAdd in accordance with an embodiment of the present invention.

Example i-t traces are shown below in FIG. 20 for both Strep-BTN C14OG (top) and C14OG BzAdd (bottom). From the i-t traces it is apparent that the different current blockage levels can be attributed to distinct levels in the signal, rather than a noisy signal. However, there some blocked current signals that are noisy reflecting the dynamic motion of the adducted DNA within the channel. Such noise can be used to identify the presence and structure of the adduct.

Figure 21:
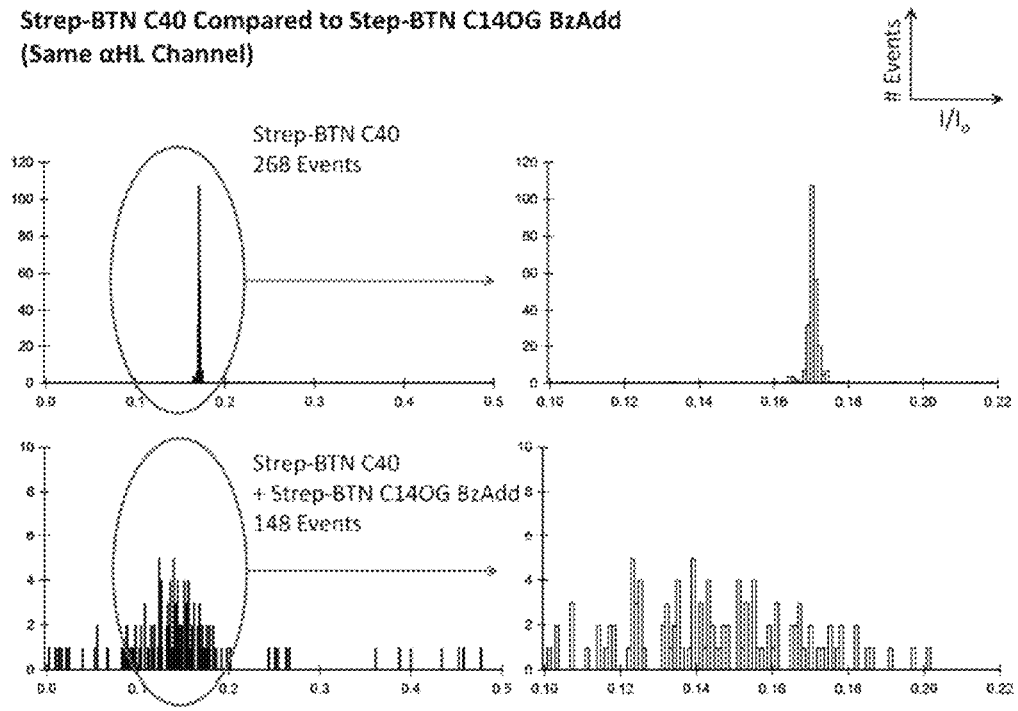
FIG. 21 shows data from channel experiments involving Strep-BTN C40 and Strep-BTN C14OG BzAdd in accordance with an embodiment of the present invention.

To further illustrate the distinctive signal produced by Strep-BTN C14OG BzAdd and to reproduce previous results, an experiment was performed to directly compare the signal against Strep-BTN C40. Strep-BTN C40 data were collected, and to the solution (using the same channel) the Strep-BTN C14OG BzAdd sample was added and additional data was recorded. Similar to previous results, Strep-BTN C40 produced a single $I/I_o$ peak, around 0.17, and the Strep-BTN C14OG BzAdd produced a widely distributed population of events, FIG. 21.

Figure 22:
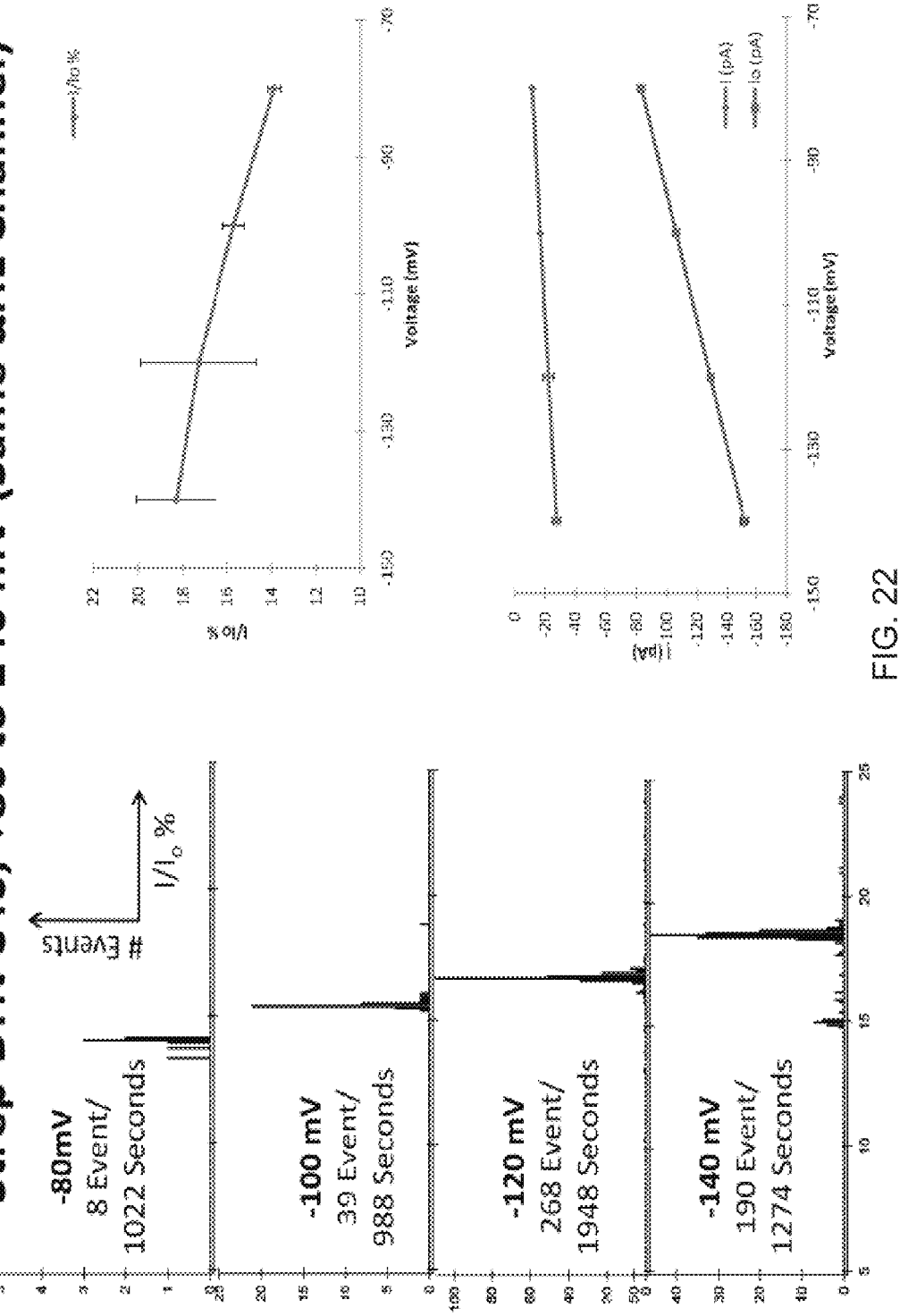
FIG. 22 shows data from channel experiments involving Strep-BTN C40 in accordance with an embodiment of the present invention.

Dependence of Blocking Current on Applied Voltage in the Strep-BTN DNA Tethered Experiments Further work was done to characterize the dependence of the blocking current on the applied voltage. In these experiments, Strep-BTN C40 was captured and the blocking current measured from 80 to 140 mV applied bias. It was found the $I/I_o$ for Strep-BTN C40 shifts to larger values at larger applied voltages (FIG. 22). When discrete values of I and $I_o$ were examined separately, it was found that extrapolation of the current values in the range 80 to 140 mV, to 0 mV applied voltage, yielded large and significantly different intercepts (~9 and 7 pA for the open and DNA blocked channel).

Figure 23:
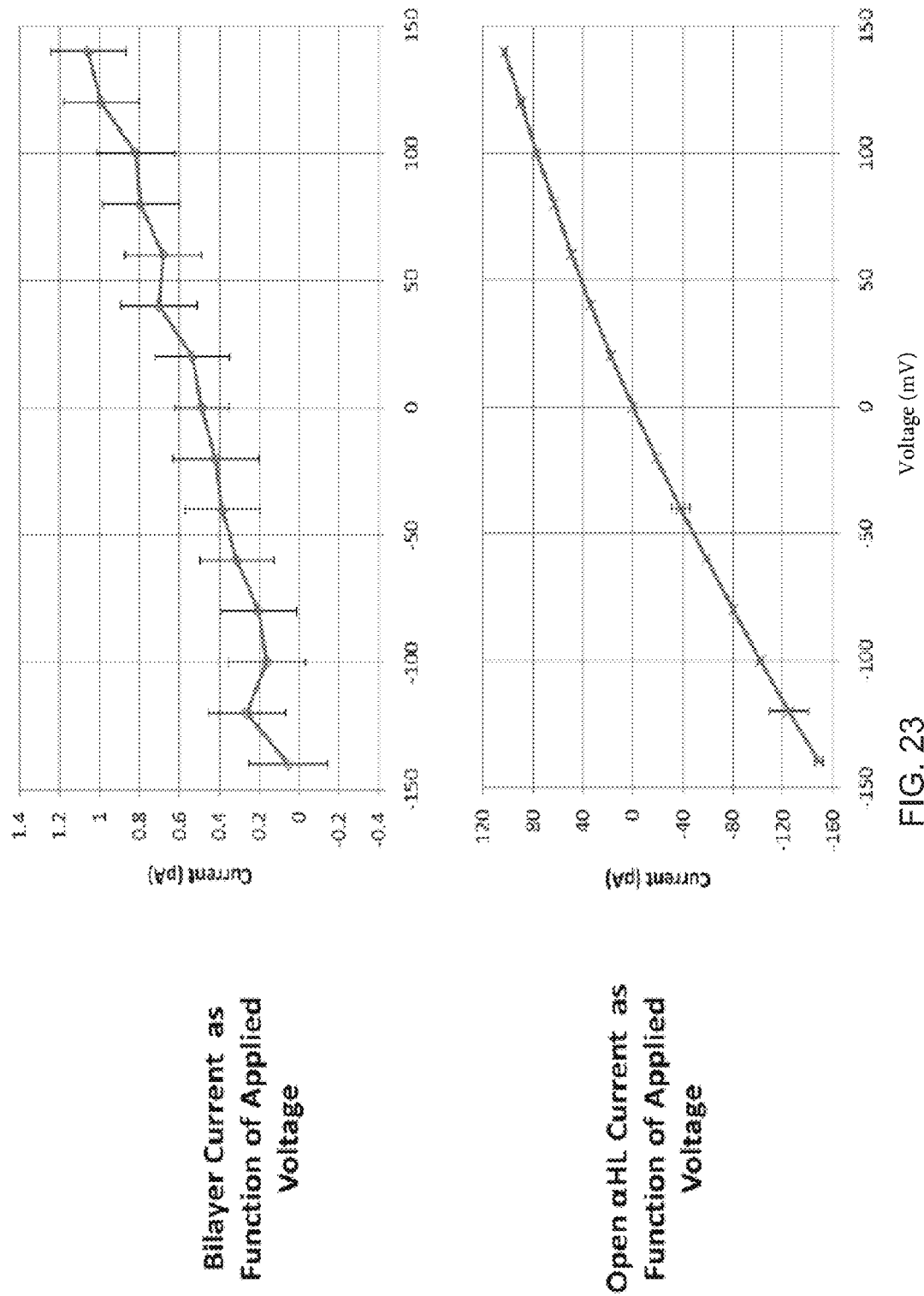
FIG. 23 shows data from channel experiments involving an open αHL channel in accordance with an embodiment of the present invention.

In further experiments, i-t traces were recorded for a bilayer and an open αHL channel, FIG. 23. (Note that the bilayer data analyzed correspond to the bilayer directly preceding the channel insertion data that is also presented here in FIG. 23.) Current was recorded between −140 mV to +140 mV at 20 mV increments, including 0 mV. Both experiments demonstrate that the 0 mV applied current is less than 1 pA. More importantly, the i-V trace for the open channel shows rectifying behavior. Extrapolating to zero bias, using only the current values between 80 and 140 mV, yields a zero bias offset of ~12 pA. A similar experiment to compare the extrapolated offset with the measured value while the channel is blocked is impossible, because the DNA does not remain in the channel at 0 bias. However, it is clear that dependence of the blocking current, $I/I_o$, on the applied voltage is real and is due to the non-linear i-V behavior of ion channel. (For the open channel, this is demonstrated, as described above; for the blocked channel, it is likely that some rectification also occurs). It is noted that $I/I_o$ values for different DNA molecules be compared at the same voltage.

Example 3

Additional Strep-BTN Tethered Experiments Using Modified DNA

Figure 24:
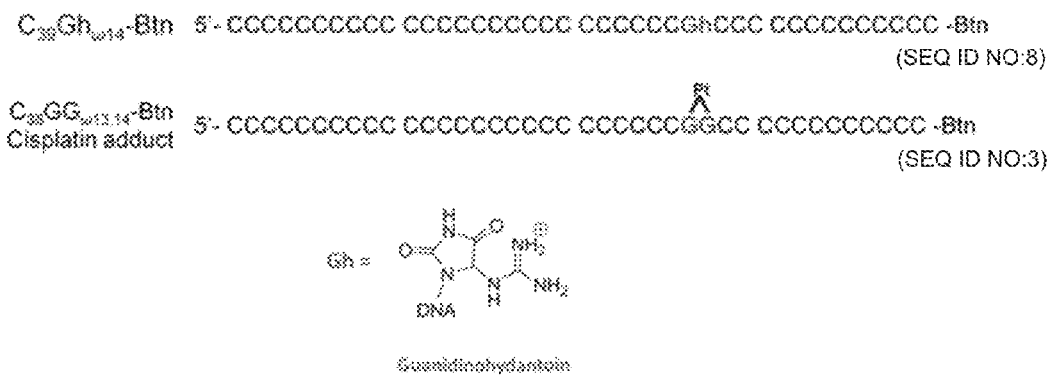
FIG. 24 is a schematic depiction of molecules (SEQ ID NOs 8 and 3) employed in channel experiments in accordance with an embodiment of the present invention.

One of the goals is to investigate chemical modifications of DNA bases that could help distinguish between bases or between runs of the same base. The following modified DNA molecules shown in FIG. 24 were analyzed using the Strep-BTN attachment to immobilize ssDNA within an αHL channel. Modification is at position ω14 for Gh and at ω13 and 14 for the Pt adduct, where ω refers to the 3' end of the strand. Synthesis and preliminary characterization of the cis-platin DNA complex was previously described. The guanidinohydantoin structure (Gh) is a derivative of guanine produced by oxidation.

Figure 25:
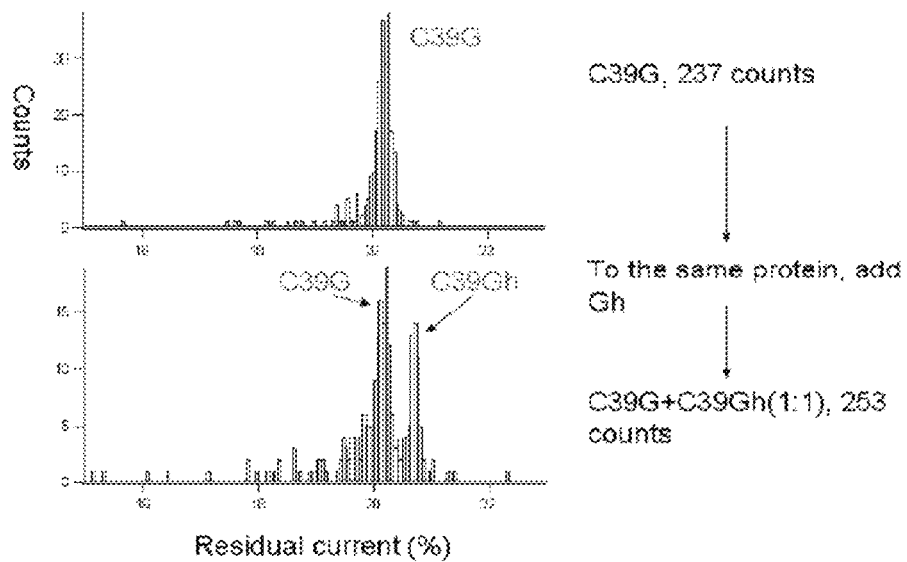
FIG. 25 shows data representing residual current distribution of $C39G_{\omega 14}$ and a mixed $C39G_{\omega 14}G/C39Gh_{\omega 14}$ solution recorded using the same protein channel in accordance with an embodiment of the present invention.

FIG. 25 shows the residual current distribution of $C39G_{\omega14}$ and a mixed $C39G_{\omega14}/C39Gh_{\omega14}$ solution recorded using the same protein channel. $C39G_{\omega14}$ was first added to the cell, and the current trace was recorded. $C39Gh_{\omega14}$ was then added to the solution and an additional current trace recorded for the mixed $C39G_{\omega14}/C39Gh_{\omega14}$ solution. The results demonstrate that $C39G_{\omega14}$ can be readily distinguished from $C39Gh_{\omega14}$.

FIG. 26 shows a control study on residual currents of $C38GG_{\omega13,14}$ and mixed $C38GG_{\omega13,14}/C38GG_{\omega13,14}Pt$. $C38GG_{\omega13,14}$ was added to the cell, followed by the addition of $C38GG_{\omega13,14}$ Pt to the same protein channel. There is no significant separation between $C38GG_{\omega13,14}$ and $C38GG_{\omega13,14}$ Pt in terms of their residual current levels.

In an additional experiment, poly(dC)$_{40}$ was added to the C38GG$_{\omega13,14}$/C38GG$_{\omega13,14}$ Pt mixture. The mixture is associated with a lower blockage compared with the homopolymer.

Example 4

Ion Channel Recording with GNM

The glass nanopore membrane (GNM) is a sealed glass capillary with a single, conically shaped pore embedded within the glass membrane as shown in FIG. 27. The GNM acts as the solid support for a lipid bilayer following surface modification with 3-cyanopropyldimethlychlorosilane. αHL is reconstituted in the bilayer for ion channel measurements.

Tethered DNA Ion Channel Recordings

Single-stranded DNA can be linked to a biotin (BTN) molecule and bound to streptavidin (Strep); this results in DNA capture and immobilization within the αHL ion channel. As a result of increased residence time within the αHL channel, the signal resolution is improved and the bases within the channel can be distinguished based on blockage current levels.

Figure 28:
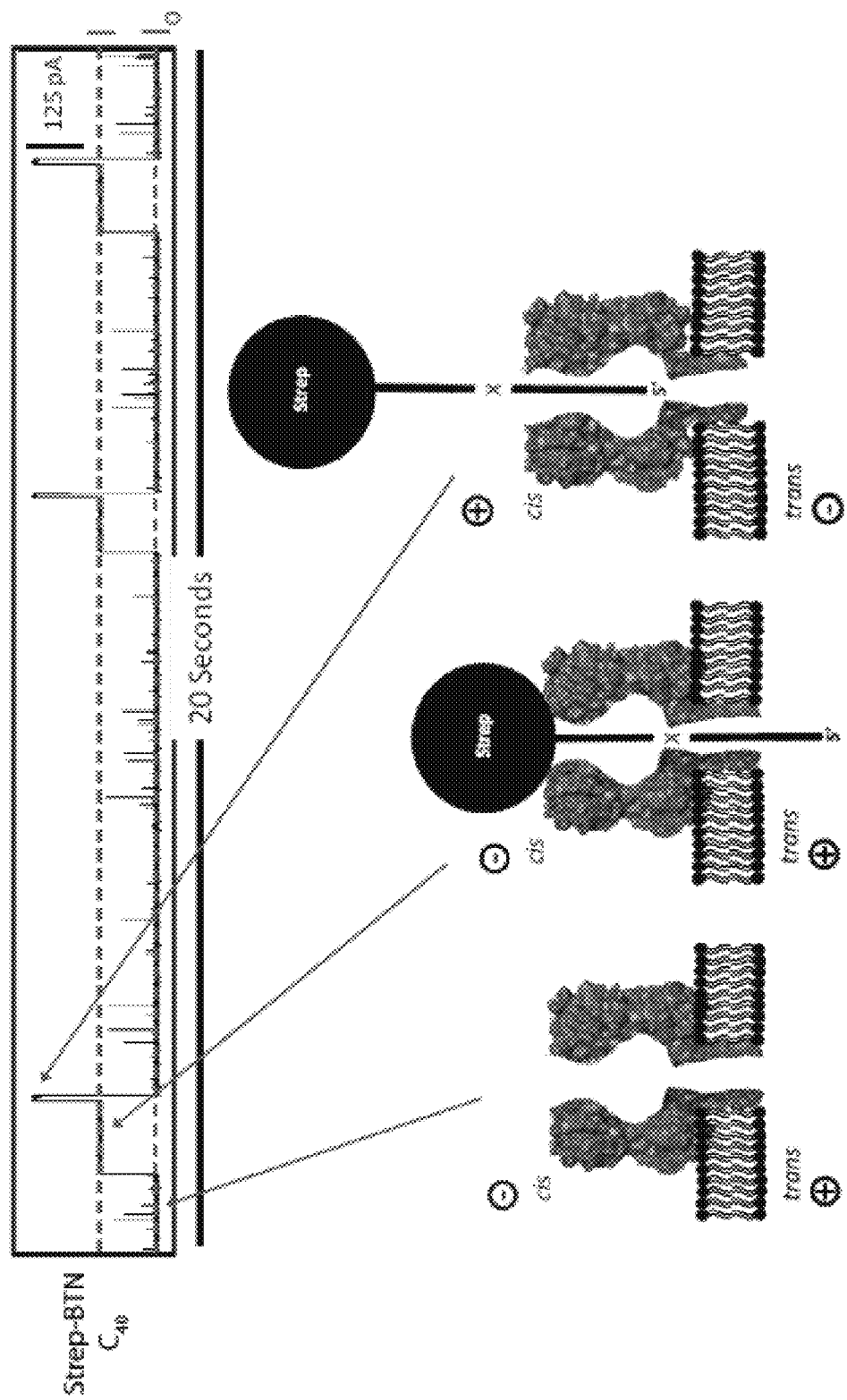
FIG. 28 is a schematic diagram of Strep-BTN DNA driven into a channel including data showing the open channel current (Io) and the blocked current (I) of the channel in accordance with an embodiment of the present invention.

The Strep-BTN DNA is driven into the αHL by an applied voltage (−120 mV cis), captured, and released by a reversal of the applied voltage (+120 mV cis). The current values for the open channel current (Io) and the blocked current (I) are measured and used to determine the percent residual current (% I/Io). Histograms are generated for the values of % I/Io and compared between molecules to determine how base modifications influence the current blockage level as illustrated in FIG. 28.

DNA Base Modification

Although the tether technique allows the native bases to be distinguished, the difference in the % I/Io is only 1-2%, and increasing this difference would further improve sequencing efforts. The DNA nucleotide that resides within the αHL constriction can be modified to significantly amplify differences in % I/I$_0$, allowing base-by-base molecule identification. Results presented use the capture technique for a Strep-BTN dC40 that is modified at position ω14.

DNA Base Detection

Guanine in the ω14 position of poly-dC39 results in ~1% higher blockage current compared to the homopolymer, dC40. Modification of the guanine residue through oxidation can be used to add a bulky adduct, which can change the current signal by more than 5%, resulting in a significantly different current blockage histogram compared to the native bases, making it easily distinguishable. The following is an example of how powerful base modification can be for discerning between bases, especially when the chemistry used for modification is base specific; the i-t trace for a Strep-BTN C40 is compared to a molecule where the ω14 position has been modified to contain a benzylamine (Bz) adduct, C39Bzω14. The adduct changes the current level as well as current fluctuations associated with individual capture events. The ability to control the current signal (both magnitude and noise) in a base specific manner has many implications for DNA sequencing.

Experiments were performed with the following conditions: bilayers were painted on GNMs with 10 mg DPhPC per mL decane, 1 M KCl, 25 mM Tris-HCl, 1 mM EDTA (pH 7.9) was used as the buffered electrolyte, ~200 nM Strep-BTN DNA was present in the experimental cell, and +/−120 mV was used to capture/release the molecule. DNA molecules were attached to the BTN using a tether.

Analysis and Discussion

Figure 29:
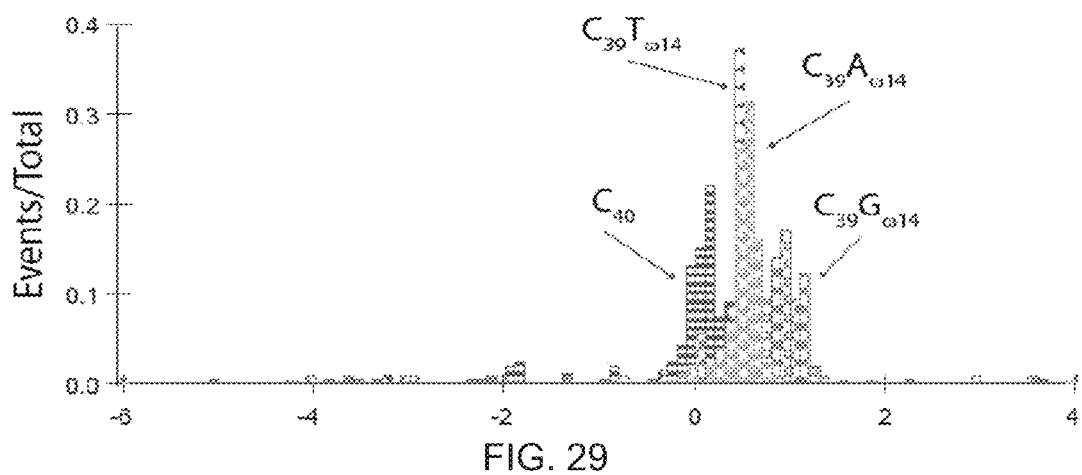
FIG. 29 shows data representing the mean percent current blockage for the native DNA bases, C, T, A, and G, at position $\omega_{14}$ in accordance with an embodiment of the present invention.

The plot shown in FIG. 29 shows the mean percent current blockage for the native DNA bases, C, T, A, and G, at position ω14. The % I/Io peak positions are 0±0.2, 0.4±0.1, 0.5±0.1, and 0.9±0.2, for C40, C39Tω14, C39Aω14, and C39Gω14, respectively (the current blockage for C40 is used as the reference position, 0% I/Io, in all plots).

Figure 30:
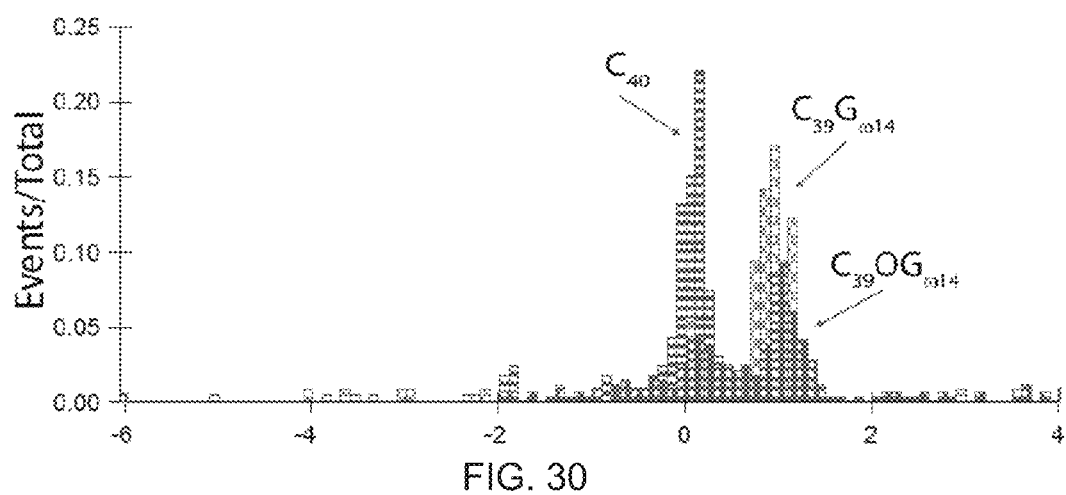
FIG. 30 shows data representing the mean percent current blockage for G compared to OG at position ω14 in channel experiments in accordance with an embodiment of the present invention.
Figure 31:
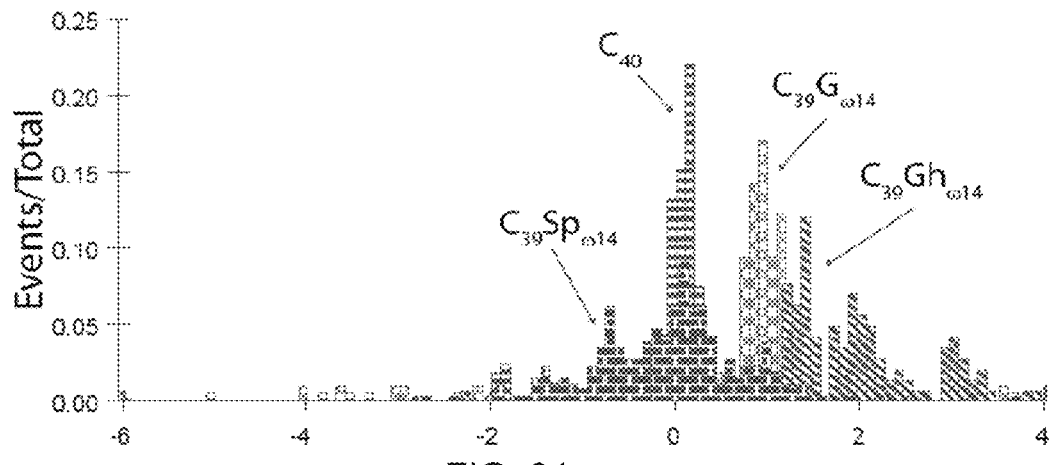
FIG. 31 shows data representing the mean percent current blockage for the base modifications Sp and Gh in channel experiments in accordance with an embodiment of the present invention.

Oxidation of G to OG at position ω14 does not result in a significant shift in peak position relative to C39Gω14 as shown in FIG. 30. Further oxidation of OG yields the base modifications Sp and Gh, and shifts the current blockage peak position away from the C39Gω14 peak as seen in FIG. 31. C39Ghω14 has a peak shifted to higher % I/Io values, while the peak for C39Spω14 is shifted to lower values. The higher current for C39Ghω14 likely reflects the higher charge and flexibility compared to C39Spω14.

Figure 32:
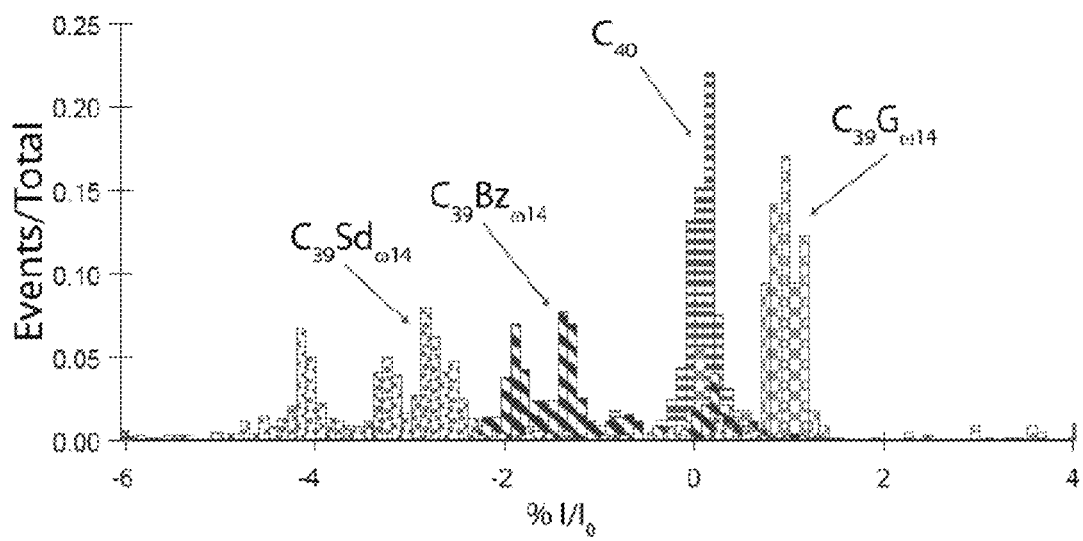
FIG. 32 shows data representing the mean percent current blockage for C39Gω14, C39Bzω14, and C39Sdω14 in channel experiments in accordance with an embodiment of the present invention.

The oxidation of guanine and the addition of an adduct result in large peak shifts away from the position of C39Gω14, by as much as ~5% as seen in FIG. 32. Both C39Bzω14 and C39Sdω14 are shifted to lower % I/Io values compared to C39Gω14, and reflect the presence of bulky adducts. The occurrence of multiple peaks here is attributed to multiple possible conformations of the molecule within the channel; both C39Bzω14 and C39Sdω14 have a chiral center and contain diastereomer pairs.

Example 5

Nanopore Detection of 8-Oxo-7,8-Dihydro-2'-Deoxyguanosine

Reagents for Adduct Synthesis.

Gly-Pro-Arg-Pro amide, spermine, spermidine, benzylamine, D-(+)-glucosamine, N$^\alpha$-acetyllysine methyl ester hydrochloride, and Na$_2$IrCl$_6$, were purchased from commercial suppliers and used without further purification.

DNA Preparation and Purification Procedures.

The 3'-biotinylated oligodeoxynucleotides (ODN) were synthesized from commercially available phosphoramidites (Glen Research, Sterling, Va.) by the DNA-Peptide Core Facility at the University of Utah. After synthesis, each ODN was cleaved from the synthetic column and deprotected according to the manufacturer's protocols, followed by purification using a semi-preparation ion-exchange HPLC column with a linear gradient of 25% to 100% B over 30 min while monitoring absorbance at 260 nm (A=20 mM Tris, 1 M NaCl pH 7 in 10% CH$_3$CN/90% ddH$_2$O, B=10% CH$_3$CN/90% ddH$_2$O, flow rate=3 mL/min) The identities and purities of the ODNs were determined by negative ion electron spray (ESI$^-$) on a Micromass Quattro II mass spectrometer equipped with Zspray API source in the mass spectrometry laboratory at the Department of Chemistry, University of Utah.

Synthesis of ODN-Hydantoin/ODN-Sp-NR Products.

The ODN-hydantoin/ODN-Sp-NR products were synthesized according to the following: the ODN-Gh products were produced by incubating OG-containing oligomers (10 µM, 1 nmole) in ddH$_2$O at 4° C. for 30 mM; 12 equivalents of Na$_2$IrCl$_6$ (120 µM, 12 nmoles) were titrated into the ODN samples. After a 30 min incubation, the reactions were terminated with Na$_2$EDTA (pH 8, 1 mM, 100 nmoles). The ODN-Sp products were synthesized by allowing the OG-containing oligomers (10 µM, 1 nmole) in 75 mM NaP$_i$ buffer (pH 7.4) to incubate at 45° C. for 30 min, followed by addition of 12 equivalents of Na$_2$IrCl$_6$ (120 µM, 12 nmoles), and $Na_2EDTA$ (pH 8, 1 mM, 100 nmoles) was used to quench the oxidant after the reactions proceeded for 30 min.

The syntheses of ODN-Sp-NRs were achieved by thermally equilibrating the OG-containing oligomers (10 μM, 1 nmole) and various amines (2 mM, 200 nmoles) in 75 mM NaPi buffer (pH 8.0) at 45° C. for 30 min; then 15 equivalents of $Na_2IrCl_6$ (150 μM, 15 nmoles) were titrated into the samples that were then left for 30 min. The reactions were quenched the same way as previously described.

All the products were purified by an analytical ion-exchange HPLC column with a linear gradient of 25% to 100% B over 30 min while monitoring absorbance at 260 nm (A=20 mM Tris, 1 M NaCl pH 7 in 10% $CH_3CN$/90% $ddH_2O$, B=10% $CH_3CN$/90% $ddH_2O$, flow rate=1 mL/min); see Table 2. ODN-Sp-spermine and ODN-Sp-spermidine products were used immediately due to their instability.

TABLE 2

Characterization of the oligonucleotides.

| Name | HPLC retention time (min) | Mass Expected | Mass Observed |
|---|---|---|---|
| $C_{40}$ | 14.5 | 12075.2 | 12075.3 |
| $C_{39}G_{\omega 14}$ | 14.4 | 12115.3 | 12116.7 |
| $C_{39}T_{\omega 14}$ | 14.4 | 12090.3 | 12089.6 |
| $C_{39}A_{\omega 14}$ | 14.4 | 12099.3 | 12099.2 |
| $C_{39}OG_{\omega 14}$ | 13.9 | 12131.3 | 12131.2 |
| $C_{39}Sp_{\omega 14}$ | 14.2/14.5 | 12147.3 | $12163.2^a$ |
| $C_{39}Gh_{\omega 14}$ | 13.7 | 12121.3 | $12137.5^a$ |
| $C_{39}Bz_{\omega 14}$ | 13.4 | 12236.4 | 12236.8 |
| $C_{39}GlcN_{\omega 14}$ | 12.7 | 12308.5 | 12308.8 |
| $C_{39}Spd_{\omega 14}$ | 12.9 | 12274.6 | 12276.8 |
| $C_{39}Spm_{\omega 14}$ | 12.8 | 12331.7 | NA |
| $C_{39}Lys_{\omega 14}$ | 13.9/14.1 | 12331.4 | $12348.0^a$ |
| $C_{39}GPRP_{\omega 14}$ | 11.3/11.9 | 12553.8 | 12553.6 |
| $KrasG_{\omega 14}$ | 12.0 | 12864.1 | 12864.8 |
| $KrasOG_{\omega 14}$ | 12.0 | 12880.1 | 12880.0 |
| $KrasSp_{\omega 14}$ | 12.1/12.2 | 12896.1 | 12895.2 |
| $KrasGh_{\omega 14}$ | 11.5/11.7 | 12870.1 | $12885.9^a$ |
| $KrasSpm_{\omega 14}$ | 10.8 | 13030.4 | NA |

NA: not available due to instability of the adduct.
$^a$Products showed oxidation of the biotin during synthesis.

Chemicals and Materials.

Aqueous solutions mentioned below were prepared using >18 MΩ·cm ultrapure water from a Barnstead E-pure water purifier. KCl (Sigma-Aldrich), trizma base (Sigma-Aldrich), EDTA (Mallinckrodt Chemicals), and HCl (EMD) were used as received. A buffered electrolyte solution of 1.0 M KCl, 25 mM Tris-HCl, and 1.0 mM EDTA (pH 7.9) was prepared and used for all ion channel recording measurements. The buffered electrolyte solution was filtered using a sterile 0.22 mm Millipore vacuum filter (Fisher Scientific). The wild type protein channel α-hemolysin (αHL), isolated from *Staphylococcus aureus* as a monomer, was obtained as a lyophilized powder from List Biological Laboratories and stored at concentration of 0.5 mg αHL per mL ultra pure water in a −20° C. freezer. Upon use, the αHL solution was diluted to a concentration of 0.05 mg αHL per mL using the above mentioned buffered electrolyte and added directly to the experimental cell. The phospholipid 1,2-diphytanoyl-sn-glycero-3-phosphocholine (DPhPC) was purchased from Avanti Polar Lipids as a powder and stored in a −20° C. freezer. Upon use, the DPhPC powder was dispersed in decane (Fisher Scientific) to a concentration of 10 mg DPhPC per mL decane. Glass nanopore membranes (GNMs) were fabricated, and before use as a bilayer support, were silanized in 2% (v:v) 3-cyanopropyldimethylchlorosilane in acetonitrile (Fisher Scientific) overnight. Ag/AgCl electrodes were prepared by soaking silver wire (0.25 mm diameter, Alfa Aesar) in bleach. All DNA oligomers studied were obtained as described above, and DNA molecule binding to streptavidin was achieved by mixing DNA and streptavidin at a 4:1 ratio and incubating at room temperature for 10 minutes.

Immobilization Ion Channel Recording Measurements.

Current-time (i-t) measurements were performed using a custom built high-impedance, low noise amplifier and data acquisition system (Electronic Bio Sciences, San Diego Calif.). Before use, a glass nanopore membrane (GNM) was rinsed with ethanol and ultra pure water, and finally filled with buffered electrolyte. The GNM was positioned within the EBS DC System via a pipette holder (Dagan Corporation), where the back end was sealed to a pressure gauge and 10 mL gas-tight syringe (Hamilton). An Ag/AgCl electrode wire was positioned inside the GNM and a second Ag/AgCl electrode was positioned in the experimental cell, external to the GNM. The same buffered electrolyte used to fill the GNM was added to the EBS DC System experimental cell, αHL was also added to the experimental cell (external to the GNM). Voltage was applied across the GNM orifice, cis vs. trans with respect to the αHL channel, and external vs. internal with respect to the GNM, and the resultant current was measured as a function of time.

Suspended bilayers were generated through painting. To form a suspended bilayer, a plastic pipette tip (gel-loading tips, flat, 1-200 μL, 0.4 mm) was filled with lipid solution and gently pulled across the GNM face, over the orifice. The establishment of a bilayer was confirmed by observing a drop in conductance as voltage was applied across the GNM orifice; an open pore has a resistance of approximately 10 MΩ, while a bilayer suspended across a GNM exhibits a resistance of around 100 GΩ. After bilayer formation, a pressure was applied to the back of the GNM for protein channel reconstitution to occur. Strep-Btn DNA was added to the cell in 100-200 nM increments. DNA was captured and held using an applied voltage of −120 mV (cis vs. trans), and released by reversing the bias. The modified sample of interest was added to the experimental cell first, and after an adequate number of blockage events are collected, a second control sample, Strep-Btn $C_{40}$, was added to the cell to provide a reference position. Data were collected with a 10 kHz low pass filter, and 50 kHz data acquisition rate.

DNA Immobilization Data Analysis.

Only capture events longer than 1 second were included in data analysis. All event current blockage values (I) were normalized by the immediately preceding open channel current ($I_o$), and expressed as % $I/I_o$. The Strep-Btn $C_{40}$% $I/I_o$ peak position was set as the reference position 0. % $I/I_o$ for all other molecules is reported relative to Strep-Btn $C_{40}$; more blocking % $I/I_o$ values are negative relative to Strep-Btn $C_{40}$ and less blocking % $I/I_o$ values are positive relative to Strep-Btn $C_{40}$.

Figure 33:
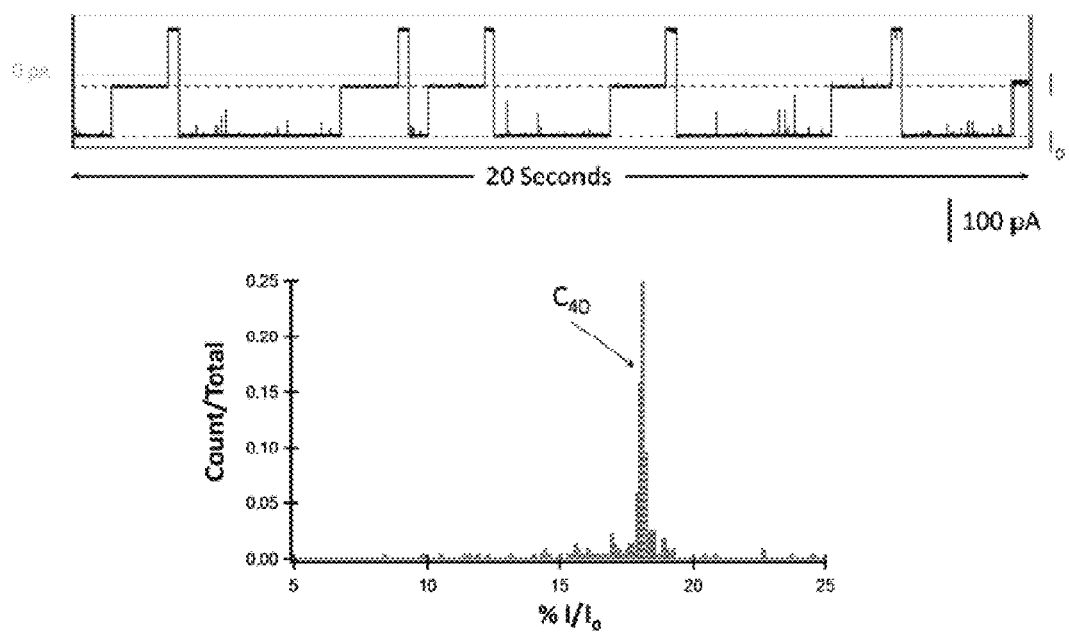
FIG. 33 shows an example i-t trace and % I/$I_o$ histogram for Strep-Btn $C_{40}$ in accordance with an embodiment of the present invention.

FIG. 33 shows an example i-t trace and % $I/I_o$ histogram for Strep-Btn $C_{40}$. Strep-Btn $C_{40}$ current blockages result in a single, sharp, prominent % $I/I_o$ peak. Strep-Btn $C_{40}$ consistently yielded a single, sharp % $I/I_o$ peak, and since all modifications discussed below are present within a $C_{40}$ background, Strep-Btn $C_{40}$ was used as a reference molecule. % $I/I_o$ histograms in the text and in the following figures for single-modified base substitutions are plotted relative to % $I/I_o$ for Strep-Btn $C_{40}$ peak position, which is assigned a value of 0.

Figure 34:
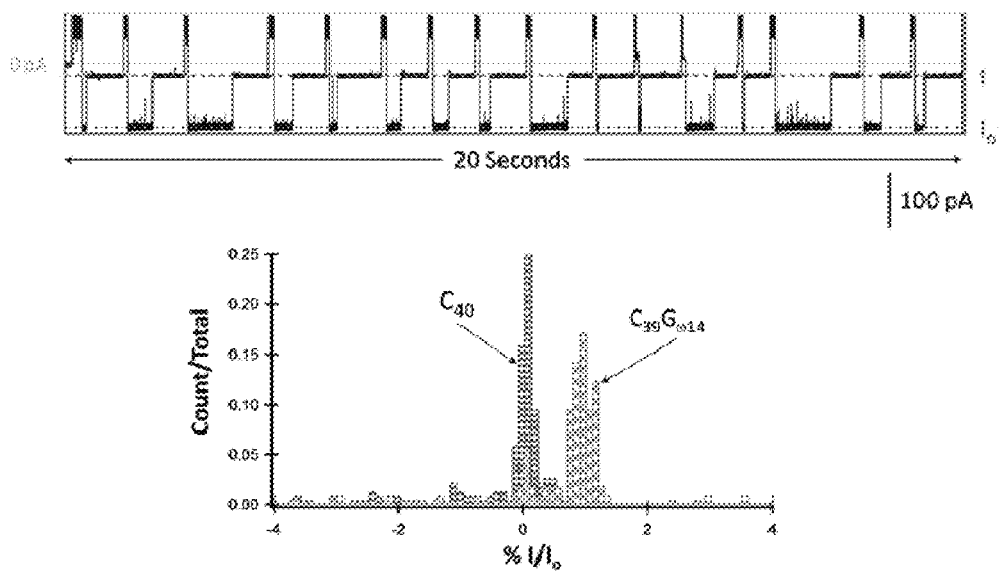
FIG. 34 shows an example i-t trace for Strep-Btn $C_{39}G_{\omega 14}$ and the resulting % I/$I_o$ histogram compared with Strep-Btn $C_{40}$ in accordance with an embodiment of the present invention.

FIG. 34 shows an example i-t trace for Strep-Btn $C_{39}G_{\omega 14}$ and the resulting % $I/I_o$ histogram compared with Strep-Btn $C_{40}$.

Figure 35:
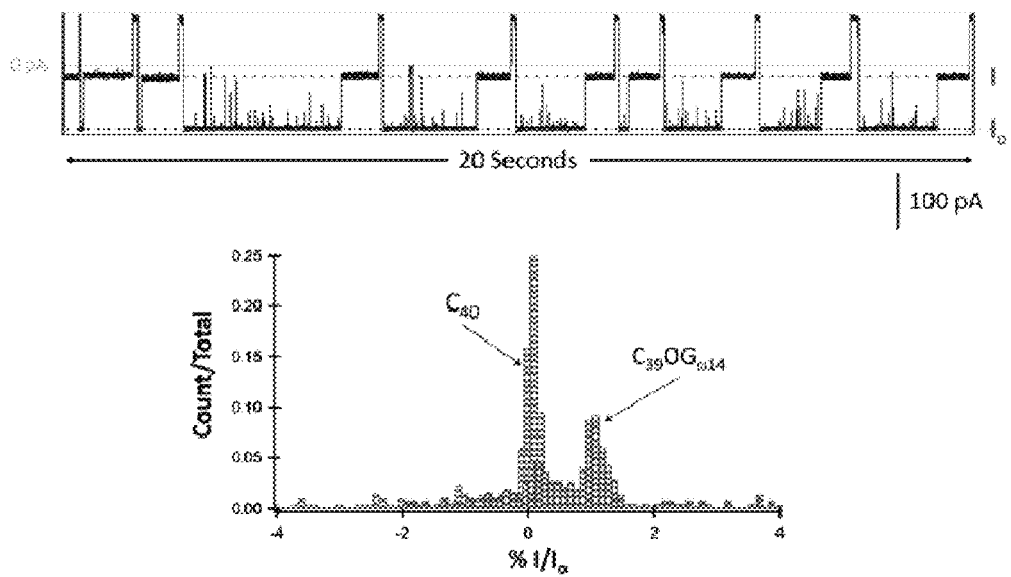
FIG. 35 shows an example i-t trace for Strep-Btn $C_{39}OG_{\omega 14}$ and the resulting % I/$I_o$ histogram compared with Strep-Btn $C_{40}$ in accordance with an embodiment of the present invention.

FIG. 35 shows an example i-t trace for Strep-Btn $C_{39}OG_{\omega 14}$ and the resulting % $I/I_o$ histogram compared with Strep-Btn $C_{40}$.

Figure 36:
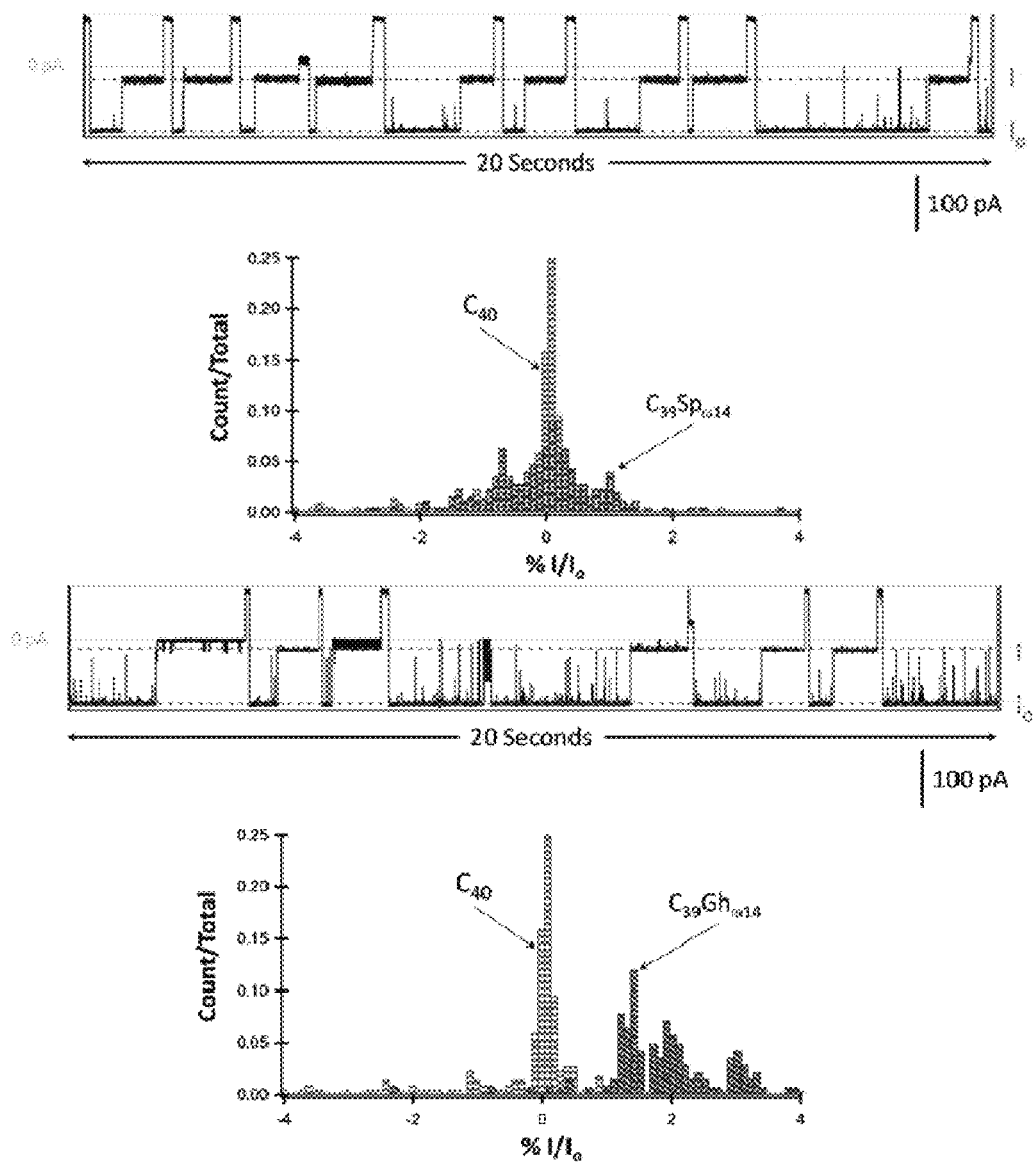
FIG. 36 shows example i-t traces for Strep-Btn $C_{39}Sp_{\omega 14}$ and Strep-Btn $C_{39}Gh_{\omega 14}$, and their respective % I/$I_o$ histograms compared with Strep-Btn $C_{40}$ in accordance with an embodiment of the present invention.

FIG. 36 shows example i-t traces for Strep-Btn $C_{39}Sp_{\omega 14}$ (upper) and Strep-Btn $C_{39}Gh_{\omega 14}$ (lower), and their respective % $I/I_o$ histograms compared with Strep-Btn $C_{40}$.

Figure 37:
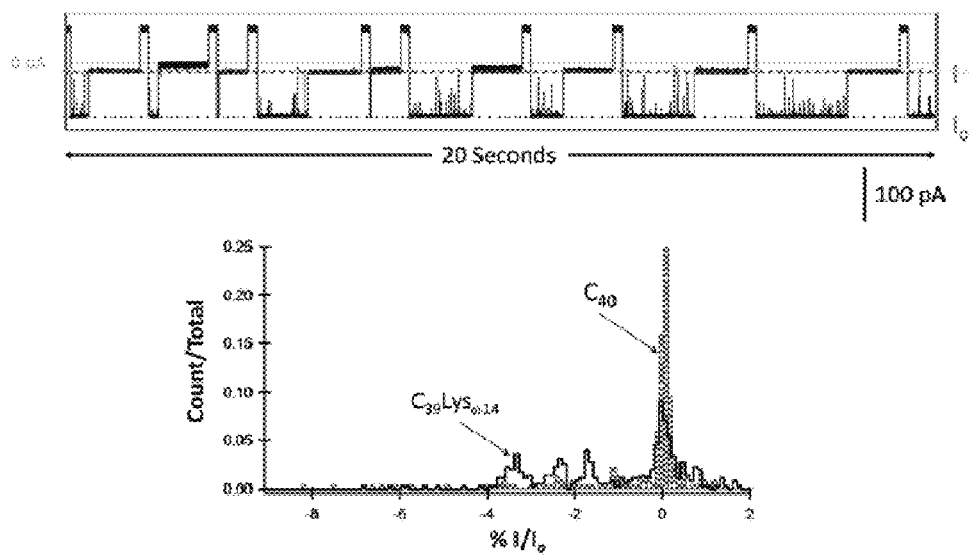
FIG. 37 shows an example i-t trace for Strep-Btn $C_{39}Lys_{\omega 14}$ and the resulting % I/$I_o$ histogram compared with Strep-Btn $C_{40}$ in accordance with an embodiment of the present invention.

FIG. 37 shows an example i-t trace for Strep-Btn $C_{39}Lys_{\omega 14}$ and the resulting % $I/I_o$ histogram compared with Strep-Btn $C_{40}$. The lysine adduct produced multiple current blockage levels and noise amplitudes.

Figure 38:
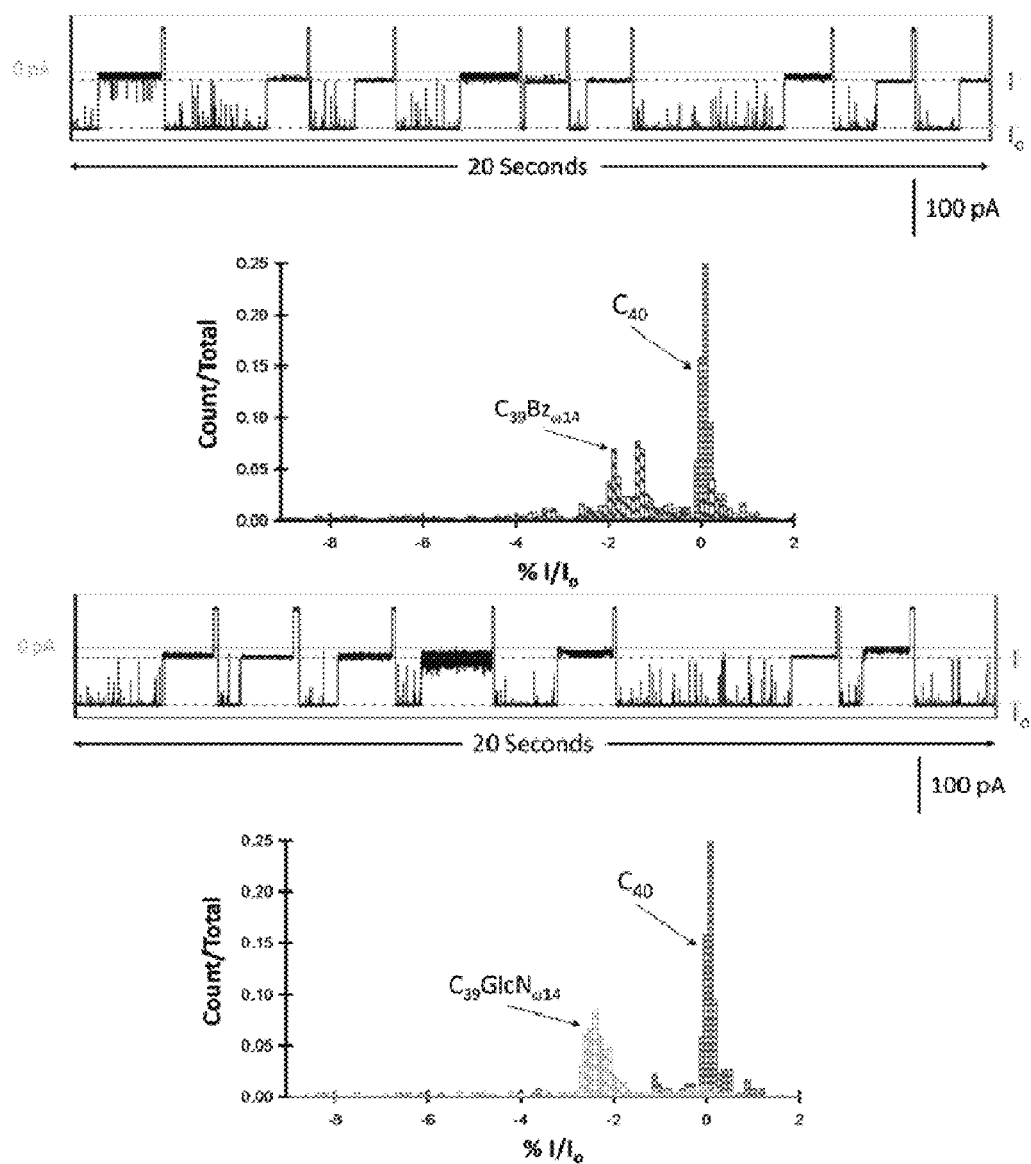
FIG. 38 shows example i-t traces for Strep-Btn $C_{39}Bz_{\omega 14}$ and Strep-Btn $C_{39}GlcN_{\omega 14}$ and the resulting % I/$I_o$ histograms compared with Strep-Btn $C_{40}$ in accordance with an embodiment of the present invention.

FIG. 38 shows example i-t traces for Strep-Btn $C_{39}Bz_{\omega 14}$ (upper) and Strep-Btn $C_{39}GlcN_{\omega 14}$ (lower) and the resulting % $I/I_o$ histograms compared with Strep-Btn $C_{40}$. Both adducts produced multiple current blockage levels and noise amplitudes. Although the glucosamine adduct is a six-membered ring similar to the benzylamine adduct, it contains hydroxyl groups and is not aromatic.

Figure 39:
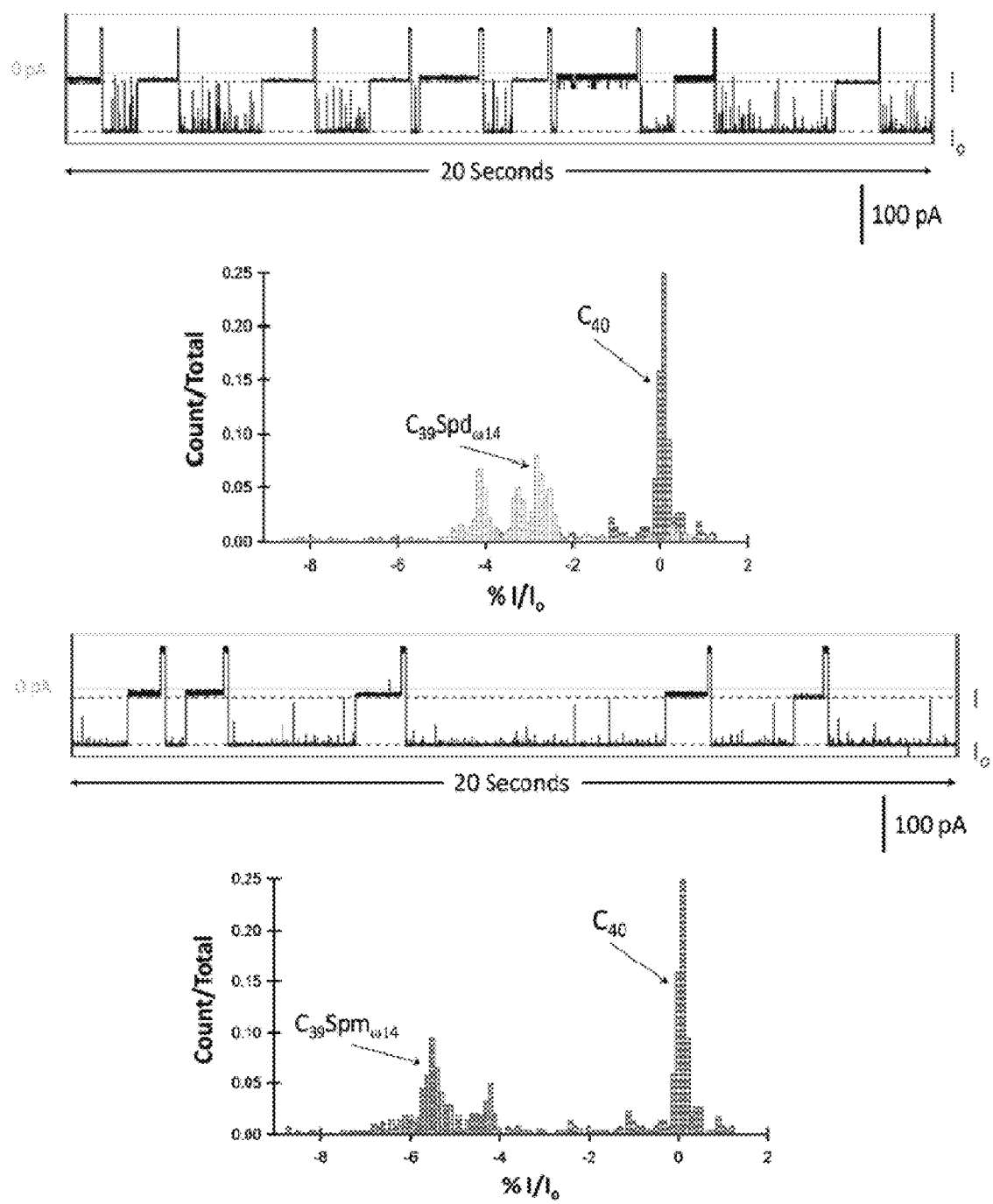
FIG. 39 shows example i-t traces for Strep-Btn $C_{39}Spd_{\omega14}$ and Strep-Btn $C_{39}Spm_{\omega14}$ and the resulting % $I/I_o$ histograms compared with Strep-Btn $C_{40}$ in accordance with an embodiment of the present invention.

FIG. 39 shows example i-t traces for Strep-Btn $C_{39}Spd_{\omega 14}$ (upper) and Strep-Btn $C39Spm_{\omega 14}$ (lower) and the resulting % $I/I_o$ histograms compared with Strep-Btn $C_{40}$. Both adducts are linear and contain amine groups, with spermine being the longer of the two. % $I/I_o$ histograms for both show multiple peak levels, but similar levels of noise. Both displayed less variable current blockage and noise levels relative to the cyclic adducts (Trp, Bz, and GlcN).

Figure 40:
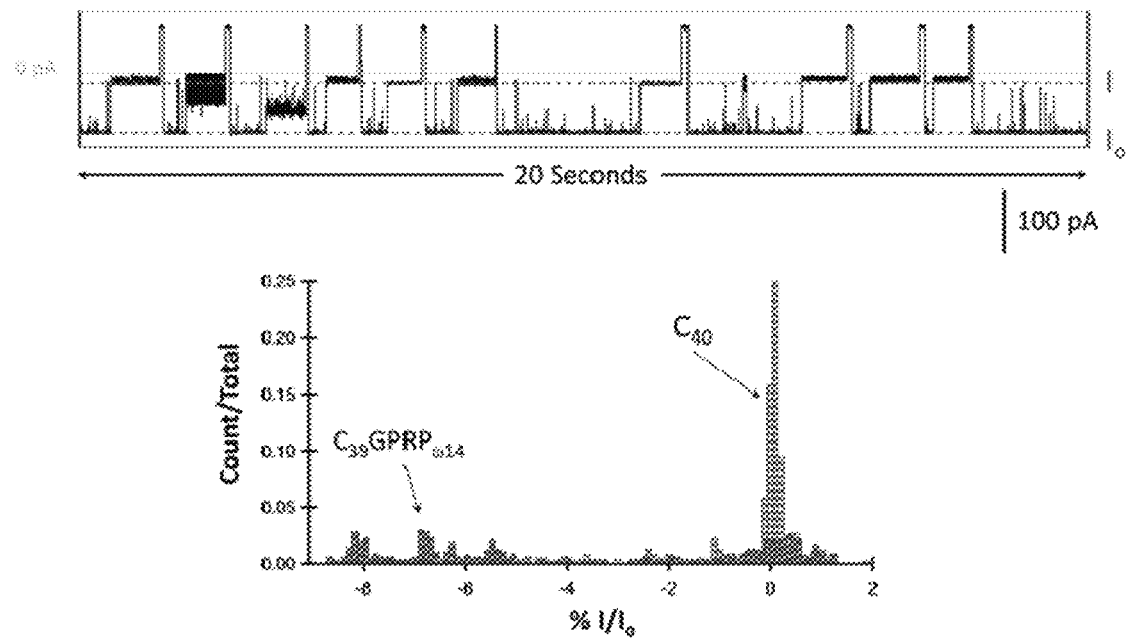
FIG. 40 shows an example i-t trace for Strep-Btn $C_{39}GPRP_{\omega14}$ and % $I/I_o$ histogram compared with Strep-Btn $C_{40}$ in accordance with an embodiment of the present invention.

FIG. 40 shows an example i-t trace for Strep-Btn $C_{39}GPRP_{\omega 14}$ and % $I/I_o$ histogram compared with Strep-Btn $C_{40}$. The glycine-proline-arginine-proline amide adduct produced the deepest current blockages events relative to other adducts in this study. There was a large spread in current blockage levels as well as noise amplitude, and a relatively strong peak % $I/I_o=0$. The presence of this peak may indicate that the molecule is too large to enter the sensing region of the αHL channel and the surrounding poly-dC sequence is being occasionally detected.

Figure 41:
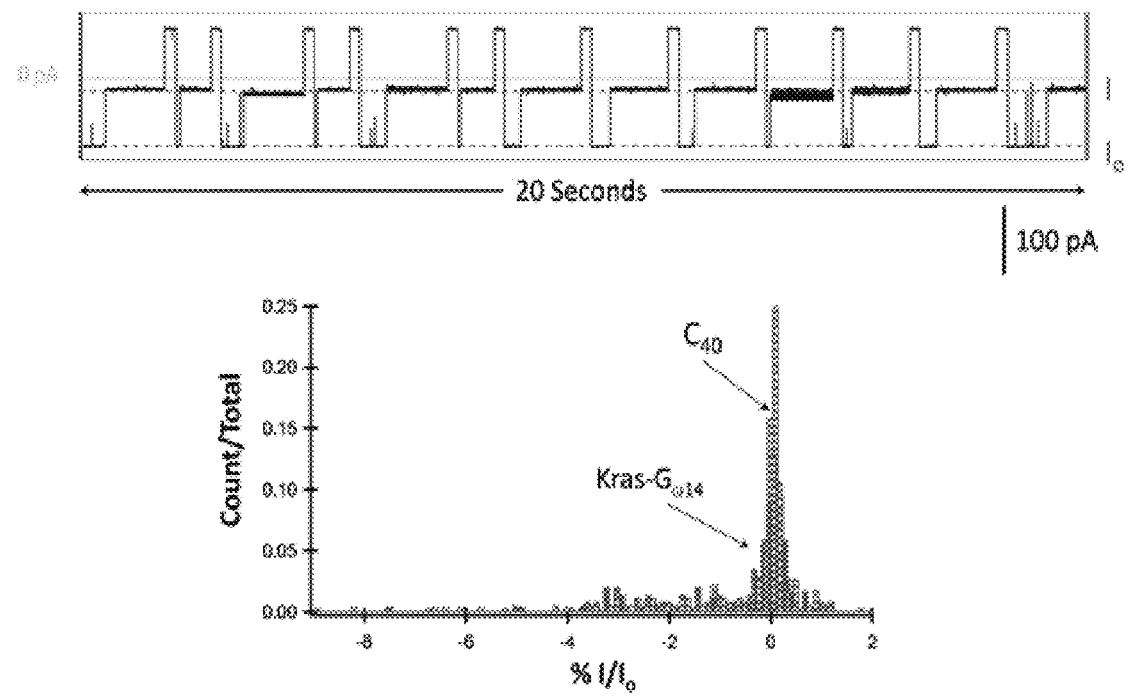
FIG. 41 shows an example i-t trace for Strep-Btn Kras-$G_{\omega14}$ and the resulting % $I/I_o$ histogram compared with Strep-Btn $C_{40}$ in accordance with an embodiment of the present invention.

FIG. 41 shows an example i-t trace for Strep-Btn Kras-$G_{\omega 14}$ and the resulting % $I/I_o$ histogram compared with Strep-Btn $C_{40}$. Strep-Btn Kras-$G_{\omega 14}$ produces current blockage levels similar to Strep-Btn $C_{40}$, but with a larger spread.

Figure 42:
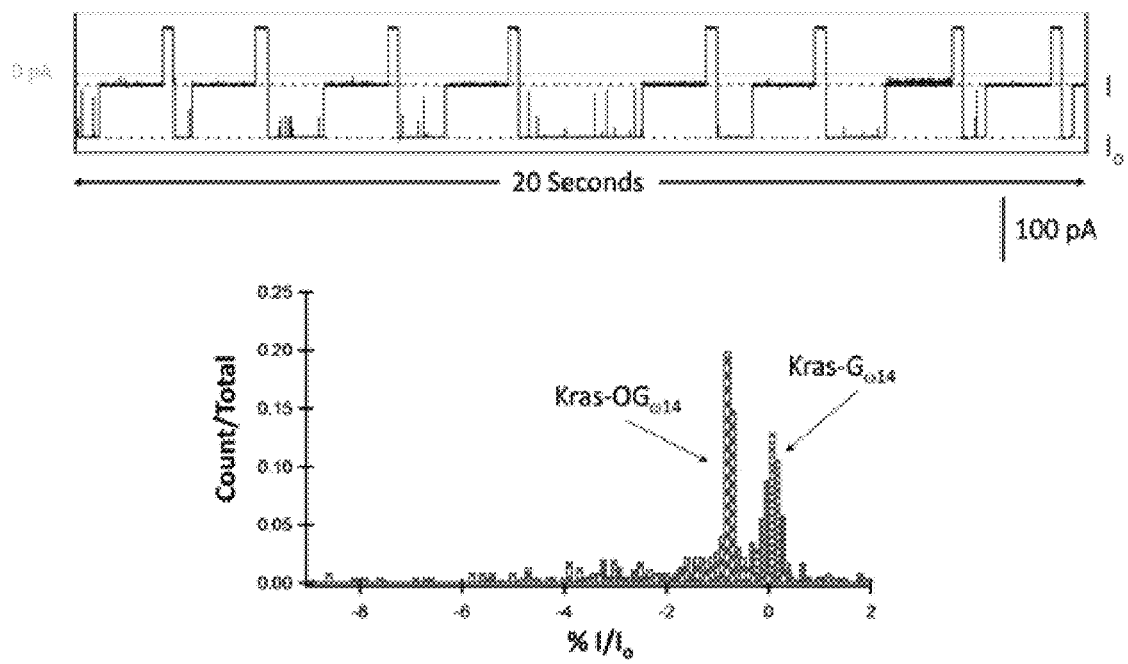
FIG. 42 shows an example i-t trace for Strep-Btn Kras-$OG_{\omega14}$ and the resulting % $I/I_o$ histogram compared with Strep-Btn Kras-$G_{\omega14}$ in accordance with an embodiment of the present invention.

FIG. 42 shows an example i-t trace for Strep-Btn Kras-$OG_{\omega 14}$ and the resulting % $I/I_o$ histogram compared with Strep-Btn Kras-$G_{\omega 14}$.

Figure 43:
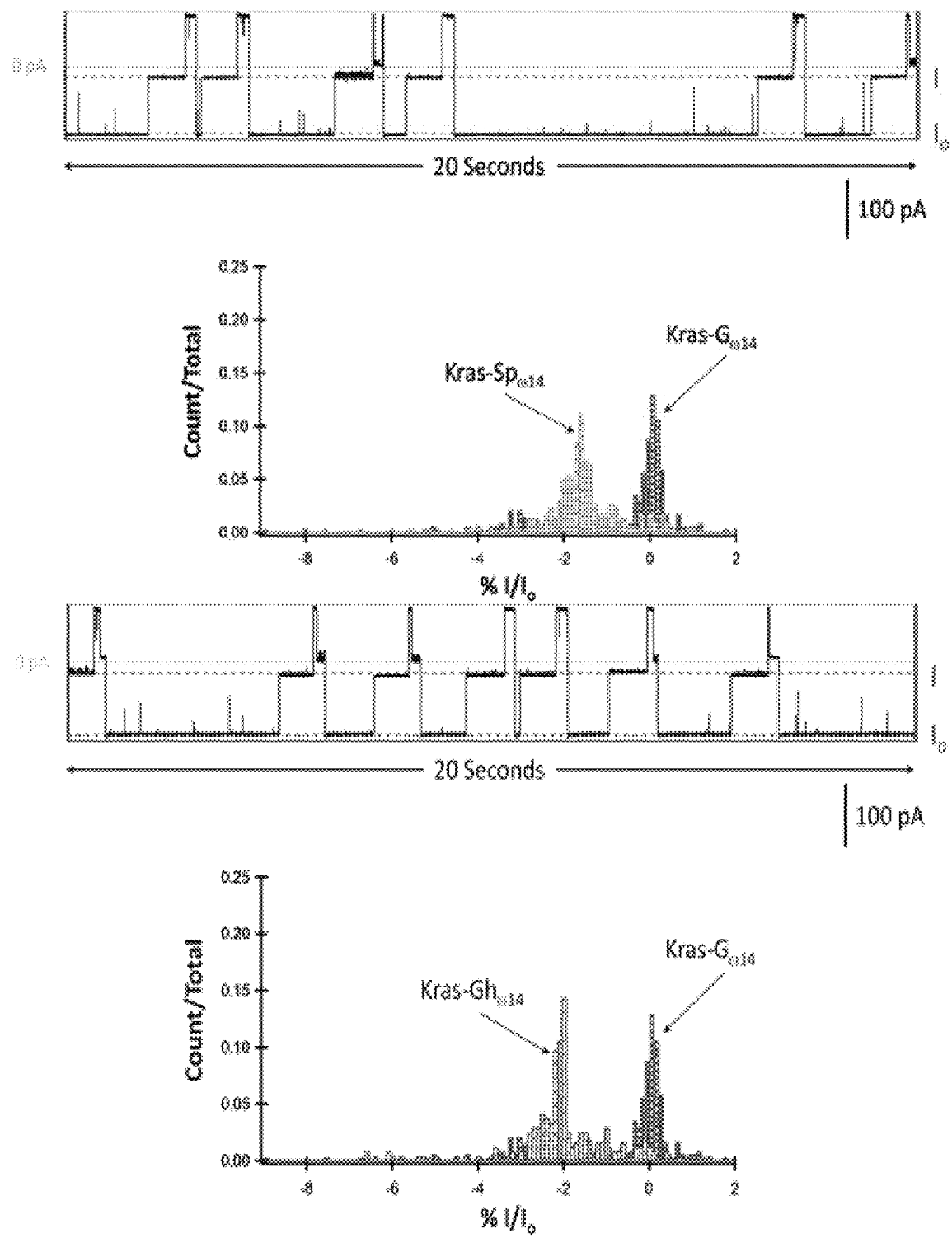
FIG. 43 shows example i-t traces for Strep-Btn Kras-$Sp_{\omega14}$ and Strep-Btn Kras-$Gh_{\omega14}$, and the resulting % $I/I_o$ histograms compared with Strep-Btn Kras-$G_{\omega14}$ in accordance with an embodiment of the present invention.

FIG. 43 shows example i-t traces for Strep-Btn Kras-$Sp_{\omega 14}$ (upper) and Strep-Btn Kras-$Gh_{\omega 14}$ (lower), and the resulting % $I/I_o$ histograms compared with Strep-Btn Kras-$G_{\omega 14}$.

Figure 44:
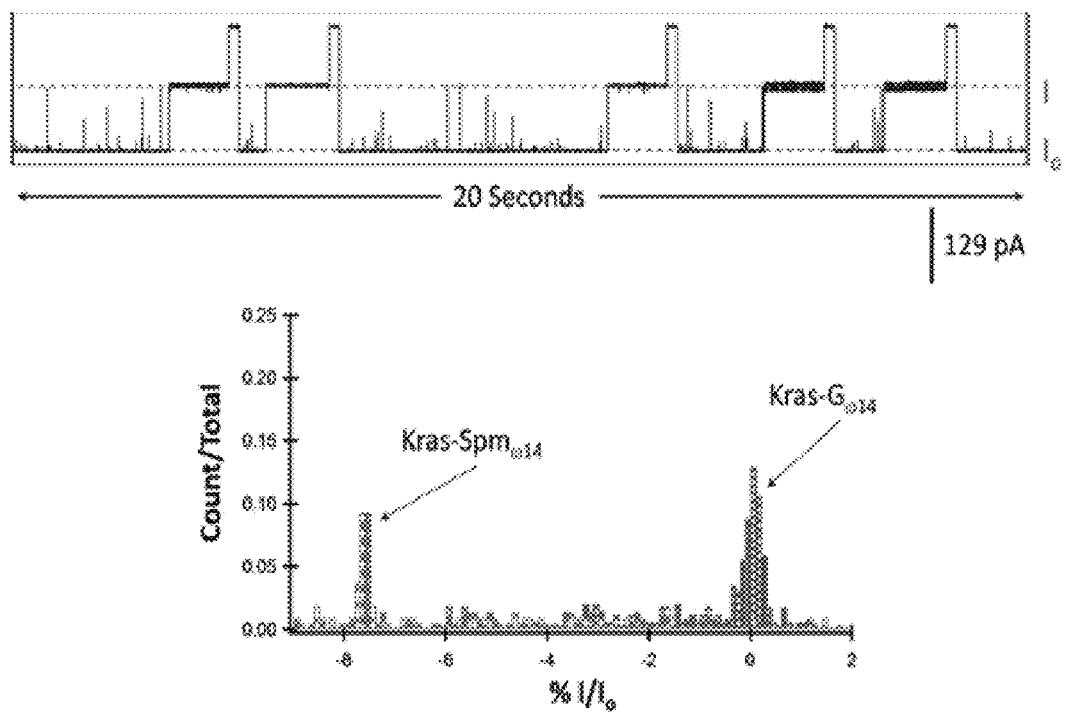
FIG. 44 shows an example i-t trace for Strep-Btn Kras-$Spm_{\omega14}$ and % $I/I_o$ histogram compared with Strep-Btn Kras-$G_{\omega14}$ in accordance with an embodiment of the present invention.

FIG. 44 shows an example i-t trace for Strep-Btn Kras-$Spm_{\omega 14}$ and % $I/I_o$ histogram compared with Strep-Btn Kras-$G_{\omega 14}$. Strep-Btn Kras-$Spm_{\omega 14}$ yields deeper current blockages relative to Strep-Btn Kras-$G_{\omega 14}$, and a single % $I/I_o$ peak that is sharper relative to Strep-Btn $C_{39}Spm_{\omega 14}$.

Figure 45:
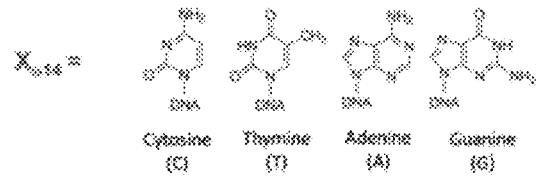
FIG. 45 shows % $I/I_o$ histograms for native base substitutions at position $\omega14$ within a poly-dC background, Strep-Btn $C_{39}X_{\omega14}$, where X=A, T, or G (SEQ ID NO:9) in accordance with an embodiment of the present invention.
Figure 45:
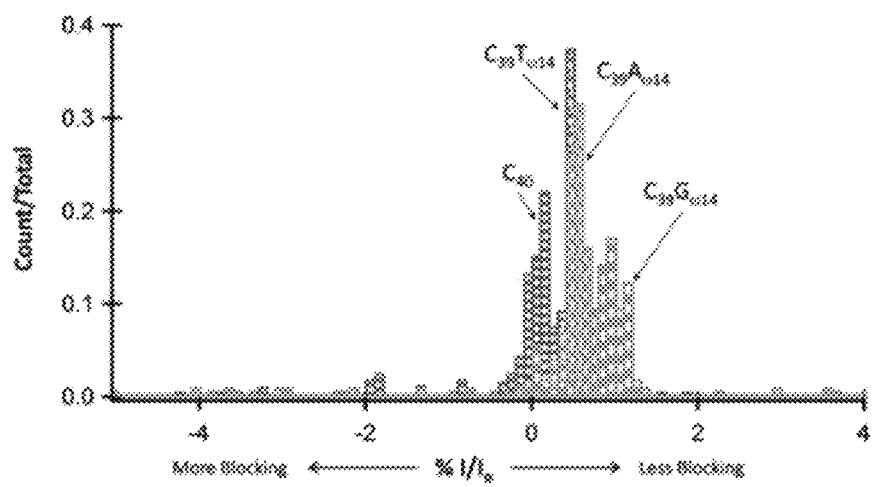

FIG. 45 shows % $I/I_o$ histograms for native base substitutions at position $\omega 14$ within a poly-dC background, Strep-Btn $C_{39}X_{\omega 14}$, where X=A, T, or G. Strep-Btn $C_{40}$ is used as a reference sample; the % $I/I_o$ for Strep-Btn $C_{40}$ is set to 0 and % $I/I_o$ for all other samples is relative to Strep-Btn $C_{40}$.

Figure 46:
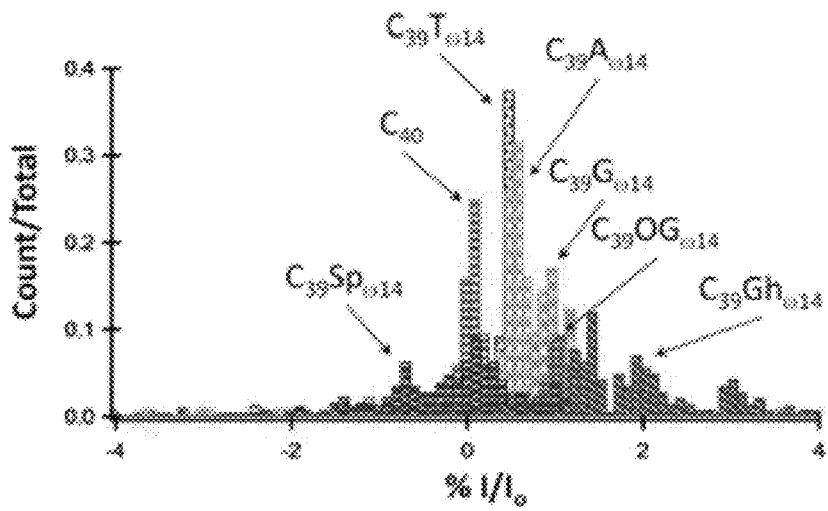
FIG. 46 shows current blockage histograms for Strep-Btn $C_{39}X_{\omega14}$, where X=C, T, A, G, OG, Sp, and Gh in accordance with an embodiment of the present invention.

FIG. 46 shows current blockage histograms for Strep-Btn $C_{39}X_{\omega 14}$, where X=C, T, A, G, OG, Sp, and Gh. Strep-Btn $C_{40}$ is used as a reference sample; the % $I/I_o$ for Strep-Btn $C_{40}$ is set to 0 and % $I/I_o$ for all other samples is relative to Strep-Btn $C_{40}$.

Figure 47:
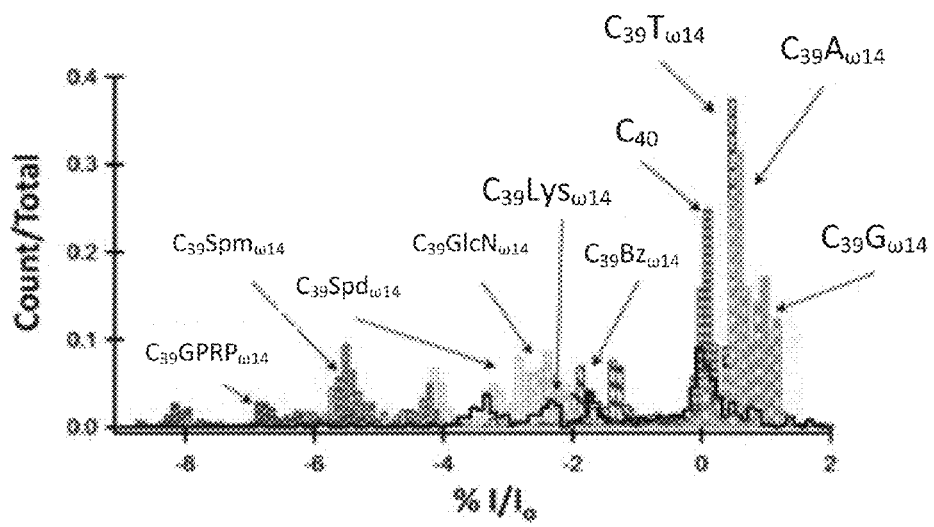
FIG. 47 shows current blockage histograms for Strep-Btn $C_{39}X_{\omega14}$, where X=C, T, A, G, Lys, Bz, GlcN, Spd, Spm, and GPRP in accordance with an embodiment of the present invention.

FIG. 47 shows current blockage histograms for Strep-Btn $C_{39}X_{\omega 14}$, where X=C, T, A, G, Lys, Bz, GlcN, Spd, Spm, and GPRP. $C_{40}$ was used as a reference sample; the % $I/I_o$ for $C_{40}$ was set equal to 0, and % $I/I_o$ for all other samples is relative to $C_{40}$.

Example 6

DNA Abasic Site Adducts

1. Preparation and Synthesis of DNA Abasic Sites Adducts
Chemicals.

KCl, EDTA, Tris-HCl, taurine, Arg-His, D-(+)-glucosamine, Gly-Pro-Arg-Pro amide, streptomycin, [15-crown-5]-methylamine and [18-crown-6]-methylamine, NaCNBH$_3$, wild-type α-HL, phospholipid 1,2-diphytanoyl-sn-glycero-3-phosphocholine (DPhPC), streptavidin and urical-DNA glycosylase (UDG) were purchased from commercial suppliers and used without further purification.

1.1. DNA Ab Adduct Synthesis and Characterization

The oligodeoxynucleotides (ODN) were synthesized from commercially available phosphoramidites (Glen Research, Sterling, Va.) by the DNA-Peptide Core Facility at the University of Utah. After synthesis, each ODN was cleaved from the synthetic column and deprotected according to the manufacturer's protocols, followed by purification using a semi-preparation ion-exchange HPLC column with a linear gradient of 25% to 100% B over 35 min while monitoring absorbance at 260 nm (A=20 mM Tris, 1 M NaCl pH 7 in 10% CH$_3$CN/90% ddH$_2$O, B=10% CH$_3$CN/90% ddH$_2$O, flow rate=3 mL/min) Uridine-containing oligomers (10 μM, 1 nmole) and 1 unit UDG were thermally equilibrated in UDG buffer (pH 8.0) at 37° C. for 30 min, followed by dialysis against ddH$_2$O for 12 h. The resulting AP-containing ODNs (10 μM, 1 nmole) were dried and resuspended in MOPS buffer (pH 6.5), followed by the addition of the appropriate amine (20 mM, 2 μmoles) and NaCNBH$_3$ (100 mM, 10 μmoles); then the reactions were kept at 37° C. for 24 h. Unreacted AP-containing ODNs were cleaved by 0.1 M NaOH. After dialysis again ddH$_2$O for 12 h, all products were purified by analytical ion-exchange HPLC running a linear gradient of 25% to 100% B over 35 mM while monitoring absorbance at 260 nm (A=20 mM Tris, 1 M NaCl pH 7 in 10% CH$_3$CN/90% ddH$_2$O, B=10% CH$_3$CN/90% ddH$_2$O, flow rate=1 mL/min). Analysis of the crude reaction products indicated the yields of approximately 85-90%. The identities of the 3'-biotinylated ODNs were determined by negative ion electron spray (ESI$^-$) mass spectrometry on a Micromass Quattro II mass spectrometer equipped with Zspray API source in the mass spectrometry laboratory at the Department of Chemistry, University of Utah.

1.2. Single Ion-Channel Current Recording
Materials.

Ultra-pure water (>18 MΩ·cm) was prepared by a Barnstead E-pure water purifier and used to make buffered electrolyte solution (1.0 M KCl, 1.0 mM EDTA, 25 mM Tris, pH=7.9) that was used for the single ion channel current recording. The electrolyte was filtered with a sterile 0.22 mm Millipore vacuum filter before the measurement. The protein α-HL was diluted to a 0.5 mg/mL solution in ultra-pure water and the lipid DPhPC was dissolved in decane to a concentration of 10 mg/mL, both of which were stored in a −20° C. freezer. The glass nanopore membrane (GNM) (radius=600 nm) was silanized in 2% (v:v) 3-cyanopropyldimethylchlorosilane in CH$_3$CN for 6 h. Ag/AgCl electrodes were prepared by soaking silver wires (diameter=0.25 mm) in bleach. In the immobilization studies, the 3'-biotinylated ODNs (160 pmol) were mixed with streptavidin (40 pmol) and kept at 23° C. for 20 min before the measurements, while in the translocation studies, the 87-mer ODNs were used directly after purification and dialysis.

Single Ion-Channel Recording Measurements.

A custom built high-impedance, low noise amplifier and data acquisition system, donated by Electronic Bio Sciences, San Diego, Calif., was used for the current-time (i-t) recordings. The GNM was rinsed with $CH_3CN$, ethanol and ultra-pure water, and then filled with the electrolyte described above. A pipette holder with a pressure gauge and a 10 mL gas-tight syringe was used to locate the GNM to the DC system. Two Ag/AgCl electrodes were positioned inside and outside of the GNM to apply a voltage.

The lipid DPhPC solution (1 μL) was painted on the GNM surface using a plastic pipette tip (flat gel-loading tips, 1-200 μL) to form a suspended bilayer, which was confirmed by the resistance of approximately 100 GΩ, a dramatic decrease from that of an open GNM orifice (10 MΩ). After the addition of α-HL (0.2 μL), pressure was applied to assist the insertion of the ion channel, which had a resistance of around 1 GΩ under these conditions.

In the immobilization studies, Strep-Btn DNA (40 pmol, 200 nM) was added in the cell and more than 200 capture/release events were collected under −120 mV bias with a 10 kHz low pass filter, and 50 kHz data acquisition rate. Then the same amount of Strep-Btn $C_{40}$ was added as an internal standard, and ~200 events were collected for each strand under the same conditions. As for the translocation studies, 87-mer DNA (2 nmol, 10 μM) was added and more than 2000 events were collected under different voltages (−80, −100, −120, −160 mV) with a 100 kHz low pass filter, and 500 kHz data acquisition rate.

Immobilization Data Analysis.

The Strep-Btn DNA was retained in the ion channel for 1 s and a histogram of the percentage residual current % $I/I_o$ was plotted with a bin width of 0.1%, setting Strep-Btn $C_{40}$ 0%.

Translocation Data Analysis.

As for the poly-$dC_{87}$, the histogram of events longer than 0.01 ms was fit into a Gaussian model with a peak location $t_p$ and events with duration $t_D > t_p$ were selected and fit into an exponential decay model with a decay constant τ under different voltages, as described in the early report.[2] As for the poly-$dC_{43}GPRPdC_{43}$, the events that had longer $t_D$ than the $t_p$ of poly-$dC_{87}$ under the corresponding voltage were fit into an exponential decay model, while the constant τ was compared to poly-$dC_{87}$. A bin width of 0.01 ms was applied for all the analysis.

Figure 48:
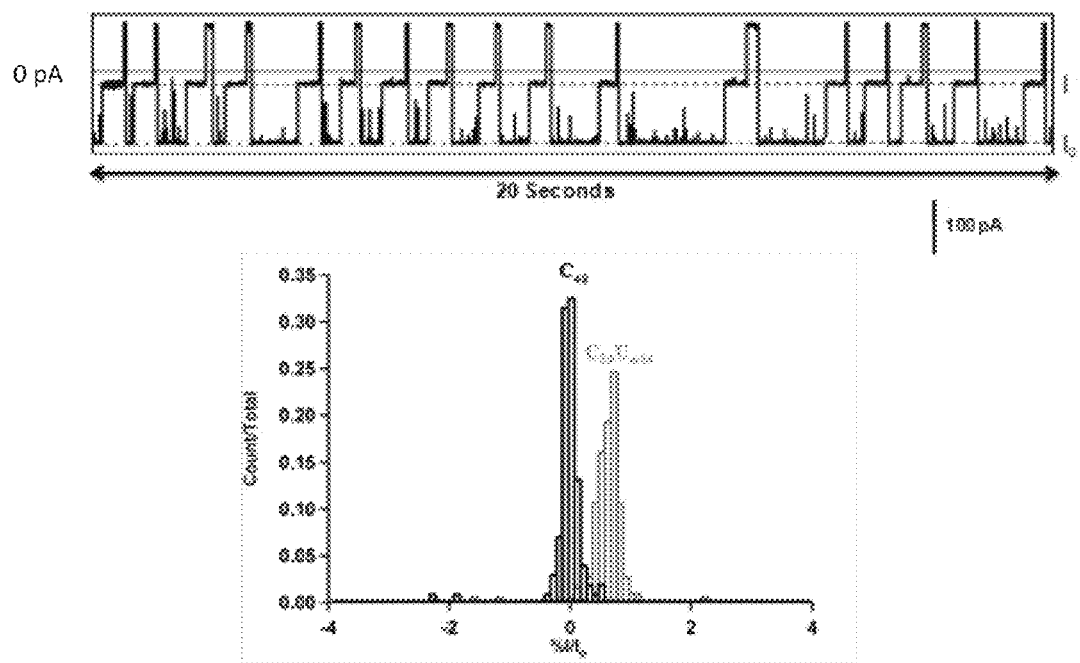
FIG. 48 shows an example i-t trace for Strep-Btn $C_{39}U_{\omega14}$ and % $I/I_o$ histogram compared with Strep-Btn $C_{40}$ in accordance with an embodiment of the present invention.

2. Example i-t Traces and Individual % $I/I_o$ Histograms in Immobilization Studies FIG. 48 shows an example i-t trace for Strep-Btn $C_{39}U_{ω14}$ and % $I/I_o$ histogram compared with Strep-Btn $C_{40}$.

Figure 49:
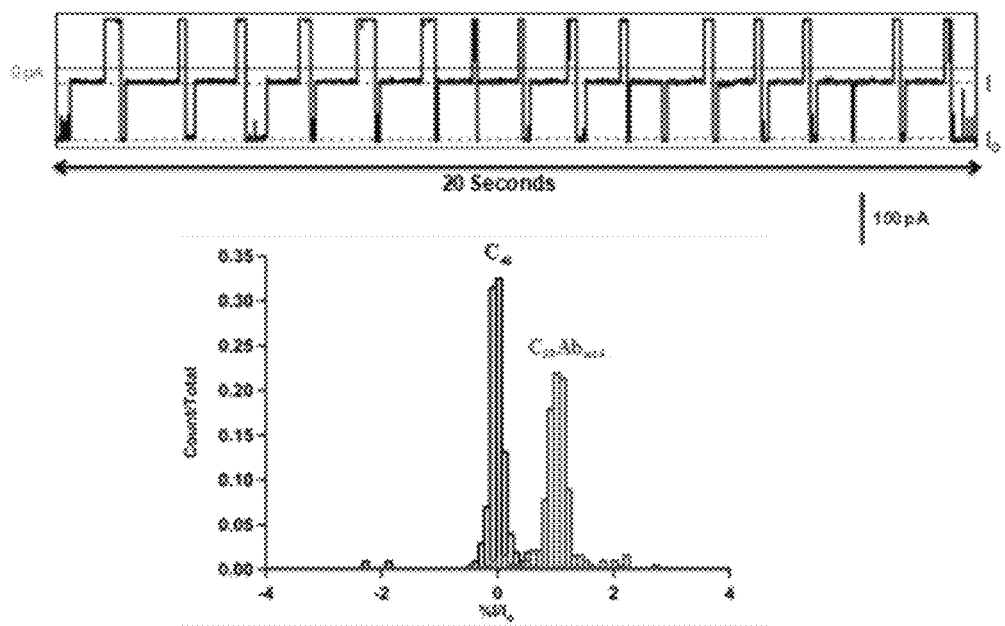
FIG. 49 shows an example i-t trace for Strep-Btn $C_{39}Ab_{\omega14}$ and % $I/I_o$ histogram compared with Strep-Btn $C_{40}$ in accordance with an embodiment of the present invention.

FIG. 49 shows an example i-t trace for Strep-Btn $C_{39}Ab_{ω14}$ and % $I/I_o$ histogram compared with Strep-Btn $C_{40}$.

Figure 50:
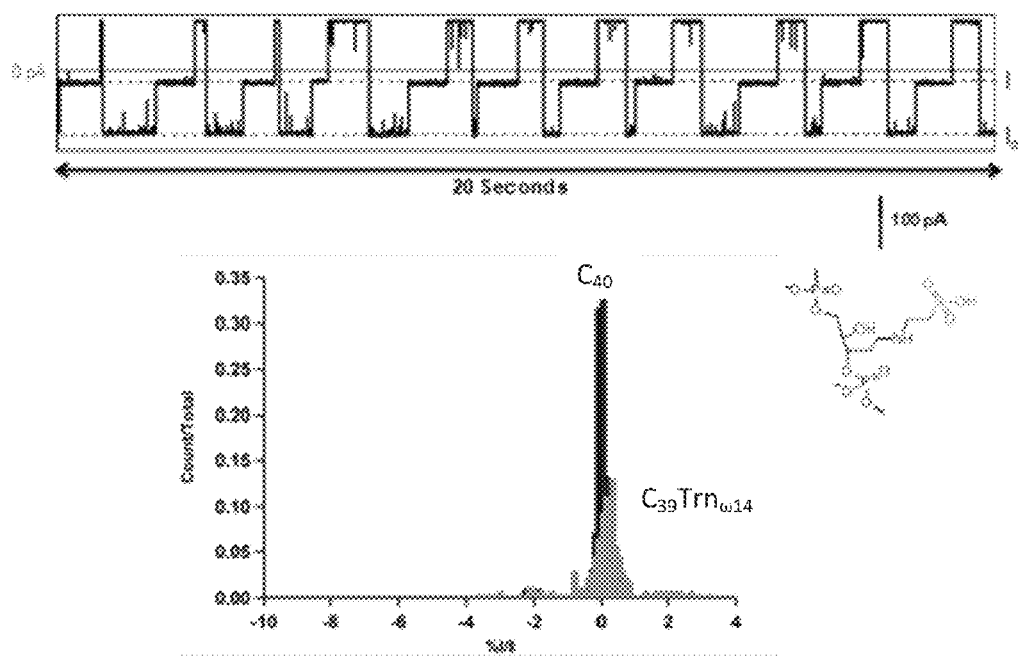
FIG. 50 shows an example i-t trace for Strep-Btn $C_{39}Trn_{\omega14}$ and % $I/I_o$ histogram compared with Strep-Btn $C_{40}$ in accordance with an embodiment of the present invention.

FIG. 50 shows an example i-t trace for Strep-Btn $C_{39}Trn_{ω14}$ and % $I/I_o$ histogram compared with Strep-Btn $C_{40}$.

Figure 51:
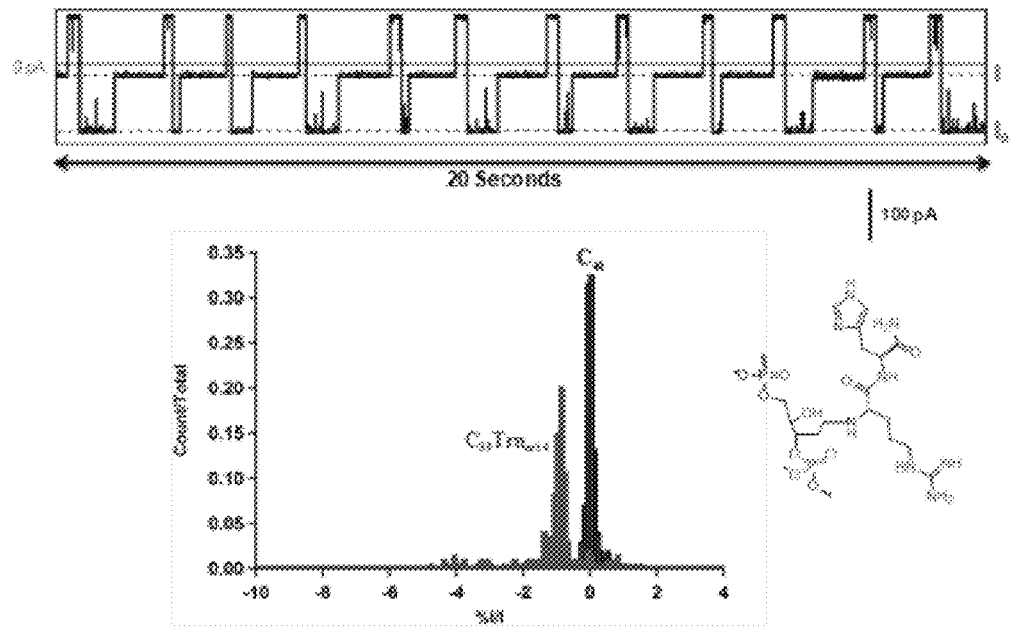
FIG. 51 shows an example i-t trace for Strep-Btn $C_{39}RH_{\omega14}$ and % $I/I_o$ histogram compared with Strep-Btn $C_{40}$ in accordance with an embodiment of the present invention.

FIG. 51 shows an example i-t trace for Strep-Btn $C_{39}RH_{ω14}$ and % $I/I_o$ histogram compared with Strep-Btn $C_{40}$.

Figure 52:
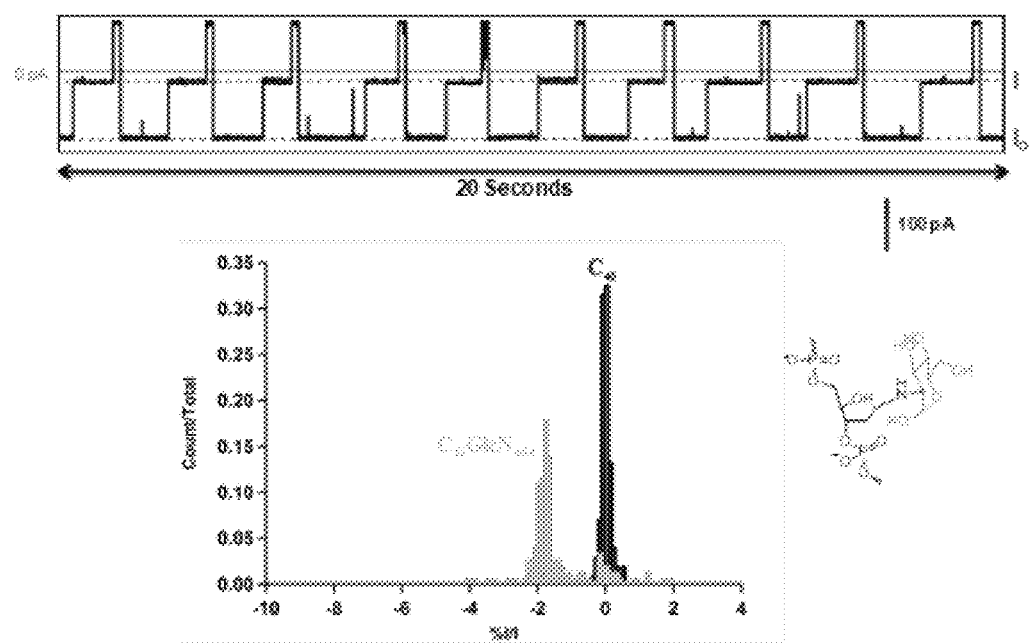
FIG. 52 shows an example i-t trace for Strep-Btn $C_{39}GlcN_{\omega14}$ and % $I/I_o$ histogram compared with Strep-Btn $C_{40}$ in accordance with an embodiment of the present invention.

FIG. 52 shows an example i-t trace for Strep-Btn $C_{39}GlcN_{ω14}$ and % $I/I_o$ histogram compared with Strep-Btn $C_{40}$.

Figure 53:
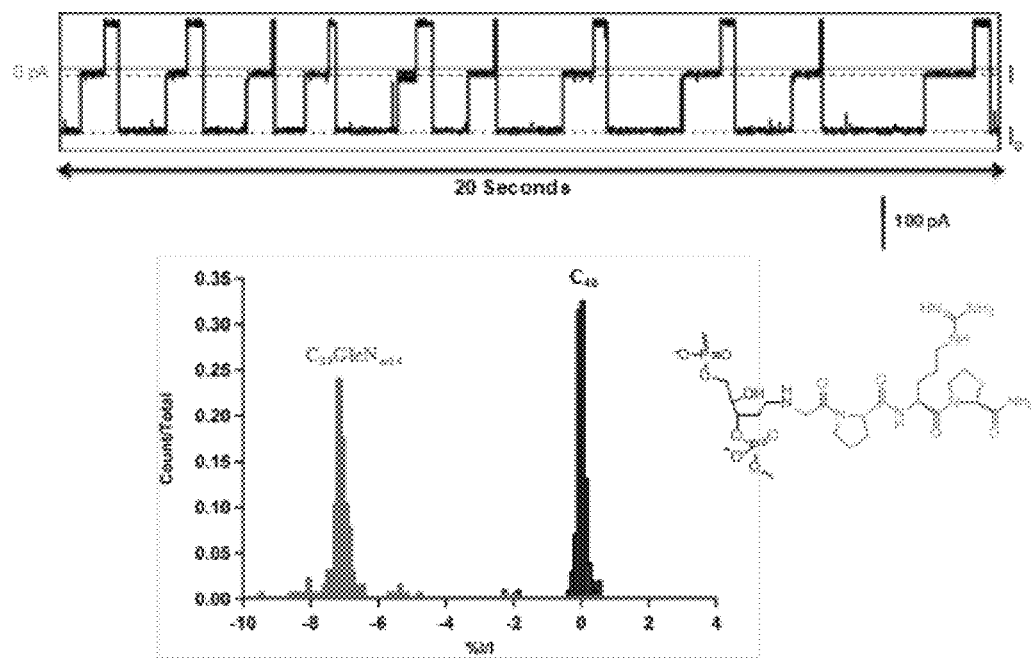
FIG. 53 shows an example i-t trace for Strep-Btn $C_{39}GPRP_{\omega14}$ and % $I/I_o$ histogram compared with Strep-Btn $C_{40}$ in accordance with an embodiment of the present invention.

FIG. 53 shows an example i-t trace for Strep-Btn $C_{39}GPRP_{ω14}$ and % $I/I_o$ histogram compared with Strep-Btn $C_{40}$.

Figure 54:
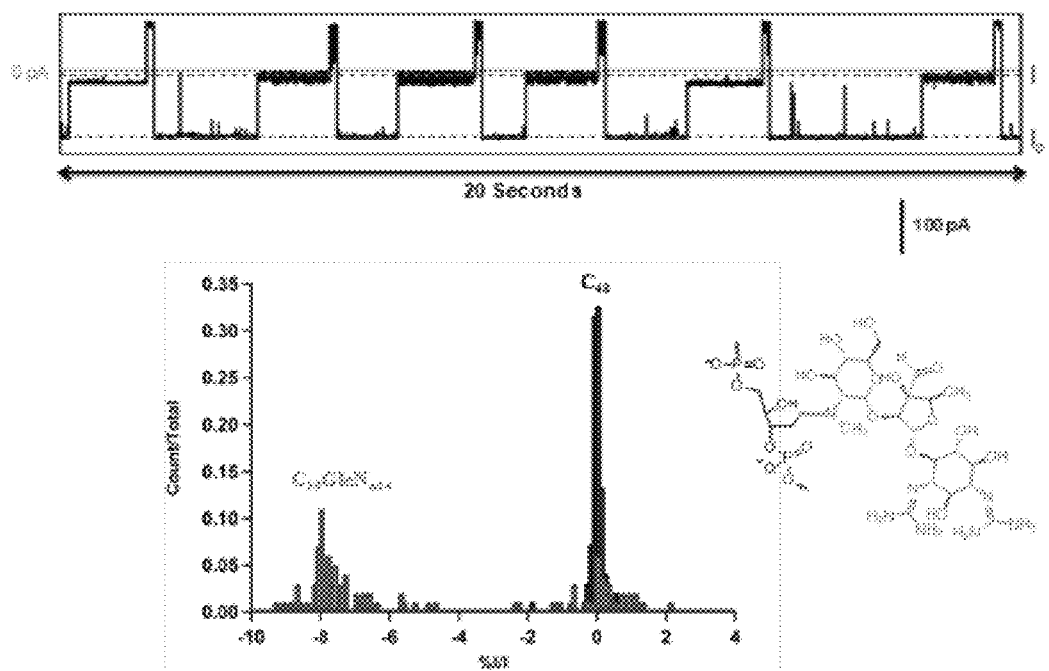
FIG. 54 shows an example i-t trace for Strep-Btn $C_{39}STM_{\omega14}$ and % $I/I_o$ histogram compared with Strep-Btn $C_{40}$ in accordance with an embodiment of the present invention.

FIG. 54 shows an example i-t trace for Strep-Btn $C_{39}STM_{ω14}$ and % $I/I_o$ histogram compared with Strep-Btn $C_{40}$.

Figure 55:
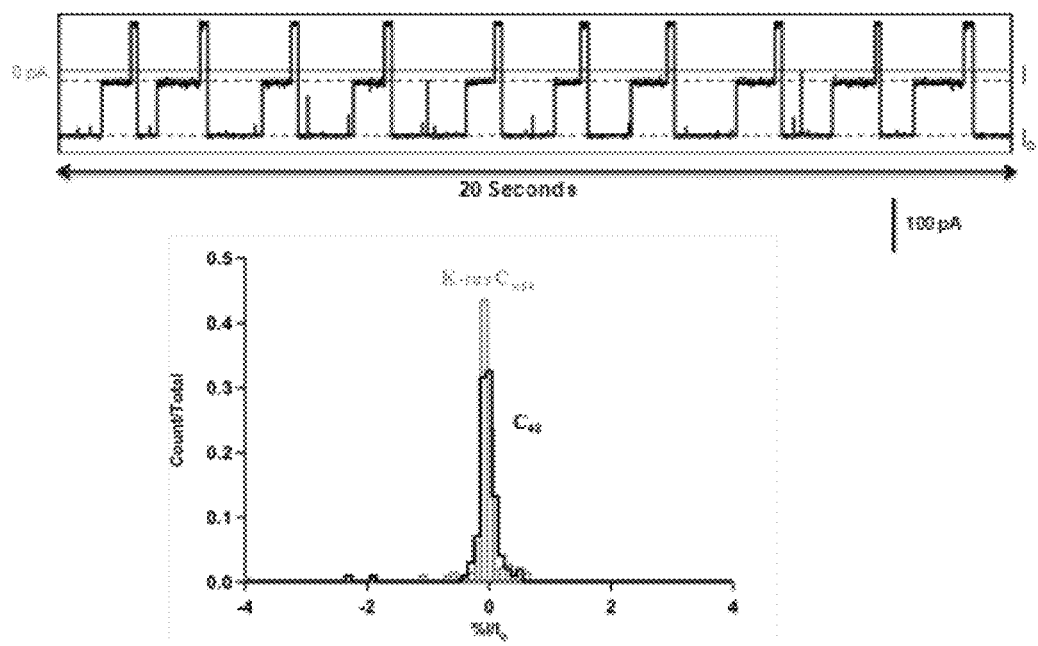
FIG. 55 shows an example i-t trace for Strep-Btn K-ras$C_{\omega14}$ and % $I/I_o$ histogram compared with Strep-Btn $C_{40}$ in accordance with an embodiment of the present invention.

FIG. 55 shows an example i-t trace for Strep-Btn K-ras$C_{ω14}$ and % $I/I_o$ histogram compared with Strep-Btn $C_{40}$.

Figure 56:
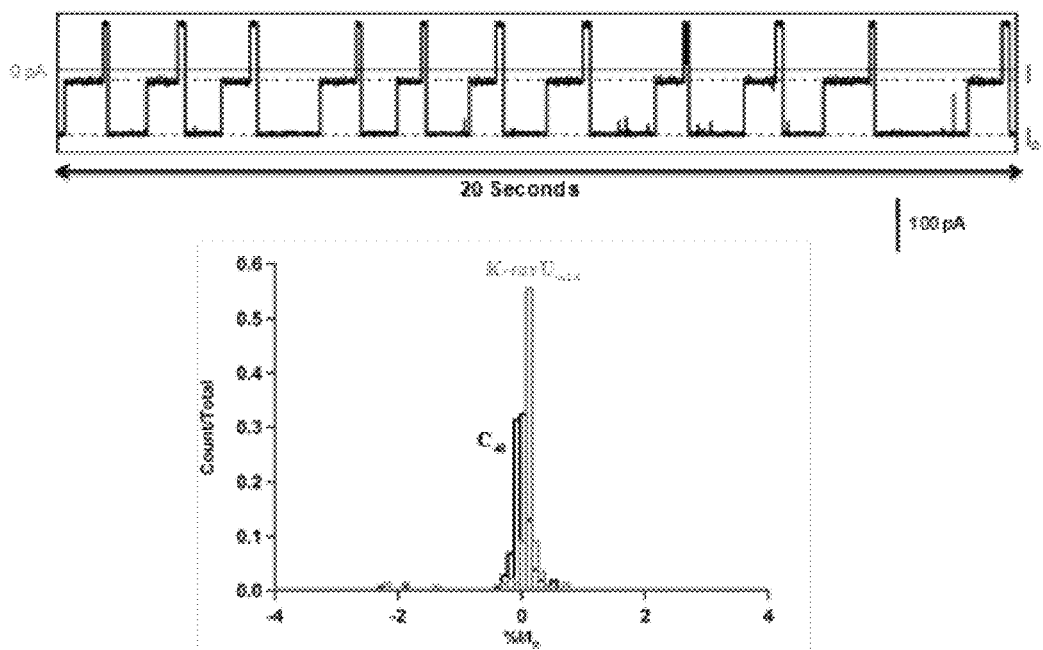
FIG. 56 shows an example i-t trace for Strep-Btn K-ras$U_{\omega14}$ and % $I/I_o$ histogram compared with Strep-Btn $C_{40}$ in accordance with an embodiment of the present invention.

FIG. 56 shows an example i-t trace for Strep-Btn K-ras$U_{ω14}$ and % $I/I_o$ histogram compared with Strep-Btn $C_{40}$.

Figure 57:
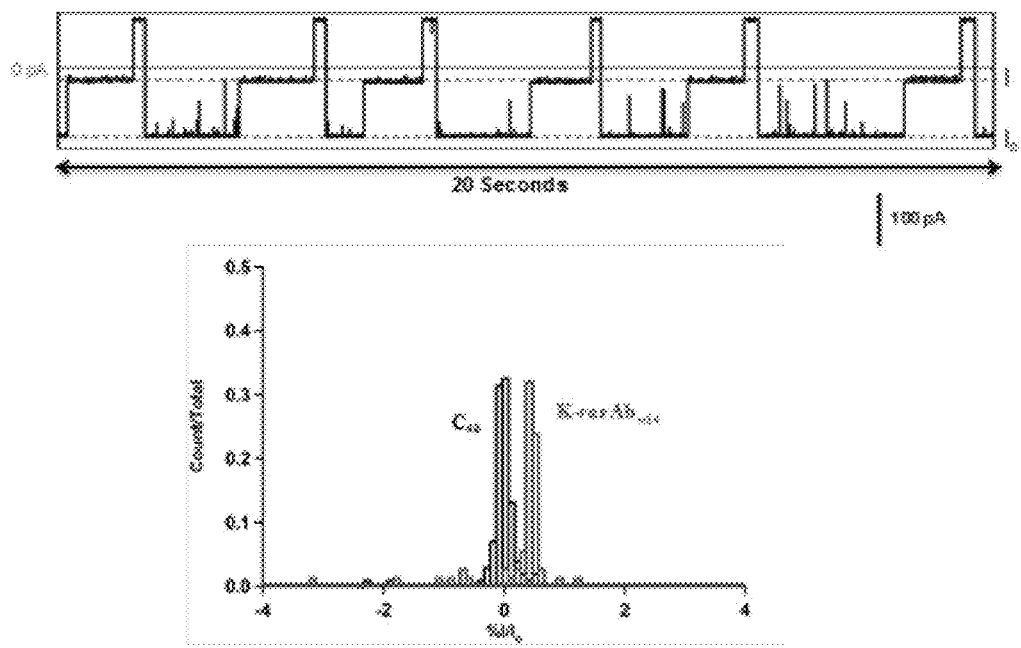
FIG. 57 shows an example i-t trace for Strep-Btn K-ras$Ab_{\omega14}$ and % $I/I_o$ histogram compared with Strep-Btn $C_{40}$ in accordance with an embodiment of the present invention.

FIG. 57 shows an example i-t trace for Strep-Btn K-rasAb$_{ω14}$ and % $I/I_o$ histogram compared with Strep-Btn $C_{40}$.

Figure 58:
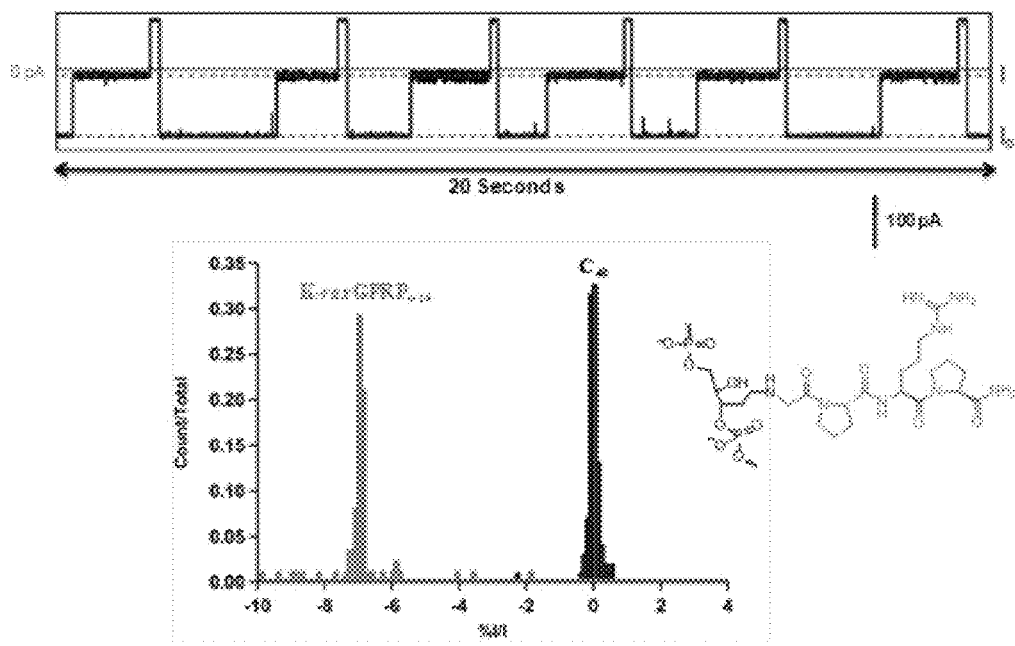
FIG. 58 shows an example i-t trace for Strep-Btn K-ras$GPRP_{\omega14}$ and % $I/I_o$ histogram compared with Strep-Btn $C_{40}$ in accordance with an embodiment of the present invention.

FIG. 58 shows an example i-t trace for Strep-Btn K-rasGPRP$_{ω14}$ and % $I/I_o$ histogram compared with Strep-Btn $C_{40}$.

Figure 59A:
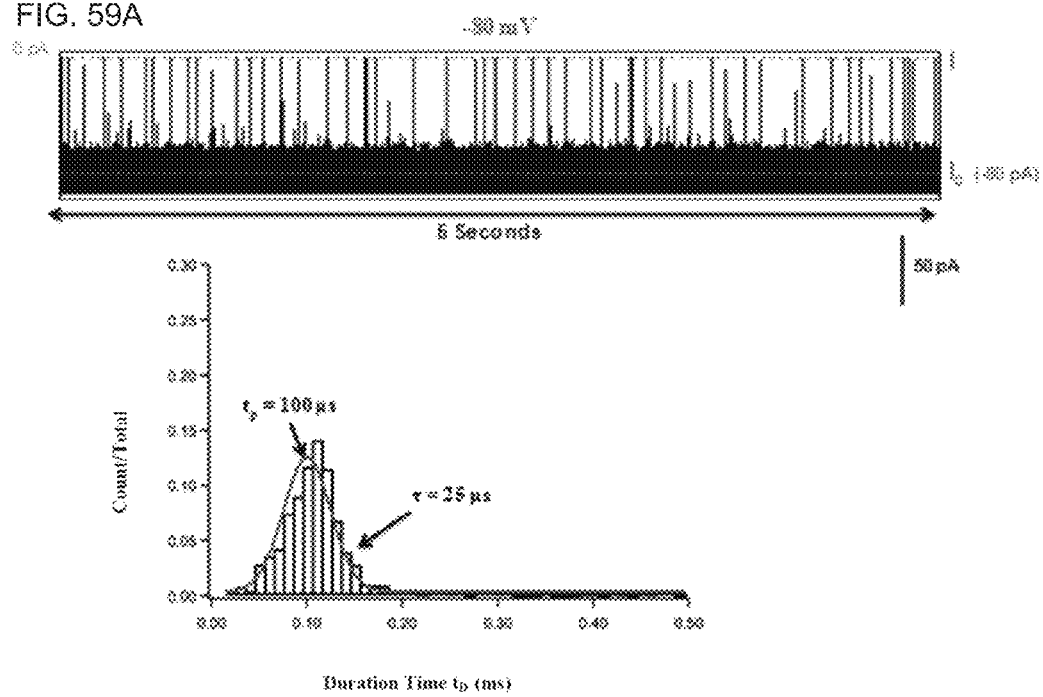
Figure 59B:
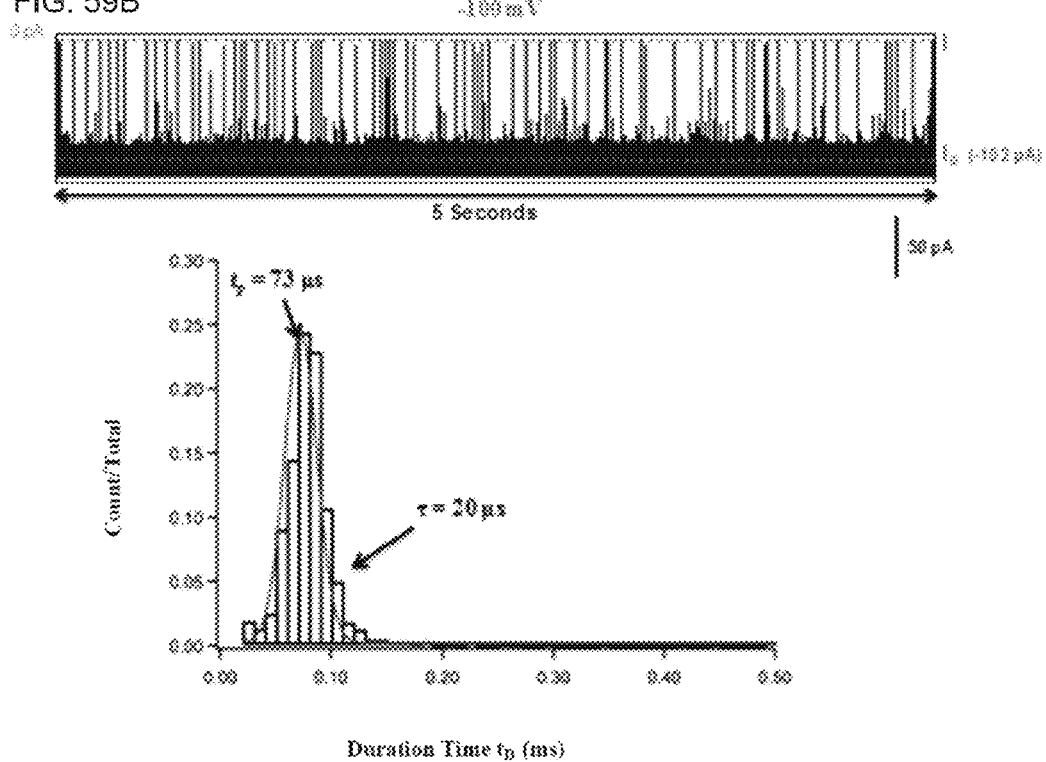
Figure 60A:
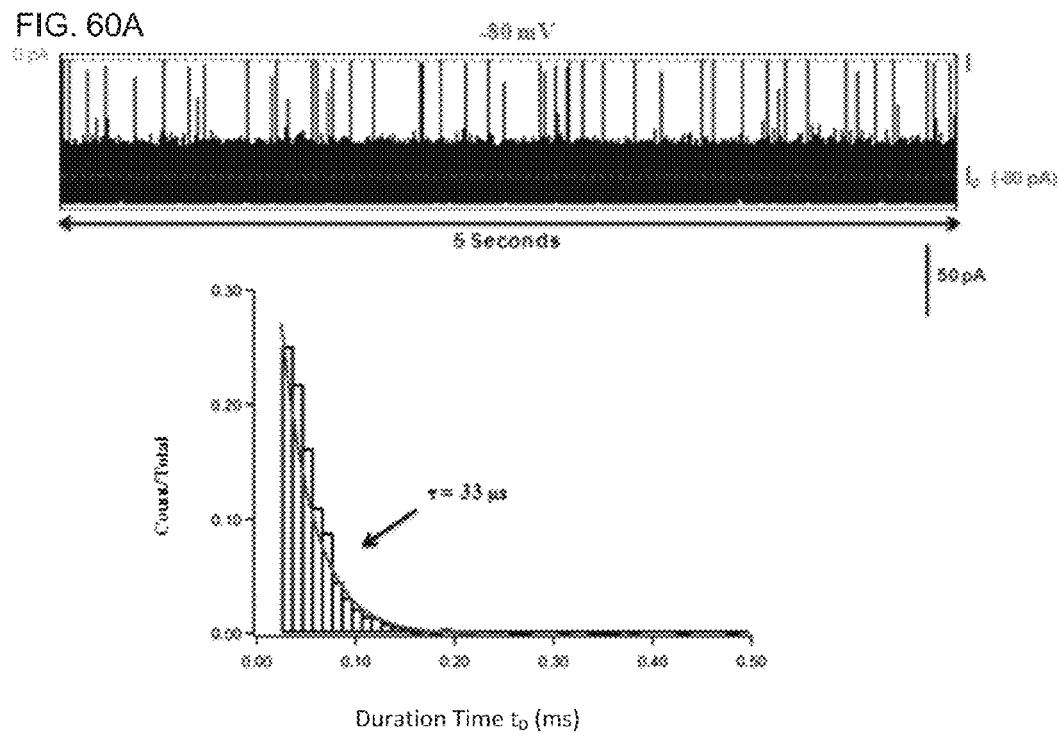
FIGS. 60A-D show example traces and individual duration histograms in translocation studies for poly-$dC_{43}GPRPdC_{43}$ and $t_D$ histogram under different voltages (FIG. 60A is −80 mV, FIG. 60B is −100 mV, FIG. 60C is −120 mV, and FIG. 60D is −160 mV) in accordance with an embodiment of the present invention.
Figure 60B:
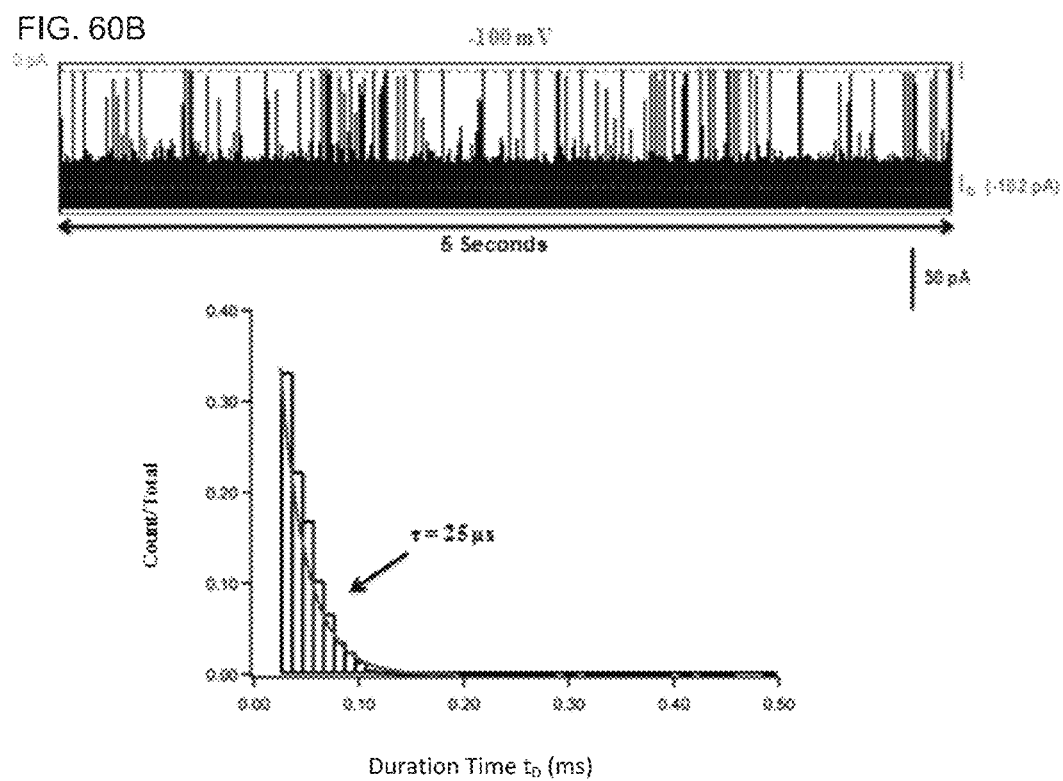
Figure 60C:
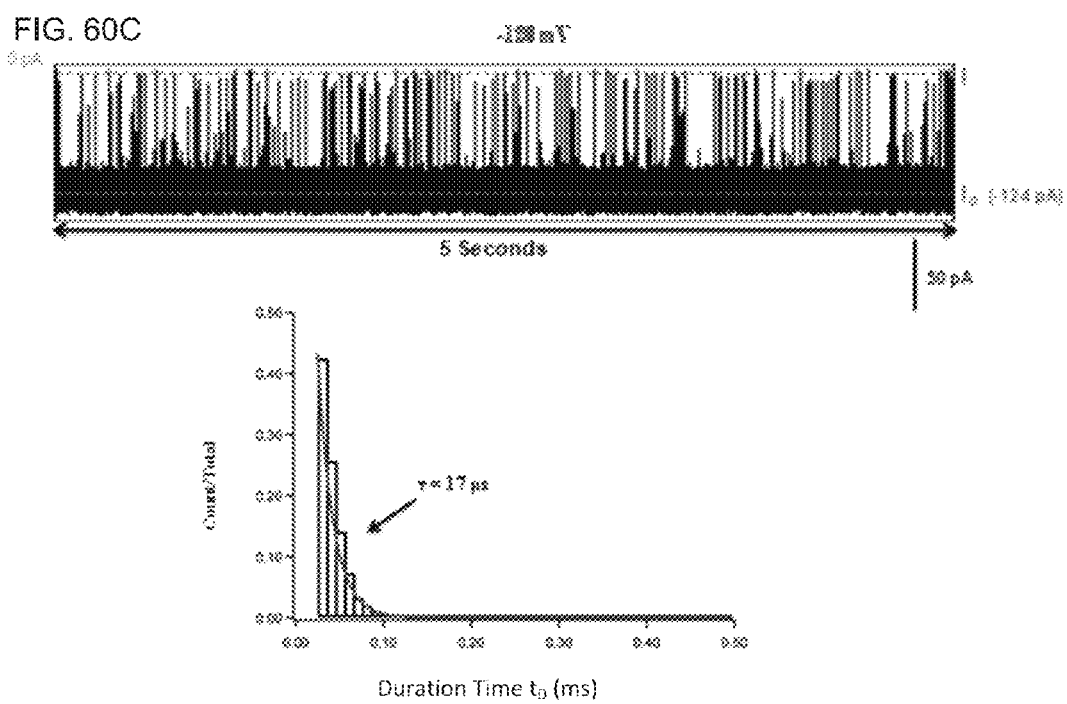
Figure 60D:
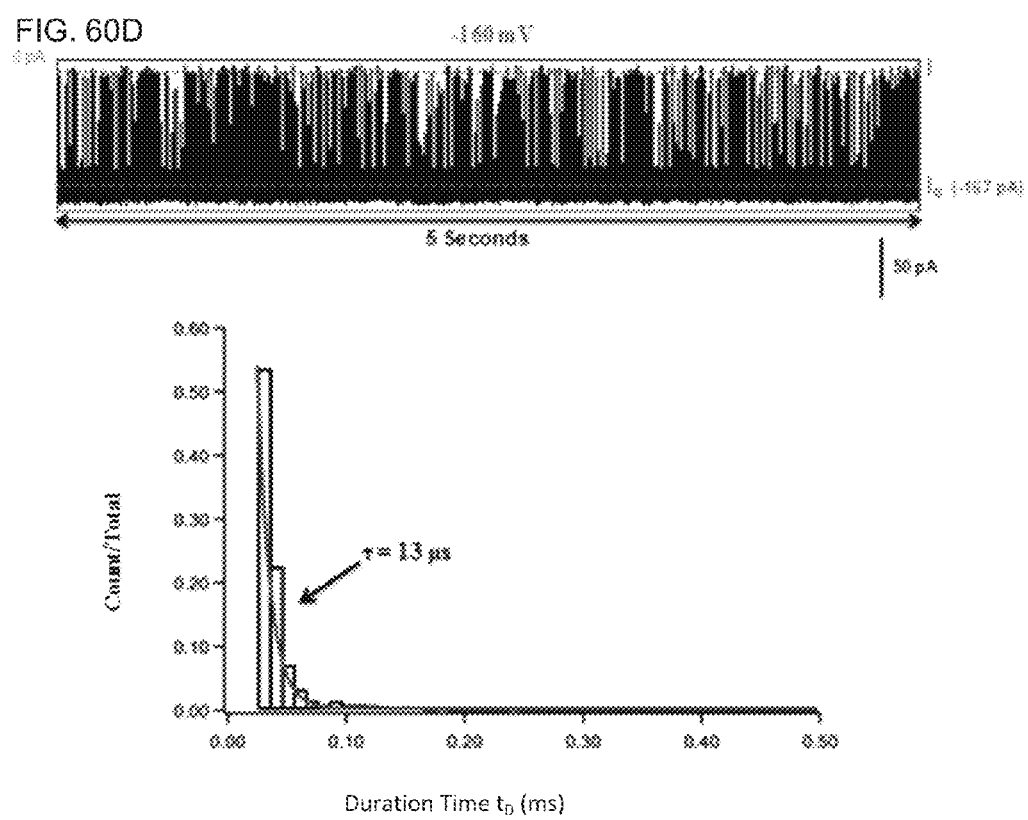

FIG. 59 shows example traces and individual duration histograms in translocation studies for poly-$dC_{87}$ and $t_D$ histogram under different voltages.

FIG. 60 shows example traces and individual duration histograms in translocation studies for poly-$dC_{43}GPRPdC_{43}$ and $t_D$ histogram under different voltages.

FIG. 63 shows example traces and individual duration histograms in translocation studies of poly-$dC_{43}$[18-crown-6]$dC_{43}$ and $t_D$ histogram under different voltages.

The foregoing detailed description describes the invention with reference to specific exemplary embodiments. However, it will be appreciated that various modifications and changes can be made without departing from the scope of the present invention as set forth in the appended claims. The detailed description and accompanying drawings are to be regarded as merely illustrative, rather than as restrictive, and all such modifications or changes, if any, are intended to fall within the scope of the present invention as described and set forth herein.

What is claimed is:

1. A system for detecting a current modulating compound, comprising:
   a membrane including an opening;
   a pair of electrodes configured to register changes in electrical current across the opening; and
   a nucleic acid comprising a nucleic acid adduct comprising a current modulating compound coupled to a nucleotide using a coupling reaction selected from the group consisting of oxidation, alkylation, platination, deamination, halogenation, glycosylation, conversion to an abasic site and further adduct formation, and combinations thereof, wherein the nucleic acid adduct is at least partially positioned within the opening, and wherein the current modulating compound is coupled to the nucleic acid at an abasic site.

2. The system of claim 1, wherein the opening is a nanopore.

3. The system of claim 2, wherein the nanopore is a conical nanopore.

4. The system of claim 1, wherein a lipid bilayer is suspended across the opening and the lipid bilayer includes a protein embedded in the lipid bilayer to form a channel such that transport of the nucleic acid adduct across the channel is inhibited while transport of non-adduct nucleic acid is not substantially inhibited.

5. The system of claim 1, wherein the current modulating compound includes a member selected from the group consisting of an alkane, an alkene, an alkyne, an aryl, a sugar, a carbohydrate, an azide, a halide, an amine, an imine, a peptide, a crown ether, a metal-binding ligand, a transition metal complex, and a combination thereof.

6. The nucleic acid of claim 1, wherein the current modulating compound comprises a crown ether.

7. The nucleic acid of claim 6, wherein the crown ether is selected from the group consisting of 18-crown-6 and 15-crown-5.

8. A system for detecting a current modulating compound, comprising:
- a membrane including an opening;
- a pair of electrodes configured to register changes in electrical current across the opening; and
- a nucleic acid comprising a nucleic acid adduct comprising a current modulating compound coupled to a nucleotide using a coupling reaction selected from the group consisting of oxidation, alkylation, platination, deamination, halogenation, glycosylation, conversion to an abasic site and further adduct formation, and combinations thereof, wherein the nucleic acid adduct is at least partially positioned within the opening, wherein the current modulating compound comprises a crown ether.

9. The nucleic acid of claim 8, wherein the crown ether is selected from the group consisting of 18-crown-6 and 15-crown-5.

* * * * *

SEQUENCE LISTING

<160> NUMBER OF SEQ ID NOS: 17

<210> SEQ ID NO 1
<211> LENGTH: 40
<212> TYPE: DNA
<213> ORGANISM: Artificial Sequence
<220> FEATURE:
<223> OTHER INFORMATION: Synthetic Oligonucleotide

<400> SEQUENCE: 1
cccccccccc cccccccccc cccccccccc cccccccccc                                40

<210> SEQ ID NO 2
<211> LENGTH: 40
<212> TYPE: DNA
<213> ORGANISM: Artificial Sequence

```
<220> FEATURE:
<223> OTHER INFORMATION: Synthetic Oligonucleotide

<400> SEQUENCE: 2
cccccccccc cccccccccc ccccccgccc cccccccccc                    40

<210> SEQ ID NO 3
<211> LENGTH: 40
<212> TYPE: DNA
<213> ORGANISM: Artificial Sequence
<220> FEATURE:
<223> OTHER INFORMATION: Synthetic Oligonucleotide

<400> SEQUENCE: 3
cccccccccc cccccccccc ccccccggcc cccccccccc                    40

<210> SEQ ID NO 4
<211> LENGTH: 40
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (27)..(27)
<223> OTHER INFORMATION: 8-oxoG derivative

<400> SEQUENCE: 4
cccccccccc cccccccccc ccccccgccc cccccccccc                    40

<210> SEQ ID NO 5
<211> LENGTH: 40
<212> TYPE: DNA
<213> ORGANISM: Artificial Sequence
<220> FEATURE:
<223> OTHER INFORMATION: Synthetic Oligonucleotide

<400> SEQUENCE: 5
cccccccccc cccccccccc cccccccccc ccgcccccccc                   40

<210> SEQ ID NO 6
<211> LENGTH: 40
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (33)..(33)
<223> OTHER INFORMATION: Benzylamine adduct

<400> SEQUENCE: 6
cccccccccc cccccccccc cccccccccc ccgcccccccc                   40

<210> SEQ ID NO 7
<211> LENGTH: 40
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (27)..(27)
<223> OTHER INFORMATION: Benzylamine adduct

<400> SEQUENCE: 7
cccccccccc cccccccccc ccccccgccc cccccccccc                    40
```

```
<210> SEQ ID NO 8
<211> LENGTH: 40
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (27)..(27)
<223> OTHER INFORMATION: Guanidinohydantoin derivative

<400> SEQUENCE: 8
cccccccccc cccccccccc ccccccgccc cccccccccc                              40

<210> SEQ ID NO 9
<211> LENGTH: 40
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (27)..(27)
<223> OTHER INFORMATION: n is a, c, g, or t

<400> SEQUENCE: 9
cccccccccc cccccccccc ccccccnccc cccccccccc                              40

<210> SEQ ID NO 10
<211> LENGTH: 87
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (44)..(44)
<223> OTHER INFORMATION: 18-crown-6 derivative

<400> SEQUENCE: 10
cccccccccc cccccccccc cccccccccc cccccccccc cccccccccc cccccccc          60 cccccccccc cccccccccc ccccccc                                            87

<210> SEQ ID NO 11
<211> LENGTH: 40
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (27)..(27)
<223> OTHER INFORMATION: 18-crown-6 derivative

<400> SEQUENCE: 11
cccccccccc cccccccccc cccccccccc cccccccccc                              40

<210> SEQ ID NO 12
<211> LENGTH: 11
<212> TYPE: DNA
<213> ORGANISM: Artificial Sequence
<220> FEATURE:
<223> OTHER INFORMATION: Synthetic Oligonucleotide

<400> SEQUENCE: 12
aatcgccgtt t                                                             11
```

```
<210> SEQ ID NO 13
<211> LENGTH: 13
<212> TYPE: DNA
<213> ORGANISM: Artificial Sequence
<220> FEATURE:
<223> OTHER INFORMATION: Synthetic Oligonucleotide

<400> SEQUENCE: 13
tagggatccc gta                                                          13

<210> SEQ ID NO 14
<211> LENGTH: 13
<212> TYPE: DNA
<213> ORGANISM: Artificial Sequence
<220> FEATURE:
<223> OTHER INFORMATION: Synthetic Oligonucleotide

<400> SEQUENCE: 14
taggggatcc gta                                                          13

<210> SEQ ID NO 15
<211> LENGTH: 64
<212> TYPE: DNA
<213> ORGANISM: Artificial Sequence
<220> FEATURE:
<223> OTHER INFORMATION: Synthetic Oligonucleotide

<400> SEQUENCE: 15
tttttttttt tttttttttt tttttttttt tggtttttt tttttttttt tttttttttt        60
tttt                                                                    64

<210> SEQ ID NO 16
<211> LENGTH: 64
<212> TYPE: DNA
<213> ORGANISM: Artificial Sequence
<220> FEATURE:
<223> OTHER INFORMATION: Synthetic Oligonucleotide

<400> SEQUENCE: 16
tttttttttt ttutttttt tttggttttt tggtttttg gttttttttt tutttttttt         60
tttt                                                                    64

<210> SEQ ID NO 17
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 17
catctgacgg ctcaa                                                        15
```